(12) United States Patent
Raymond et al.

(10) Patent No.: US 10,869,657 B2
(45) Date of Patent: *Dec. 22, 2020

(54) SURGICAL RETRACTOR SYSTEMS AND ILLUMINATED CANNULAE

(71) Applicant: DePuy Synthes Products, Inc., Raynham, MA (US)

(72) Inventors: Douglas Raymond, Bridgewater, MA (US); Connie Marchek, Foxboro, MA (US); Thomas W. Higginbotham, Independence, MO (US); Anthony R. Carlone, Bristol, RI (US); Katherine Herard Ray, Reston, VA (US); Timothy Beardsley, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 331 days.

This patent is subject to a terminal disclaimer.

(21) Appl. No.: 14/072,211

(22) Filed: Nov. 5, 2013

(65) Prior Publication Data
US 2014/0058210 A1    Feb. 27, 2014

Related U.S. Application Data

(63) Continuation of application No. 12/241,963, filed on Sep. 30, 2008, now Pat. No. 8,602,984, which is a
(Continued)

(51) Int. Cl.
*A61B 17/02* (2006.01)
*A61B 17/34* (2006.01)
(Continued)

(52) U.S. Cl.
CPC .......... *A61B 17/0218* (2013.01); *A61B 17/02* (2013.01); *A61B 17/3417* (2013.01);
(Continued)

(58) Field of Classification Search
USPC ........ 606/101–106, 114, 127–130, 133, 135, 606/138, 170, 171, 176, 183–185, 188,
(Continued)

(56) References Cited

U.S. PATENT DOCUMENTS

| 55,511 A | 6/1866 | Leutz |
|---|---|---|
| 147,867 A | 2/1874 | Schumacher |

(Continued)

FOREIGN PATENT DOCUMENTS

| EP | 0 190 014 A2 | 8/1986 |
|---|---|---|
| EP | 0428567 A1 | 5/1991 |

(Continued)

OTHER PUBLICATIONS

European Search Report for Application No. 11154715.4, dated Apr. 20, 2011.
(Continued)

*Primary Examiner* — Lynnsy M Summitt
(74) *Attorney, Agent, or Firm* — Nutter McClennen & Fish LLP

(57) ABSTRACT

This invention includes surgical retractors that comprise an expandable frame that includes at least two base components, a connector, and at least two retractor blades attached to the expandable frame. Also included are surgical retractors that comprise a housing component that includes a cylindrical portion and a contiguous blade portion, assemblies comprising a surgical retractor assembled to at least one obtruator, illuminated surgical cannulas, and methods of using the same during a surgical procedure.

4 Claims, 74 Drawing Sheets

Related U.S. Application Data continuation of application No. 11/016,347, filed on Dec. 17, 2004, now Pat. No. 7,491,168.

(60) Provisional application No. 60/530,565, filed on Dec. 18, 2003.

(51) Int. Cl.
  *A61B 90/30* (2016.01)
  *A61B 17/00* (2006.01)

(52) U.S. Cl.
  CPC ...... *A61B 17/3421* (2013.01); *A61B 17/3439* (2013.01); *A61B 17/0293* (2013.01); *A61B 17/3462* (2013.01); *A61B 2017/00261* (2013.01); *A61B 2017/00407* (2013.01); *A61B 2017/0256* (2013.01); *A61B 2017/3443* (2013.01); *A61B 2090/306* (2016.02)

(58) Field of Classification Search
  USPC ........ 606/190–206, 208, 210–225, 231, 233, 606/235, 237, 239, 242–245
  See application file for complete search history.

(56) References Cited

U.S. PATENT DOCUMENTS

| | | |
|---|---|---|
| 413,013 A | 10/1889 | Bainbridge |
| 447,761 A * | 3/1891 | Clough ............... A61B 1/32 600/224 |
| 458,708 A | 9/1891 | Daily |
| 475,975 A | 5/1892 | Clough |
| 563,236 A | 6/1896 | Penhall |
| 596,399 A | 12/1897 | Fox |
| 605,652 A | 6/1898 | Pitt |
| 761,821 A | 6/1904 | Clark et al. |
| 1,246,340 A | 11/1917 | Isaac |
| 1,260,604 A | 3/1918 | Verbsky |
| 1,275,520 A | 8/1918 | Bell |
| 1,587,897 A | 6/1926 | Cameron |
| 2,053,868 A | 9/1936 | Grosso |
| 2,320,709 A | 6/1943 | Arnesen |
| 2,532,162 A | 11/1950 | Goss |
| 2,592,190 A | 4/1952 | Rubens et al. |
| 2,693,795 A | 11/1954 | Grieshaber |
| 2,954,025 A | 9/1960 | Grieshaber |
| 3,038,468 A | 6/1962 | Raeuchle |
| 3,129,706 A | 4/1964 | Reynolds, Jr. |
| 3,227,156 A | 1/1966 | Gauthier |
| 3,246,646 A | 4/1966 | Murphy |
| 3,384,078 A | 5/1968 | Gauthier |
| 3,436,141 A | 4/1969 | Comte |
| 3,486,505 A | 12/1969 | Morrison |
| 3,522,799 A | 8/1970 | Gauthier |
| 3,563,236 A | 2/1971 | Hansson |
| 3,575,163 A | 4/1971 | Gasper |
| 3,650,266 A | 3/1972 | Pestka et al. |
| 3,716,047 A | 2/1973 | Moore et al. |
| 3,771,518 A | 11/1973 | Greissing |
| 3,807,393 A | 4/1974 | McDonald |
| 3,815,585 A | 6/1974 | Fiore |
| 3,848,601 A | 11/1974 | Ma et al. |
| 3,965,890 A | 6/1976 | Gauthier |
| 4,010,741 A | 3/1977 | Gauthier |
| 4,048,987 A * | 9/1977 | Hurson ................. 600/206 |
| 4,130,113 A | 12/1978 | Graham |
| 4,156,424 A | 5/1979 | Burgin |
| 4,254,763 A | 3/1981 | McCready et al. |
| 4,263,899 A | 4/1981 | Burgin |
| 4,274,398 A | 6/1981 | Scott, Jr. |
| 4,385,626 A | 5/1983 | Danz |
| 4,421,107 A | 12/1983 | Estes et al. |
| 4,434,791 A | 3/1984 | Darnell |
| 4,545,374 A | 10/1985 | Jacobson |
| 4,562,832 A | 1/1986 | Wilder et al. |
| 4,573,448 A | 3/1986 | Kambin |
| 4,597,382 A | 7/1986 | Perez, Jr. |
| 4,616,635 A | 10/1986 | Caspar et al. |
| 4,686,966 A | 8/1987 | Tsai |
| 4,726,356 A * | 2/1988 | Santilli ............... A61B 17/0206 600/232 |
| 4,747,394 A | 5/1988 | Watanabe |
| 4,765,311 A | 8/1988 | Kulik et al. |
| 4,805,984 A | 2/1989 | Cobb, Jr. |
| 4,817,587 A | 4/1989 | Janese |
| 4,862,891 A | 9/1989 | Smith |
| 4,872,451 A | 10/1989 | Moore et al. |
| 4,896,661 A | 1/1990 | Bogert et al. |
| 4,907,132 A | 3/1990 | Parker |
| 4,934,352 A | 6/1990 | Sullivan, Jr. |
| 5,000,163 A | 3/1991 | Ray et al. |
| 5,007,409 A | 4/1991 | Pope |
| 5,052,372 A | 10/1991 | Shapiro |
| 5,052,373 A | 10/1991 | Michelson |
| 5,072,720 A | 12/1991 | Francis et al. |
| 5,088,472 A * | 2/1992 | Fakhrai ............... A61B 17/0206 600/214 |
| 5,125,396 A | 6/1992 | Ray |
| 5,135,525 A | 8/1992 | Biscoping et al. |
| 5,158,543 A | 10/1992 | Lazarus |
| 5,171,279 A | 12/1992 | Mathews |
| 5,179,938 A | 1/1993 | Lonky |
| 5,195,505 A | 3/1993 | Josefsen |
| 5,231,973 A | 8/1993 | Dickie |
| 5,231,974 A | 8/1993 | Giglio et al. |
| 5,242,443 A | 9/1993 | Kambin |
| 5,279,567 A | 1/1994 | Ciaglia et al. |
| 5,284,129 A | 2/1994 | Agbodoe et al. |
| 5,292,309 A | 3/1994 | Van Tassel et al. |
| 5,297,538 A | 3/1994 | Daniel |
| 5,304,183 A | 4/1994 | Gourlay et al. |
| 5,312,360 A | 5/1994 | Behl |
| 5,318,010 A | 6/1994 | Lundberg |
| 5,329,938 A | 7/1994 | Lonky |
| 5,342,384 A | 8/1994 | Sugarbaker |
| 5,375,481 A | 12/1994 | Cabrera et al. |
| 5,382,139 A | 1/1995 | Kawaguchi et al. |
| 5,400,774 A | 3/1995 | Villalta et al. |
| 5,415,666 A | 5/1995 | Gourlay et al. |
| 5,429,121 A | 7/1995 | Gadelius |
| 5,439,464 A | 8/1995 | Shapiro |
| 5,460,165 A | 10/1995 | Mayes |
| 5,472,426 A | 12/1995 | Bonati et al. |
| 5,493,464 A | 2/1996 | Koshikawa |
| 5,499,964 A | 3/1996 | Beck et al. |
| 5,503,617 A | 4/1996 | Jako |
| 5,509,893 A | 4/1996 | Pracas |
| 5,520,610 A | 5/1996 | Giglio et al. |
| 5,554,101 A | 9/1996 | Matula et al. |
| 5,569,248 A | 10/1996 | Mathews |
| 5,616,117 A | 4/1997 | Dinkier et al. |
| 5,667,481 A | 9/1997 | Villalta et al. |
| 5,681,265 A | 10/1997 | Maeda et al. |
| 5,702,177 A | 12/1997 | Lin |
| 5,728,046 A | 3/1998 | Mayer et al. |
| 5,728,097 A | 3/1998 | Mathews |
| 5,746,720 A | 5/1998 | Stouder, Jr. |
| 5,755,660 A | 5/1998 | Tyagi |
| 5,762,629 A | 6/1998 | Kambin |
| 5,769,782 A | 6/1998 | Phan |
| 5,772,582 A | 6/1998 | Huttner et al. |
| 5,772,583 A * | 6/1998 | Wright ............... A61B 17/0206 403/389 |
| 5,779,629 A | 7/1998 | Hohlen |
| 5,785,648 A | 7/1998 | Min |
| 5,792,044 A | 8/1998 | Foley et al. |
| 5,795,291 A * | 8/1998 | Koros ................ A61B 17/02 600/213 |
| 5,810,721 A | 9/1998 | Mueller et al. |
| 5,813,978 A | 9/1998 | Jako |
| 5,816,257 A | 10/1998 | Chin |
| 5,827,286 A | 10/1998 | Incavo et al. |
| 5,846,194 A | 12/1998 | Wasson et al. |
| 5,868,668 A | 2/1999 | Weiss |

(56) References Cited

U.S. PATENT DOCUMENTS

| | | |
|---|---|---|
| 5,873,820 A | 2/1999 | Norell |
| 5,875,782 A | 3/1999 | Ferrari et al. |
| 5,879,291 A | 3/1999 | Kolata et al. |
| 5,882,344 A | 3/1999 | Stouder, Jr. |
| 5,885,210 A | 3/1999 | Cox |
| 5,891,147 A | 4/1999 | Moskovitz et al. |
| 5,893,831 A | 4/1999 | Koros et al. |
| 5,897,490 A | 4/1999 | Fox et al. |
| 5,899,854 A | 5/1999 | Slishman |
| 5,899,901 A | 5/1999 | Middleton |
| 5,902,231 A | 5/1999 | Foley et al. |
| 5,902,233 A | 5/1999 | Farley et al. |
| 5,902,315 A | 5/1999 | DuBois |
| 5,928,139 A | 7/1999 | Koros et al. |
| 5,931,777 A | 8/1999 | Sava |
| 5,944,658 A | 8/1999 | Koros et al. |
| 5,947,896 A | 9/1999 | Sherts et al. |
| 5,951,467 A | 9/1999 | Picha et al. |
| 5,954,635 A | 9/1999 | Foley et al. |
| 5,967,970 A | 10/1999 | Cowan et al. |
| 5,967,972 A | 10/1999 | Santilli et al. |
| 5,967,973 A | 10/1999 | Sherts et al. |
| 5,968,098 A | 10/1999 | Winslow |
| 5,976,146 A | 11/1999 | Ogawa et al. |
| 5,981,147 A | 11/1999 | Hallock et al. |
| 5,984,867 A | 11/1999 | Deckman et al. |
| 6,024,697 A | 2/2000 | Pisarik |
| 6,030,340 A | 2/2000 | Maffei et al. |
| 6,033,406 A | 3/2000 | Mathews |
| 6,042,542 A | 3/2000 | Koros et al. |
| 6,048,309 A | 4/2000 | Flom et al. |
| 6,063,088 A | 5/2000 | Winslow |
| 6,074,343 A | 6/2000 | Nathanson et al. |
| 6,083,154 A | 7/2000 | Liu et al. |
| 6,090,043 A | 7/2000 | Austin et al. |
| 6,090,113 A | 7/2000 | Le Couedic et al. |
| 6,113,535 A | 9/2000 | Fox et al. |
| 6,120,434 A | 9/2000 | Kimura et al. |
| 6,139,493 A * | 10/2000 | Koros ............... A61B 17/0206 600/213 |
| 6,142,935 A | 11/2000 | Flom et al. |
| 6,152,871 A | 11/2000 | Foley et al. |
| 6,159,179 A | 12/2000 | Simonson |
| 6,162,170 A | 12/2000 | Foley et al. |
| 6,174,282 B1 | 1/2001 | Tan |
| 6,176,823 B1 | 1/2001 | Foley et al. |
| 6,176,824 B1 | 1/2001 | Davis |
| 6,187,000 B1 | 2/2001 | Davison et al. |
| 6,196,969 B1 | 3/2001 | Bester et al. |
| 6,197,002 B1 | 3/2001 | Peterson |
| 6,200,263 B1 | 3/2001 | Person |
| 6,200,324 B1 | 3/2001 | Regni, Jr. |
| 6,206,822 B1 | 3/2001 | Foley et al. |
| 6,206,862 B1 | 3/2001 | Giamanco et al. |
| 6,217,509 B1 | 4/2001 | Foley et al. |
| 6,224,545 B1 | 5/2001 | Cocchia et al. |
| 6,224,608 B1 | 5/2001 | Ciccolella et al. |
| 6,241,659 B1 | 6/2001 | Bookwalter et al. |
| 6,261,295 B1 | 7/2001 | Nicholson et al. |
| 6,264,650 B1 | 7/2001 | Hovda et al. |
| 6,267,763 B1 | 7/2001 | Castro |
| 6,277,094 B1 | 8/2001 | Schendel |
| 6,280,379 B1 | 8/2001 | Resnick |
| 6,287,251 B1 | 9/2001 | Tan |
| 6,293,950 B1 | 9/2001 | Lynch et al. |
| 6,306,170 B2 | 10/2001 | Ray |
| 6,322,500 B1 | 11/2001 | Sikora et al. |
| 6,331,157 B2 | 12/2001 | Hancock |
| 6,338,712 B2 * | 1/2002 | Spence et al. ............... 600/201 |
| 6,342,036 B1 | 1/2002 | Cooper et al. |
| 6,371,959 B1 | 4/2002 | Trice |
| 6,371,968 B1 | 4/2002 | Kogasaka et al. |
| 6,394,950 B1 | 5/2002 | Weiss |
| 6,395,007 B1 | 5/2002 | Bhatnagar et al. |
| 6,416,465 B2 | 7/2002 | Brau |
| 6,416,468 B2 | 7/2002 | Deckman et al. |
| 6,427,034 B1 | 7/2002 | Meis et al. |
| 6,428,473 B1 * | 8/2002 | Leonard et al. ............... 600/219 |
| 6,428,474 B1 | 8/2002 | Weiss |
| 6,431,025 B1 | 8/2002 | Koros et al. |
| 6,432,049 B1 | 8/2002 | Banta et al. |
| 6,436,033 B1 | 8/2002 | Tan |
| 6,450,952 B1 | 9/2002 | Rioux et al. |
| 6,461,330 B1 | 10/2002 | Miyagi |
| 6,464,634 B1 | 10/2002 | Fraser |
| 6,468,207 B1 | 10/2002 | Fowler, Jr. |
| 6,520,907 B1 | 2/2003 | Foley et al. |
| 6,527,466 B1 | 3/2003 | Blier et al. |
| 6,530,880 B2 | 3/2003 | Pagliuca |
| 6,530,883 B2 | 3/2003 | Bookwalter et al. |
| 6,530,926 B1 | 3/2003 | Davison |
| 6,537,212 B2 | 3/2003 | Sherts et al. |
| 6,591,049 B2 | 7/2003 | Williams et al. |
| 6,592,582 B2 | 7/2003 | Hess et al. |
| 6,593,394 B1 | 7/2003 | Li et al. |
| 6,595,917 B2 | 7/2003 | Nieto |
| 6,599,292 B1 | 7/2003 | Ray |
| 6,616,605 B2 | 9/2003 | Wright et al. |
| 6,639,965 B1 | 10/2003 | Hsieh et al. |
| 6,656,176 B2 | 12/2003 | Hess et al. |
| 6,659,945 B2 | 12/2003 | Ball et al. |
| 6,679,833 B2 | 1/2004 | Smith et al. |
| 6,689,054 B2 | 2/2004 | Furnish et al. |
| 6,692,434 B2 | 2/2004 | Ritland |
| 6,702,741 B2 | 3/2004 | Rioux et al. |
| 6,712,825 B2 | 3/2004 | Aebi et al. |
| 6,716,218 B2 | 4/2004 | Holmes et al. |
| 6,723,043 B2 | 4/2004 | Kleeman et al. |
| 6,729,205 B2 | 5/2004 | Phillips |
| 6,733,445 B2 | 5/2004 | Sherts et al. |
| 6,740,102 B2 | 5/2004 | Hess et al. |
| 6,755,839 B2 | 6/2004 | Van Hoeck et al. |
| 6,764,444 B2 | 7/2004 | Wu et al. |
| 6,793,656 B1 | 9/2004 | Mathews |
| 6,814,700 B1 | 11/2004 | Mueller et al. |
| 6,830,547 B2 | 12/2004 | Weiss |
| 6,869,398 B2 | 3/2005 | Obenchain et al. |
| 6,893,394 B2 | 5/2005 | Douglas et al. |
| 6,896,680 B2 | 5/2005 | Michelson |
| 6,929,606 B2 | 8/2005 | Ritland |
| 6,939,297 B2 | 9/2005 | Gannoe et al. |
| 6,945,933 B2 | 9/2005 | Branch et al. |
| 6,951,538 B2 | 10/2005 | Ritland |
| 6,982,740 B2 | 1/2006 | Adair et al. |
| 7,008,432 B2 | 3/2006 | Schlapfer et al. |
| 7,052,497 B2 | 5/2006 | Sherman et al. |
| 7,074,226 B2 | 7/2006 | Roehm, III et al. |
| 7,081,118 B2 | 7/2006 | Weber et al. |
| 7,087,055 B2 | 8/2006 | Lim et al. |
| 7,097,647 B2 | 8/2006 | Segler |
| 7,141,015 B2 | 11/2006 | Ruane |
| 7,150,714 B2 | 12/2006 | Myles |
| 7,156,085 B2 | 1/2007 | Lewis et al. |
| 7,156,805 B2 | 1/2007 | Thalgott et al. |
| 7,179,225 B2 | 2/2007 | Shluzas et al. |
| 7,179,261 B2 | 2/2007 | Sicvol et al. |
| 7,198,598 B2 | 4/2007 | Smith et al. |
| 7,207,949 B2 | 4/2007 | Miles et al. |
| 7,223,233 B2 | 5/2007 | Branch et al. |
| 7,250,052 B2 | 7/2007 | Landry et al. |
| 7,261,688 B2 | 8/2007 | Smith et al. |
| 7,264,589 B2 | 9/2007 | Sharratt |
| 7,422,596 B2 | 9/2008 | Therin et al. |
| 7,473,222 B2 | 1/2009 | Dewey et al. |
| 7,481,766 B2 | 1/2009 | Lee et al. |
| 7,491,168 B2 | 2/2009 | Raymond et al. |
| 7,491,208 B2 | 2/2009 | Pond, Jr. et al. |
| 7,513,869 B2 | 4/2009 | Branch et al. |
| 7,524,285 B2 | 4/2009 | Branch et al. |
| 7,556,601 B2 | 7/2009 | Branch et al. |
| 7,918,792 B2 | 4/2011 | Drzyzga et al. |
| 7,955,257 B2 | 6/2011 | Frasier et al. |
| 7,976,463 B2 | 7/2011 | Dewey et al. |
| 7,981,029 B2 | 7/2011 | Branch et al. |

(56) References Cited

U.S. PATENT DOCUMENTS

| | | |
|---|---|---|
| 7,981,031 B2 | 7/2011 | Frasier et al. |
| 8,038,611 B2 | 10/2011 | Raymond et al. |
| 8,602,984 B2 | 12/2013 | Raymond et al. |
| 8,622,897 B2 | 1/2014 | Raymond et al. |
| 2001/0009971 A1 | 7/2001 | Sherts et al. |
| 2001/0029377 A1 | 10/2001 | Aebi et al. |
| 2001/0031969 A1 | 10/2001 | Aebi et al. |
| 2002/0002324 A1 | 1/2002 | McManus |
| 2002/0013514 A1 | 1/2002 | Brau |
| 2002/0022764 A1 | 2/2002 | Smith et al. |
| 2002/0026101 A1 | 2/2002 | Bookwalter et al. |
| 2002/0055670 A1 | 5/2002 | Weiss |
| 2002/0058948 A1 | 5/2002 | Arlettaz |
| 2002/0080248 A1 | 6/2002 | Adair et al. |
| 2002/0095070 A1 | 7/2002 | Furnish et al. |
| 2002/0123754 A1 | 9/2002 | Holmes et al. |
| 2002/0128659 A1 | 9/2002 | Michelson |
| 2002/0143235 A1 | 10/2002 | Pagliuca |
| 2002/0169363 A1 | 11/2002 | Herold |
| 2002/0193666 A1 | 12/2002 | Sherts et al. |
| 2003/0004401 A1 | 1/2003 | Ball et al. |
| 2003/0060687 A1 | 3/2003 | Kleeman et al. |
| 2003/0149341 A1 | 8/2003 | Clifton |
| 2003/0163030 A1 | 8/2003 | Arriaga |
| 2003/0176772 A1 | 9/2003 | Yang |
| 2003/0191371 A1 | 10/2003 | Smith et al. |
| 2003/0220650 A1 | 11/2003 | Major et al. |
| 2003/0225408 A1 | 12/2003 | Nichols et al. |
| 2004/0002629 A1* | 1/2004 | Branch ............. A61B 17/0206 600/210 |
| 2004/0034351 A1 | 2/2004 | Sherman et al. |
| 2004/0039247 A1 | 2/2004 | Weber et al. |
| 2004/0059339 A1 | 3/2004 | Roehm et al. |
| 2004/0087833 A1 | 5/2004 | Bauer et al. |
| 2004/0138662 A1 | 7/2004 | Landry et al. |
| 2004/0141302 A1 | 7/2004 | Koch et al. |
| 2004/0141336 A1 | 7/2004 | West et al. |
| 2004/0143167 A1 | 7/2004 | Branch et al. |
| 2004/0143169 A1 | 7/2004 | Branch et al. |
| 2004/0230191 A1 | 11/2004 | Frey et al. |
| 2004/0242969 A1 | 12/2004 | Sherts et al. |
| 2005/0015096 A1 | 1/2005 | Oliver |
| 2005/0043592 A1 | 2/2005 | Boyd et al. |
| 2005/0080320 A1 | 4/2005 | Lee et al. |
| 2005/0131422 A1 | 6/2005 | Anderson et al. |
| 2005/0137461 A1 | 6/2005 | Marchek et al. |
| 2005/0159650 A1 | 7/2005 | Raymond et al. |
| 2005/0159651 A1 | 7/2005 | Raymond et al. |
| 2005/0171551 A1 | 8/2005 | Sukovich et al. |
| 2005/0215866 A1 | 9/2005 | Kim |
| 2005/0243592 A1 | 11/2005 | Rust et al. |
| 2005/0267336 A1 | 12/2005 | Bertolero et al. |
| 2005/0273133 A1 | 12/2005 | Shluzas et al. |
| 2006/0004401 A1 | 1/2006 | Abernathie et al. |
| 2006/0069315 A1 | 3/2006 | Miles et al. |
| 2006/0074278 A1 | 4/2006 | Petit et al. |
| 2006/0084844 A1 | 4/2006 | Nehls |
| 2006/0195017 A1 | 8/2006 | Shluzas et al. |
| 2006/0207612 A1 | 9/2006 | Jackson et al. |
| 2006/0224044 A1 | 10/2006 | Marchek et al. |
| 2006/0247651 A1 | 11/2006 | Roehm et al. |
| 2006/0285339 A1 | 12/2006 | Frasier |
| 2007/0038033 A1 | 2/2007 | Jones et al. |
| 2007/0060794 A1 | 3/2007 | Efinger et al. |
| 2007/0060795 A1 | 3/2007 | Vayser et al. |
| 2007/0100212 A1 | 5/2007 | Pimenta et al. |
| 2007/0106123 A1 | 5/2007 | Gorek et al. |
| 2007/0118022 A1 | 5/2007 | Hutton |
| 2007/0156023 A1 | 7/2007 | Frasier et al. |
| 2007/0156024 A1 | 7/2007 | Frasier et al. |
| 2007/0156025 A1 | 7/2007 | Marchek et al. |
| 2007/0156026 A1 | 7/2007 | Frasier et al. |
| 2007/0208227 A1 | 9/2007 | Smith et al. |
| 2007/0208228 A1 | 9/2007 | Pavento et al. |
| 2008/0021285 A1 | 1/2008 | Drzyzga et al. |
| 2008/0097164 A1 | 4/2008 | Miles et al. |
| 2009/0015879 A1 | 1/2009 | Nose et al. |
| 2009/0018399 A1 | 1/2009 | Martinelli et al. |
| 2009/0018400 A1 | 1/2009 | Raymond et al. |
| 2009/0203967 A1 | 8/2009 | Branch et al. |
| 2011/0004067 A1 | 1/2011 | Marchek et al. |
| 2011/0245621 A1 | 10/2011 | Frasier et al. |
| 2011/0313256 A1 | 12/2011 | Raymond et al. |

FOREIGN PATENT DOCUMENTS

| | | |
|---|---|---|
| EP | 698374 A2 | 2/1996 |
| EP | 0908140 A1 | 4/1999 |
| EP | 0931509 A1 | 7/1999 |
| EP | 1090586 A2 | 4/2001 |
| EP | 1090589 A1 | 4/2001 |
| EP | 1192905 A1 | 4/2002 |
| EP | 1195141 A2 | 4/2002 |
| EP | 1 512 367 A1 | 3/2005 |
| EP | 1 659 928 A2 | 5/2006 |
| EP | 1 727 477 A1 | 12/2006 |
| FR | 2807313 A1 | 10/2001 |
| GB | 1206277 A | 9/1970 |
| JP | 2198764 A | 9/1970 |
| JP | 1014927 | 1/1998 |
| WO | 9001298 A1 | 2/1990 |
| WO | 92/21279 A1 | 12/1992 |
| WO | 93/20741 A1 | 10/1993 |
| WO | 9602195 A1 | 2/1996 |
| WO | 96/28083 A1 | 9/1996 |
| WO | 98/11818 A1 | 3/1998 |
| WO | 98/12961 A1 | 4/1998 |
| WO | 9817208 A2 | 4/1998 |
| WO | 99/12466 A1 | 3/1999 |
| WO | 99/53829 A1 | 10/1999 |
| WO | 00/18306 A1 | 4/2000 |
| WO | 0180725 A1 | 11/2001 |
| WO | 02/060330 A1 | 8/2002 |
| WO | 04000140 A1 | 12/2003 |
| WO | 2005096735 A2 | 10/2005 |

OTHER PUBLICATIONS

Mayer, H., M., M.D., "A new Microsurgical Technique for Minimally Invasive Anterior Lumbar Interbody Fusion"; Spine; vol. 22(6); 1997; pp. 691-700.

* cited by examiner

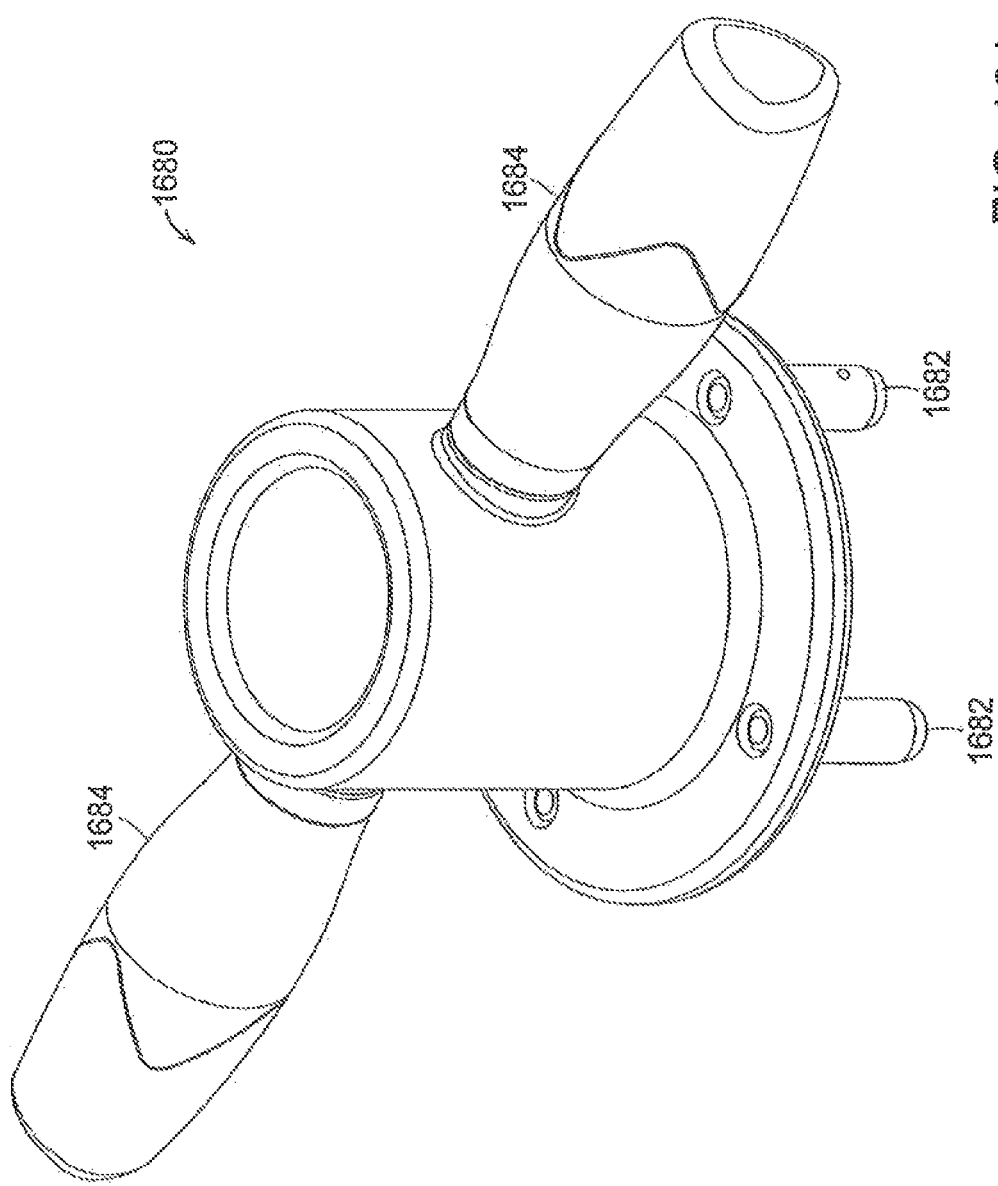

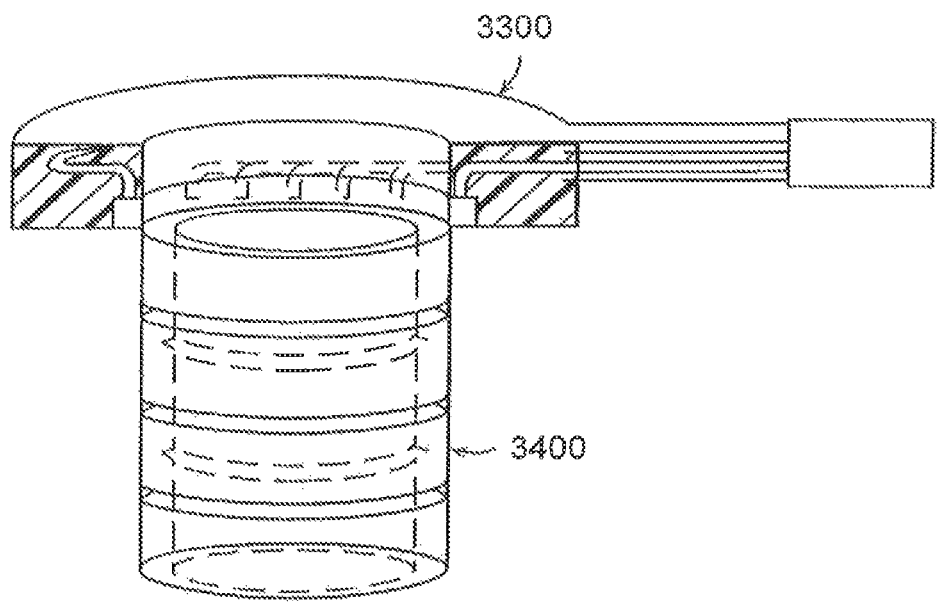
FIG. 36
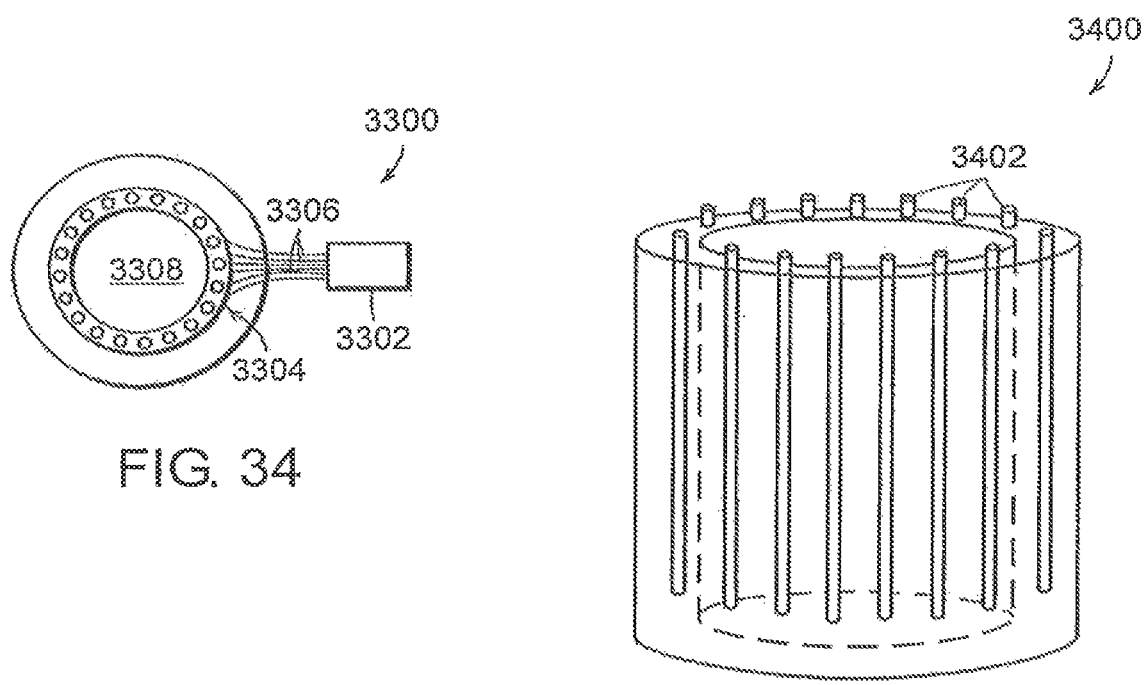
FIG. 34
FIG. 35

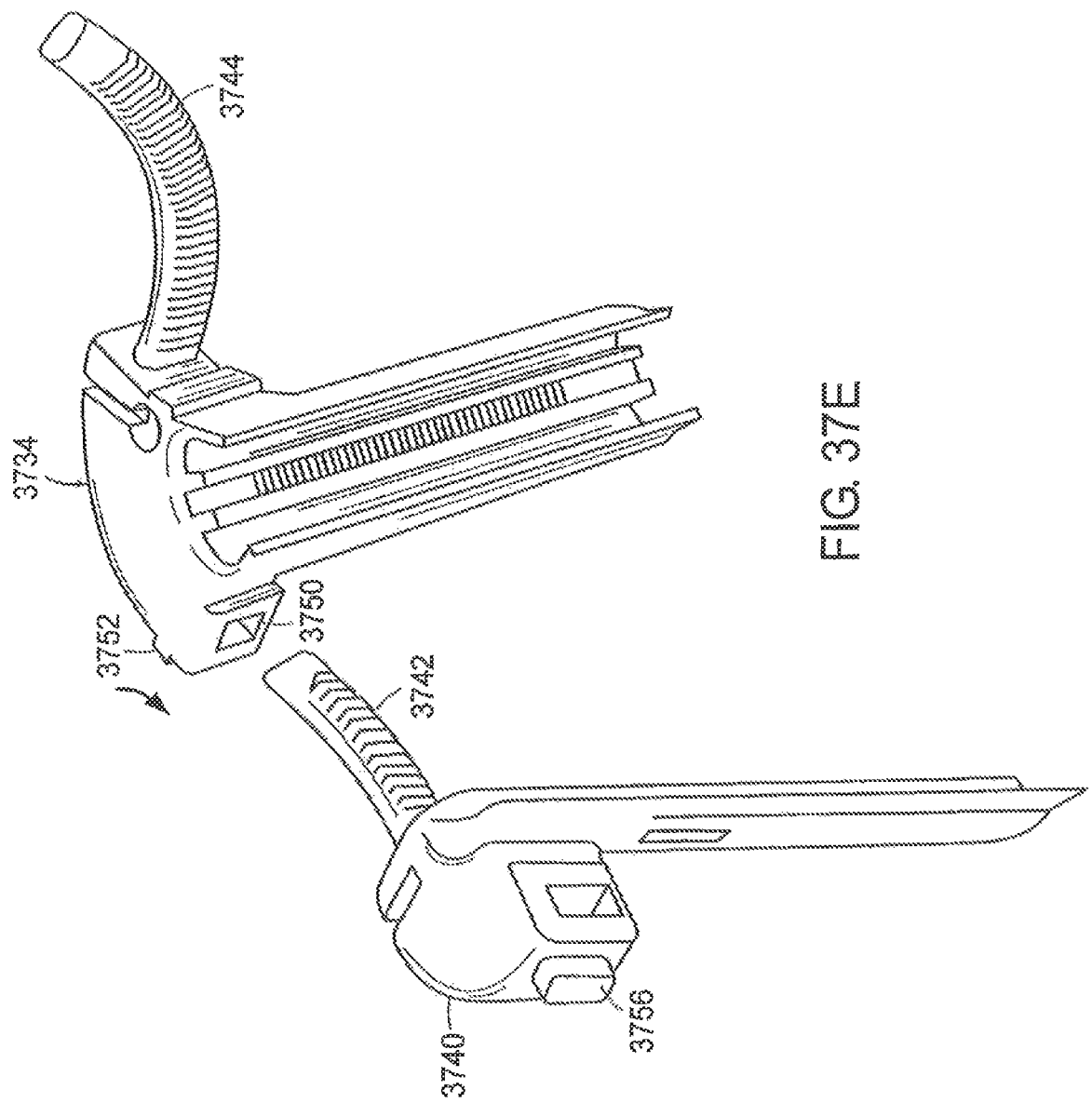

SURGICAL RETRACTOR SYSTEMS AND ILLUMINATED CANNULAE

REFERENCE TO RELATED APPLICATIONS

This application is continuation of U.S. application Ser. No. 12/241,963, filed Sep. 30, 2008, entitled "Surgical Retractor Systems and Illuminated Cannulae", which is a continuation of U.S. application Ser. No. 11/016,347, filed Dec. 17, 2004, now issued as U.S. Pat. No. 7,491,168, on Feb. 17, 2009, which claims priority to U.S. Provisional Patent Application No. 60/530,565, filed on Dec. 18, 2003, each of which are incorporated herein by reference.

BACKGROUND

In surgical procedures, it is preferable to minimize or reduce trauma to the patient and damage to tissue. To achieve this result, surgeons try to keep incisions as small as possible. However, it is usually necessary that the surgeon have a clear view of the operating field.

A variety of retractors are available to keep an incision open and provide a clear view of the operating field. Retractors are used in surgical operations to reposition muscular tissue, vessels, nerves, and other tissue with the aid of retractor blades, thereby providing access to the site of the operation. Surgical refractors are particularly important in performing surgical procedures that involve the spinal column, where access to the surgical sight can be obtained, for example, through a posterior, posterior-lateral, anterior, lateral, or an anterior-lateral approach.

In some embodiments, a step-wise dilation of the surgical incision can be performed to gradually dilate the muscles and tissues to the required size to insert the retractor. Step-wise dilation can involve the use of a series of dilators or cannulae with successively larger diameters. This method involves first inserting the smallest dilator or cannula into an incision. Then a second dilator or cannula, with a slightly larger diameter, is slid over the smaller dilator or cannula and into the incision, thereby causing the incision to expand to the slightly larger diameter of the second dilator or cannula. This process can be repeated using a series of dilators or cannulae with successively larger diameters, until the incision is large enough to allow for insertion of the retractor. Once positioned, the retractors produce a small surgical site or window. However, most currently available retractors are large and cumbersome, requiring a long incision length that traumatizes the patient's muscles and tissue.

Therefore a need exists for a retractor that overcomes or minimizes these and other problems.

Disclosed herein are methods and devices that improve surgical procedures by, for example, creating a working space for the procedure and improving the surgical conditions for a practitioner of the procedure.

This invention includes surgical retractors. In some embodiments, the surgical retractor comprises a frame and at least two retractor blades attached to the frame. The frame includes a first base component, a second base component, and a connector. The connector connects the first base component and the second base component, and the first base component and/or the second base component are Moveable, along a length of the connector. Upon movement of the connector relative to the first base component or second base component, the frame moves from a first position to a second position and causes a distance between the first base component and the second base component to change; and In other embodiments, the surgical retractors of the invention comprise a first retractor blade, a second retractor blade, a third retractor blade, a fourth retractor blade, a first connector, and a second connector. The first connector is assembled to a proximal end of the first retractor blade and a proximal end of the second retractor blade, and the first retractor blade and/or the second refractor blade is movable along a line that is parallel to a length of the first connector. The second connector is assembled to a proximal end of the third retractor blade and a proximal end of the fourth retractor blade, and the third retractor blade and/or the fourth retractor blade is movable along a line that is parallel to a length of the second connector. The first connector and/or the second connector is movable along a line that intersects the first connector and the second connector.

In another embodiment, this invention includes an assembly comprising a surgical refractor (e.g., a surgical retractor of the invention) assembled to an obtruator.

In yet more embodiments, the surgical retractors of the invention comprise a housing component having a central axis and a cylindrical expander component. The housing component includes a cylindrical portion and a blade portion. The cylindrincal portion defines a conduit having an inner diameter normal to the central axis. The blade portion is contiguous with one end of the cylindrical portion and includes at least two blades. A distal portion of each blade is moveable relative to the central axis. In a first position, the distal ends of the blade portion are proximate, and upon movement of the distal portion of the blades relative to the central axis, the blades move from a first position to a second position and form a conduit down the length of the central axis. The cylindrical expander portion has an outer diameter that is smaller than the inner diameter of the cylindrical portion and the expander component is movably attached to the housing component.

In still more embodiments, this invention includes an illuminated surgical cannula comprising a surgical cannula and an interface ring. The surgical cannula has an outer diameter, an inner diameter, a distal end, and a proximal end, wherein an interior area is defined by the inner diameter, the distal end, and the proximal end. The interface ring is attached to the proximal end and includes a light source interface in photonic communication with an array of fiber optic wire. The array is arranged to direct light towards the distal end of the cannula.

In yet further embodiments, this invention includes surgical methods. The methods comprise incising tissue of a mammal to create an incision, expanding the incision to create a pathway from the incision to a surgical site, directing a retractor (e.g., a retractor of the invention) into the pathway, creating a working channel through the retractor by separating at least two retractor blades, and performing at least a portion of a surgical procedure through the working channel. In some embodiments of the invention, the pathway extends to a first vertebra and at least a portion of the surgical procedure is performed at the first vertebra, and the method further includes directing an instrument or implant between at least two retractor blades to access a second vertebra adjacent to the first vertebra. In still further embodiments, the retract& is expanded by separating a first retractor blade from a second retractor blade by moving at least one of the first retractor blade and the second retractor blade along an first connector of the retractor and separating a third retractor blade from a fourth retractor blade by moving at least one of the third retractor blade and the fourth retractor blade along a second connector, wherein the second connector is oriented at an angle to the first connector.

The retractors of this invention can be inserted into a body with the ease of a tubular-haled system (e.g., a step-wise dilation system), while allowing the surgeon to further retract tissue and muscle once the retractor is located at its fixed position in the body. This invention allows the insertion of a retractor with either step-wise dilation of a minimally invasive incision (e.g., a stab incision), by, for example, inserting the retractor over one or more dilators or without step-wise dilation of the incision by, for example, inserting the retractor through an open incision or through a minimally invasive incision that is expanded by methods other than sequential dilation. The invention provides methods and devices that reduce the invasiveness and trauma associated with surgical procedures. The illuminated cannula of this invention eliminate the need for light sources that restrict the working space.

BRIEF DESCRIPTION OF THE DRAWINGS

FIG. 16A-16M illustrates another embodiment of a retractor of the invention.

FIG. 34 illustrates one embodiment of an interface ring.

FIG. 35 illustrates a portion of one embodiment of a cannula of the invention,

FIG. 36 illustrates the interface ring of FIG. 34 assembled to a portion of the cannula of FIG. 35.

DETAILED DESCRIPTION OF THE INVENTION

Figure 1:
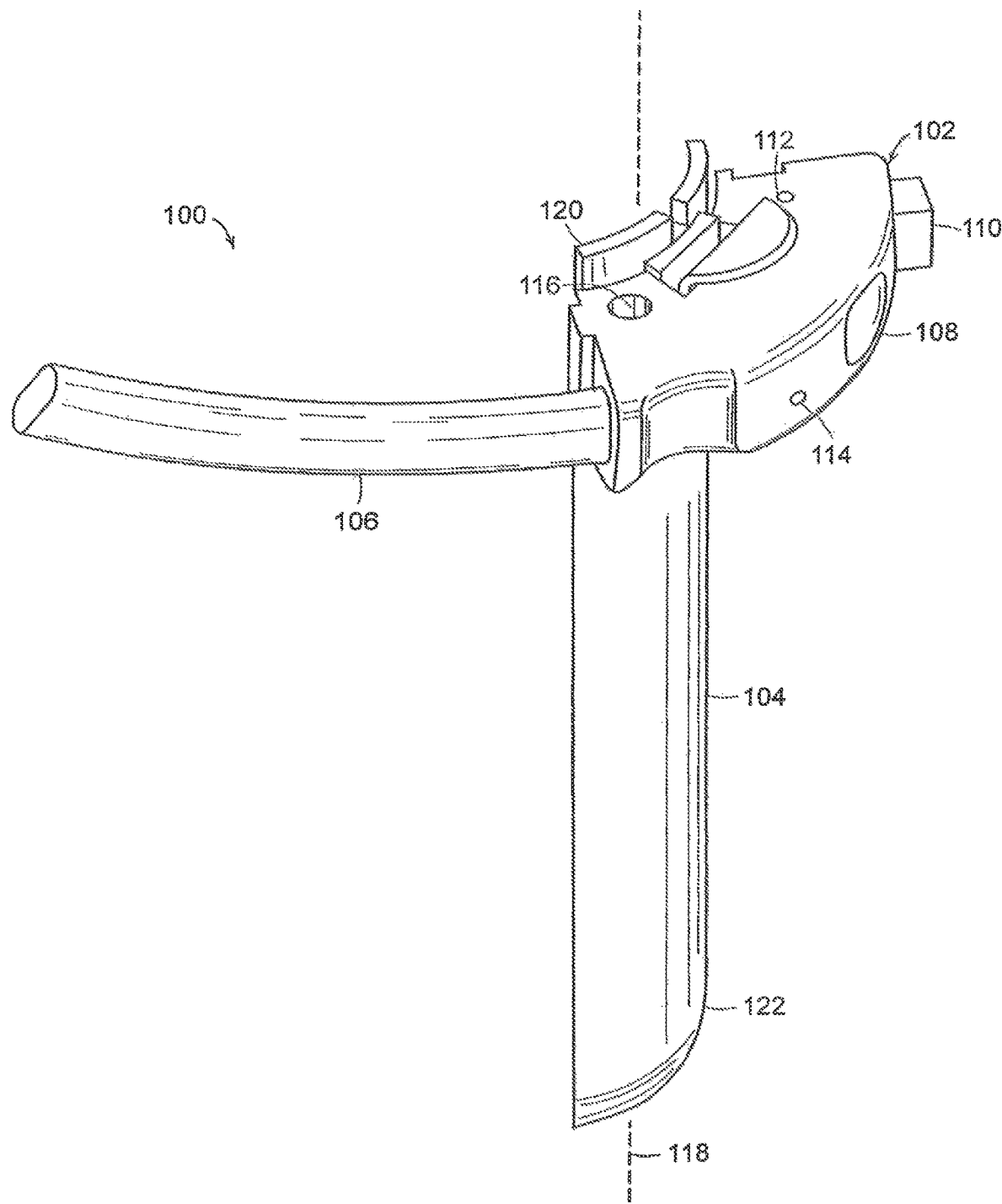
FIG. 1 illustrates a view of a portion of one embodiment of a retractor of the invention.

A description of preferred embodiments of the invention follows. While this invention has been particularly shown and described with references to preferred embodiments thereof, it will be understood by those skilled in the art that various changes in form and details may be made without departing from the scope of the invention encompassed by the appended claims.

This invention includes surgical retractors that provide a surgical site. In some embodiments, the surgical retractor comprises an expandable frame attached to at least two retractor blades.

In some embodiments, the retractors include an expandable frame. The expandable frame includes two or more base components and at least one connector that connects the base components (e.g., 3, 4, 5, 6, 7, 8, or more than 8 base components and/or connectors). At least two of the base components are connected by one or more connectors (e.g., a ratchet arm or a hinge) that are moveable relative to at least one base component.

Upon movement of the connector relative to at least one base component, the expandable frame moves from a first position to a second position, thereby causing an average distance between the base components to increase or decrease (i.e., the expandable base expands or contracts). Moving the connectors relative to at least one base component causes the expandable frame to move from a first position to a second position, thereby causing an average distance between the base components to increase or decrease. Moving the same, or another, connector relative to the same, or another, base component causes the expandable frame to move from the second position to a third position or back to the first position, thereby causing the average distance between the base components to increase or decrease.

As used herein, the terms "first position," "second position," and "third position" are used to merely refer to dissimilar positions and are not meant to imply that all embodiments of the expandable frame can only be adjusted to one, two, or three positions. In some embodiments, the expandable frame is adjustable to a finite number of positions. In other embodiments, the distance between one or more base components can be increased or decreased to any desired extent, thereby allowing the expandable frame to adjust to an almost infinite number of positions.

In some embodiments, the expandable frame has a major plane. In further embodiments, the base components of the expandable frame are moveable along the connector in the major plane or a plane parallel to the major plane.

In some embodiments, the expandable frame includes at least one pair of base components and at least one connector. Each pair includes a first base component, a second base component, at least one connector extending from the first base component, and at least one connector extending from the second base component. The connector extending from each first base component is in movable relation to each second base component and such relative movement causes movement of the first base component relative to the second base component. In some embodiments, the connector extending from the second base component is in moveable relation to another base component. In further embodiments, the movement of one connector relative to a base component is independent of movement of another connector relative to another base component of the expandable frame.

The connector extends between two or more base components and are in moveable relation to at least one base component, Examples of connectors include ratchet arms, hinges, screws, gears (e.g., worm gears), tongue-and-groove connectors, slots, pins, telescoping tubes, or similar connecting devices. Optionally, the expandable frame includes one or more connectors (e.g., ratchet arms) that are arcuate or curved. In some embodiments, arcuate connectors cause the expandable frame to have a substantially circular or elliptical shape during movement from one position to another (e.g., from a first position to a second position). In other embodiments, the expandable frame includes one or more connectors (e.g., ratchet arms) that are straight.

In some embodiments, the expandable frame includes one or more mechanisms for fixing the position of one base component relative to another base component. For example, if the expandable frame has a connector that includes a ratchet arm, one base component may be fixed in position relative to another base component by, for example, a series of interlocking teeth or grooves. In another example, if the expandable frame has a connector that includes a hinge or the like, one base component may be fixed in position relative to another base component by a lever which engages a series of teeth on the hinge, thereby preventing the hinge from rotating, Other exemplary mechanisms for fixing the position of one base component relative to another base component may include hooks, levers, latches, screws, locking mechanisms, combinations thereof, and the like. Additionally, one base component may be fixed in position relative to another base component by, for example, an automated mechanism, such as one or more motorized screws.

Optionally, the expandable frame may include one or more features that facilitate the support of one or more surgical instruments. Examples of surgical instruments include a light source (e.g., a surgical light), a suction device (e.g., a suction tube), a tissue cutting and evacuation instrument (e.g., a device for cutting and removing disk material, such as a pituitary, or a device for cutting and removing bone material, such as a ronguer), or other surgical instruments known in the art.

In some embodiments, at least two retractor blades are attached to the expandable frame, Each refractor blade has an inner face, an outer face, and a major axis running the length of the blade from a proximal end to an opposite distal end. In further embodiments, the outer and/or inner face of one or more of the retractor blades is arcuate in shape.

In some embodiments, the inner face of the retractor blades define a conduit when the expandable frame is at one or more positions. In further embodiments, the conduit is substantially cylindrical or substantially elliptical. Optionally, one or more retractor blades contact each other when the expandable frame is at one or more positions. In still more embodiments, at least some portion of the retractor blades (e.g., the distal ends of one or more blades) provide a surgical site when the expandable frame is at one or more positions (e.g., when the expandable frame is partially or fully expanded). In yet more embodiments, at least some portion of the retractor blades (e.g., the distal ends of one or more blades) provide a surgical site when the expandable frame is fully expanded.

In some embodiments, the outer faces of two or more retractor blades form a thin or relatively narrow blade, which can be useful for inserting the refractor between tissue (e.g., between muscle tissue), when the expandable frame is in at least one position. In further embodiments, the outer faces of two or more refractor blades define a thin or relatively narrow blade while the inner faces define a conduit when the expandable frame is in at least one position.

In some embodiments, the proximal ends of the retractor blades are connected to the expandable frame via a connector. Examples of suitable connectors include clips, hinges, rivets, adhesives, tressits, or the like. In further embodiments, the retractor blade is attached to, and extends from, a base component.

In some embodiments, a retractor blade may be attached to the expandable frame at an angle to the expandable frame (e.g., ~90°, an angle greater than 90°, or an angle lesser than 90°). In further embodiments, the angle at which a retractor blade is attached to an expandable frame may be adjusted.

In some embodiments, one continuous portion of material forms both a base component and one or more additional portions of the retractor (e.g., one or more retractor blades or connectors). For example, a base component and a ratchet arm can be formed from one continuous piece of plastic or metal, thereby reducing the number of pins or other attachment devices needed to attach a ratchet arm to a base component. Examples of suitable materials of construction for the various portions of the retractors of this invention include metals and metal alloys (e.g., stainless steel, aluminum, titanium, nitinol, cobalt chrome, etc.) and/or plastics (e.g., carbon fiber reinforced polymer (CFRP), ultra-high molecular weight polyethylene (UHMWPE), ultem, radel, vectra, polycarbonate, etc.)

In some embodiments, at least one blade is orientated so that the major axis of the blade intersects the major plane of the expandable frame at a non-normal angle. In further embodiments, at least one blade is adjustably connected to the expandable frame so that the angle at which the major axis intersects the major plane can be varied to a desired extent. In still further embodiments, the blade is fixable so as to fix the intersection at a desired angle.

In still more embodiments, at least one blade is rotatable about the major axis of the blade. In a further embodiment, the blade is fixable at a point of rotation about the major axis.

In some embodiments, the base components are arranged to define or form an access portal that provides an opening or window with an inner diameter that allows access to a surgical site when the expandable frame is in at least one position. Upon movement of the expandable frame from a first position to a second position, an inner diameter of the access portal increases or decreases. In some embodiments, the expandable frame can be positioned in a relatively contracted position, thereby reducing the inner diameter and the size of an incision needed to insert the retractor into a mammal. In further embodiments, an average diameter of the access portal is approximately equal to an average diameter between two base components when the expandable frame is in at least one position. In still further embodiments, the access portal is contiguous with a conduit formed by retractor blades when the expandable frame is in at least one position.

In some embodiments, one or more of the blades may include features that facilitate the support of surgical instruments. For example, a surgical instrument (e.g., one or more of the instruments described herein) can be attached along a channel or tract that extends for at least some portion of the length of the blade and is used to guide or position the surgical instrument in or near a surgical site.

Figure 2:
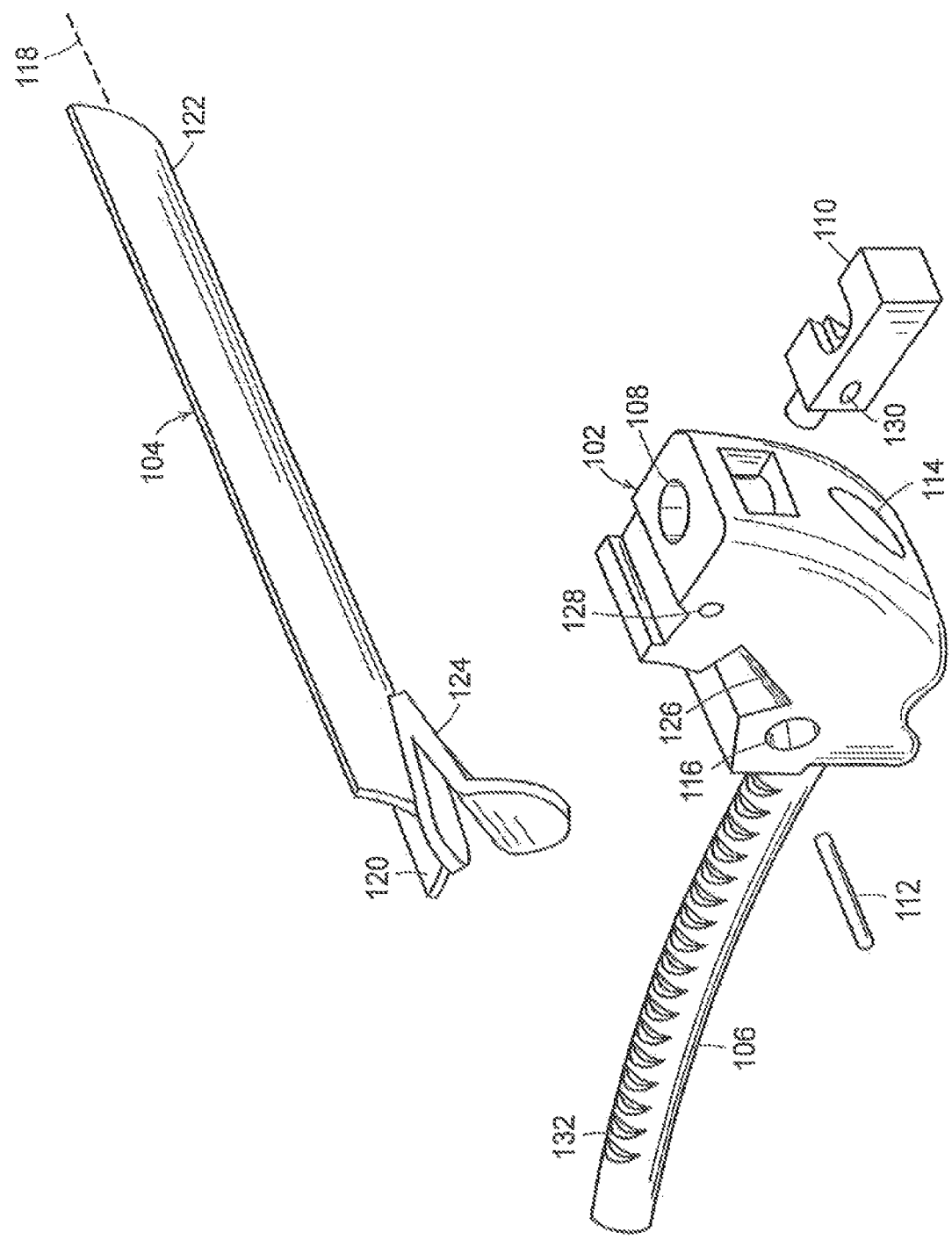
FIG. 2 illustrates a view of a partially disassembled portion of one embodiment of a retractor of the invention.

FIGS. 1 and 2 illustrate two views of a portion of one embodiment of a retractor of the invention. Portion 100 includes base component 102 with attached clip blade 104. Base portion 102 includes portions of a connector that comprises ratchet arm 106 and accommodating hole 108. Portion 100 also includes parts of a mechanism for fixing the position of a first base component relative to a second base component that comprises ratchet release button 110. Ratchet release button 110 and ratchet arm 106 are secured to base component 102 via an attachment mechanism comprising pins 112, 114, respectively. Base component 102 includes an attachment point for supporting surgical instruments that comprises attachment hole 116. Retractor blade 104 has major axis 118 running from proximal end 120 to opposite distal, end 122. Retractor blade 104 includes a blade attachment mechanism that comprises clip 124 that connects proximal end 120 to base component 102. Both the inner and outer face of blade 104 are arcuate along axis 118.

FIG. 2 illustrates partially disassembled portion 100 from an angle dissimilar to that shown in FIG. 1. Clip 124 slides into receptor 126, thereby attaching proximal end 120 of blade 104 to base component 102. Pin 112 is inserted into base 102, via pin hole 128, and passes through channel 130 of ratchet release button 110, thereby securing ratchet release button 110 to base component 102. The view shown in FIG. 2 illustrates teeth 132 running along a portion of the inside length of ratchet arm 106.

In some embodiments, the connector includes a ratchet arm. For example, a ratchet arm attached to a first base component extends through an accommodating hole in another base component, thereby attaching the first and second base components. The second base component can move relative to the ratchet arm, and also move relative to the first base component, by sliding up or down the length of the ratchet arm. The fixing mechanism fixes the position of the ratchet arm at the second base component, thereby immobilizing the first and second base components relative to each other.

Figure 3:
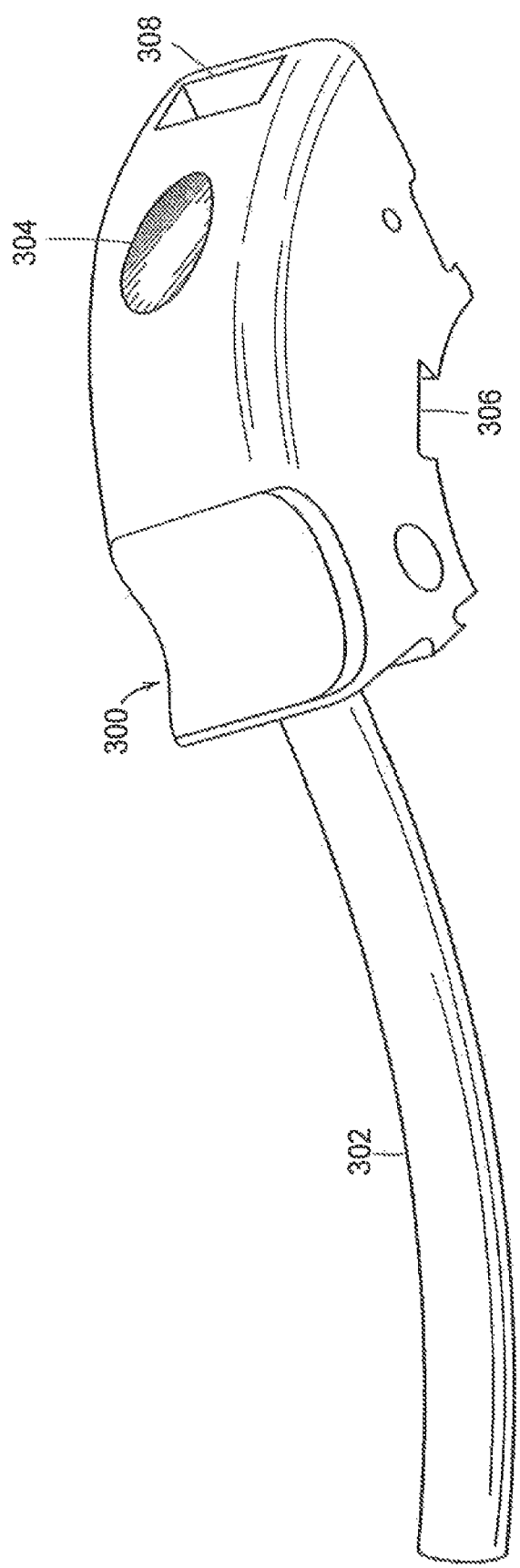
FIG. 3 illustrates a portion of a first base component of one embodiment of the invention.
Figure 4:
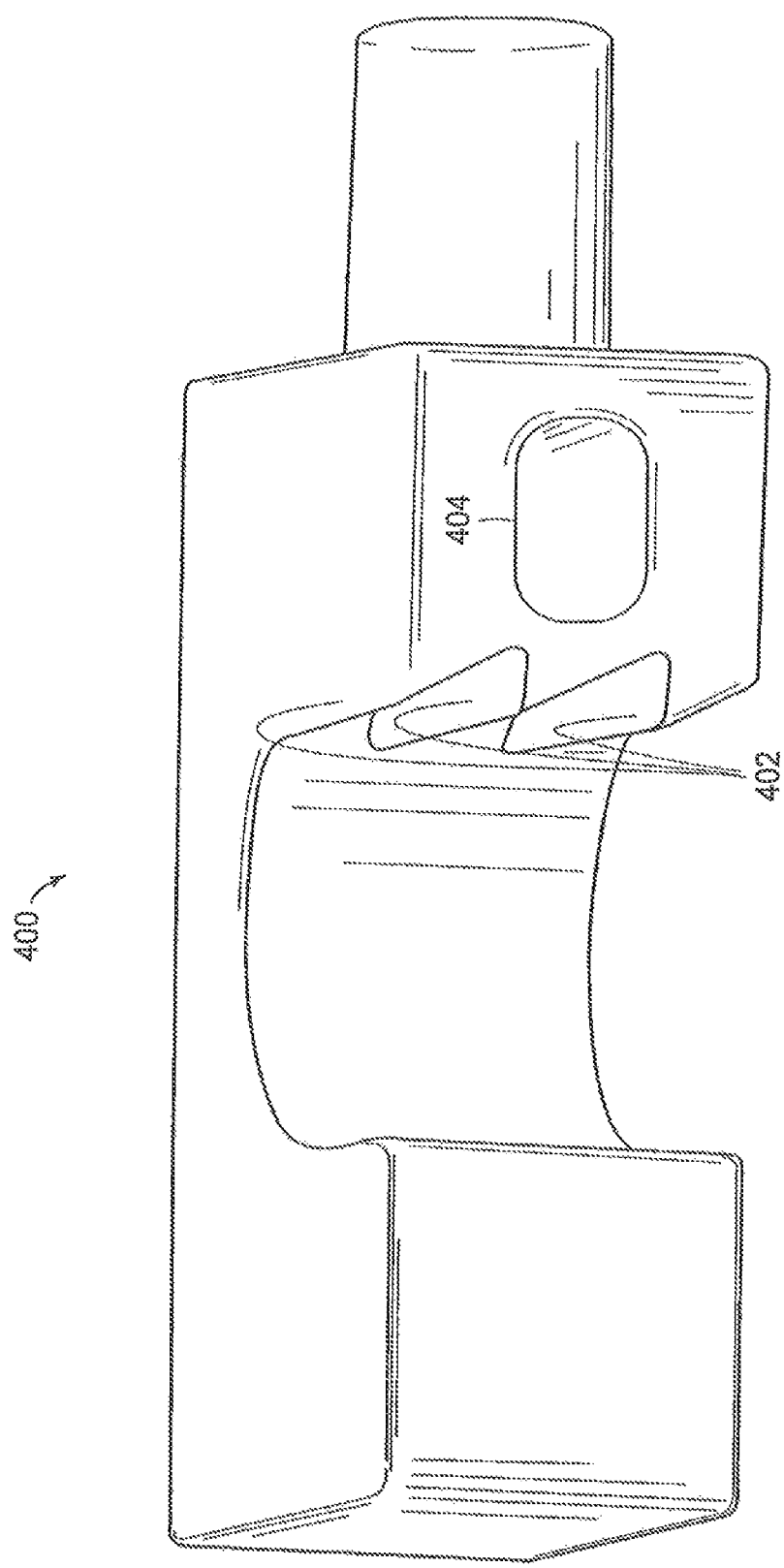
FIG. 4 illustrates a ratchet release button of one embodiment of the invention.
Figure 5:
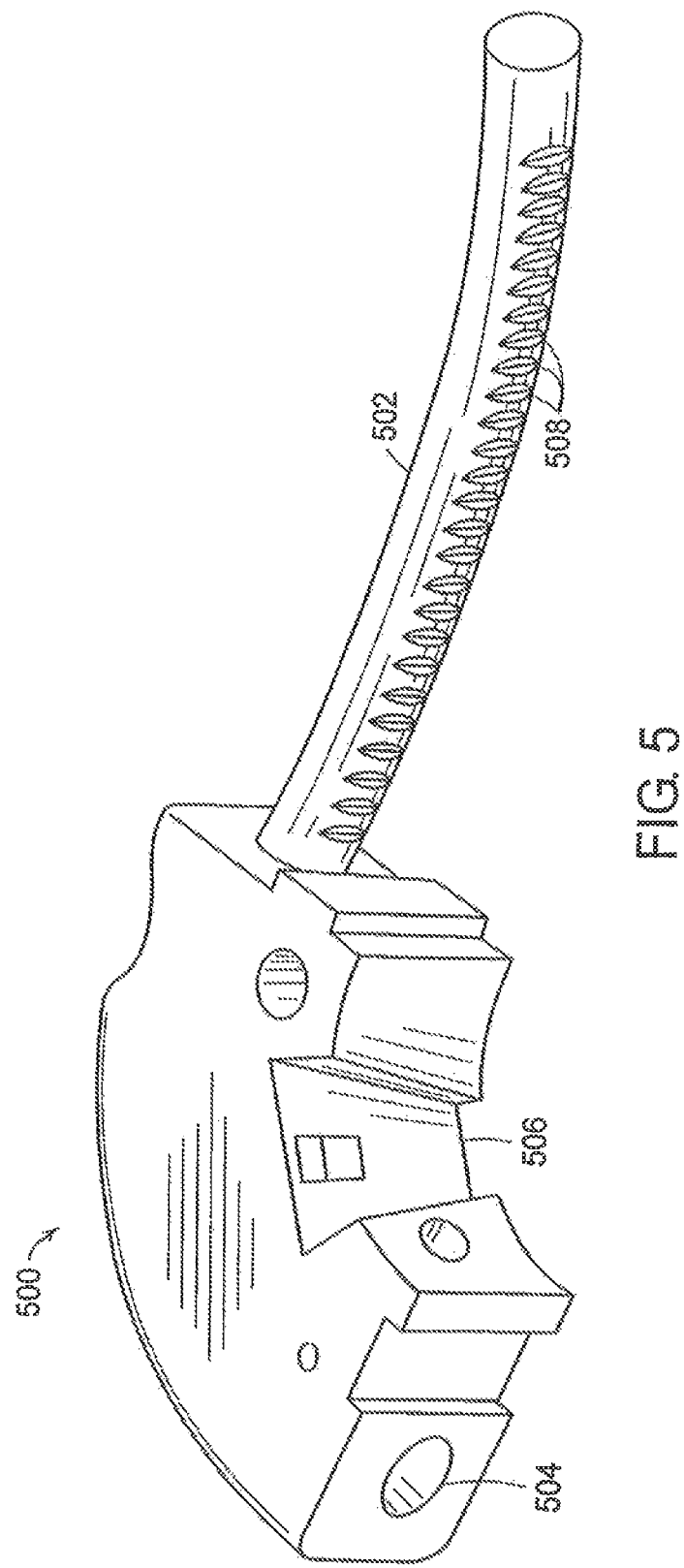
FIG. 5 illustrates a second base component of one embodiment of the invention.

FIGS. 3-5 illustrate various portions of first base component 300, second base component 500, and a mechanism for fixing the position of a first base component relative to a second base component. FIG. 3 illustrates first base component 300 that includes ratchet arm 302, accommodation hole 304, receptor 306, and void 308 which accommodates ratchet release button 400 (illustrated in FIG. 4). Ratchet release button 400 includes teeth 402 and channel 404. FIG. 5 illustrates second base component 500 that includes ratchet arm 502, accommodation hole 504, receptor 506, and teeth 508 on ratchet arm 502. The mechanism for fixing a first base component relative to a second base component comprises teeth 402 and teeth 508, which are complementary to one another. To connect first base component 300 to second base component 500, ratchet arm 502 is directed through accommodation hole 304.

FIG. 4 illustrates ratchet release button 400 of first base component 300. Teeth 402 of ratchet release button 400 are complementary to teeth 508. Teeth 402 and/or teeth 508 can be orientated in such a way that first base component 300 can move down the length of ratchet arm 502 without engaging teeth 402 with teeth 508 when that movement places first base component 300 relatively further from second base component 500. That is, teeth 402 and teeth 505 are orientated such that movement which distances first base component 300 from second base component 500 is relatively unhindered. However, teeth 508 and teeth 402 engage if the relative movement would decrease the distance between first base component 300 and second base component 500. Relative movement of first base component 300 towards second base component 500 is accomplished by pressing ratchet release button 400 to disengage teeth 402 from complementary teeth 508. Once teeth 402 are disengaged from teeth 508, first base component 300 can be moved closer to second base component 500 and to a desired relative position. In some embodiments, the teeth of a ratchet release button and/or the teeth of a ratchet arm are orientated in such a way that they engage, thereby impeding relative movement of one base component away from another. In a further embodiment, the teeth are orientated to impede the relative movement of one base component away from another base component and impede the relative movement of one base component towards another.

Figure 6:
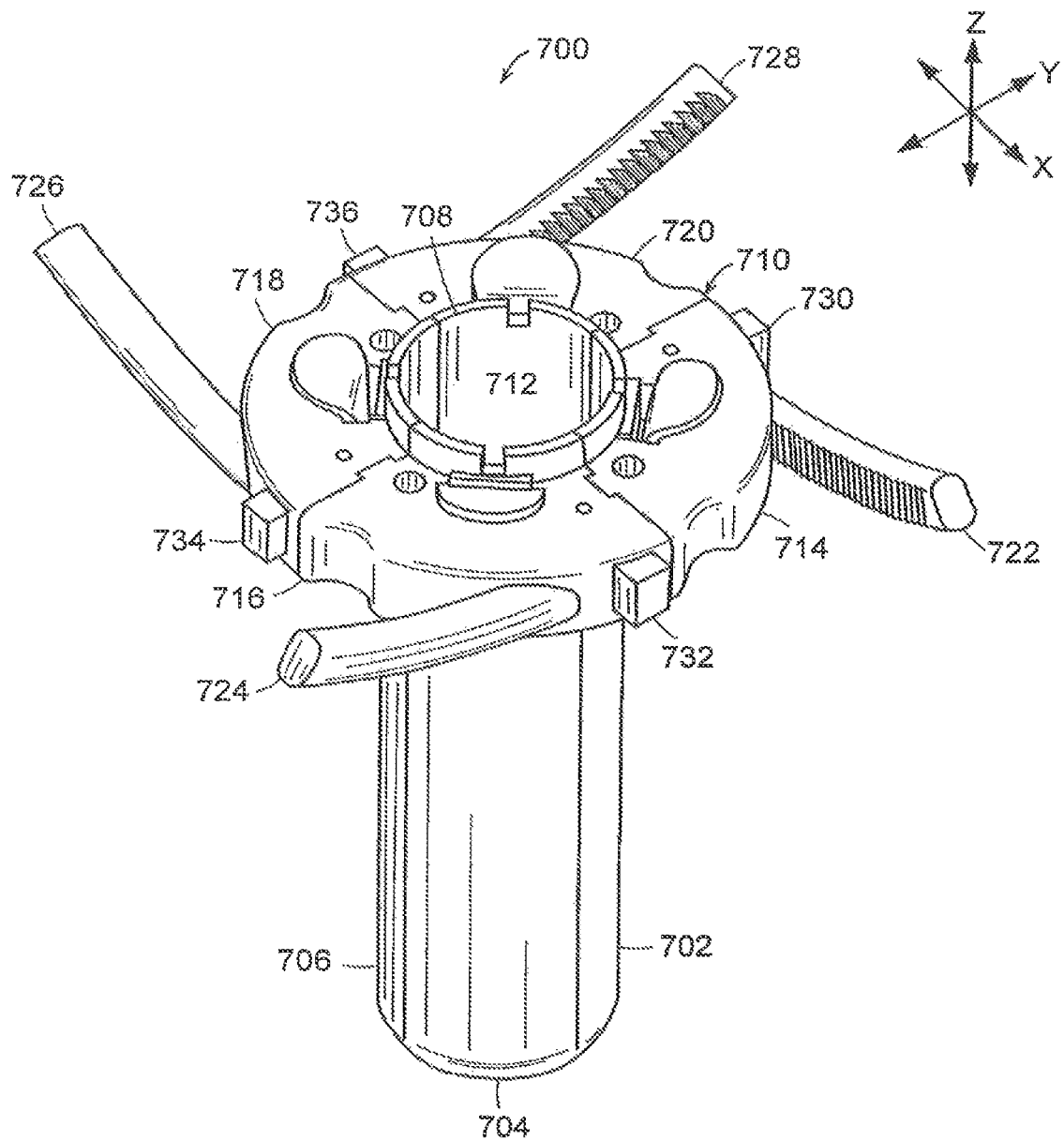
FIGS. 6-8 illustrate one embodiment of a retractor of the invention in three different positions or degrees of expansion.
Figure 7:
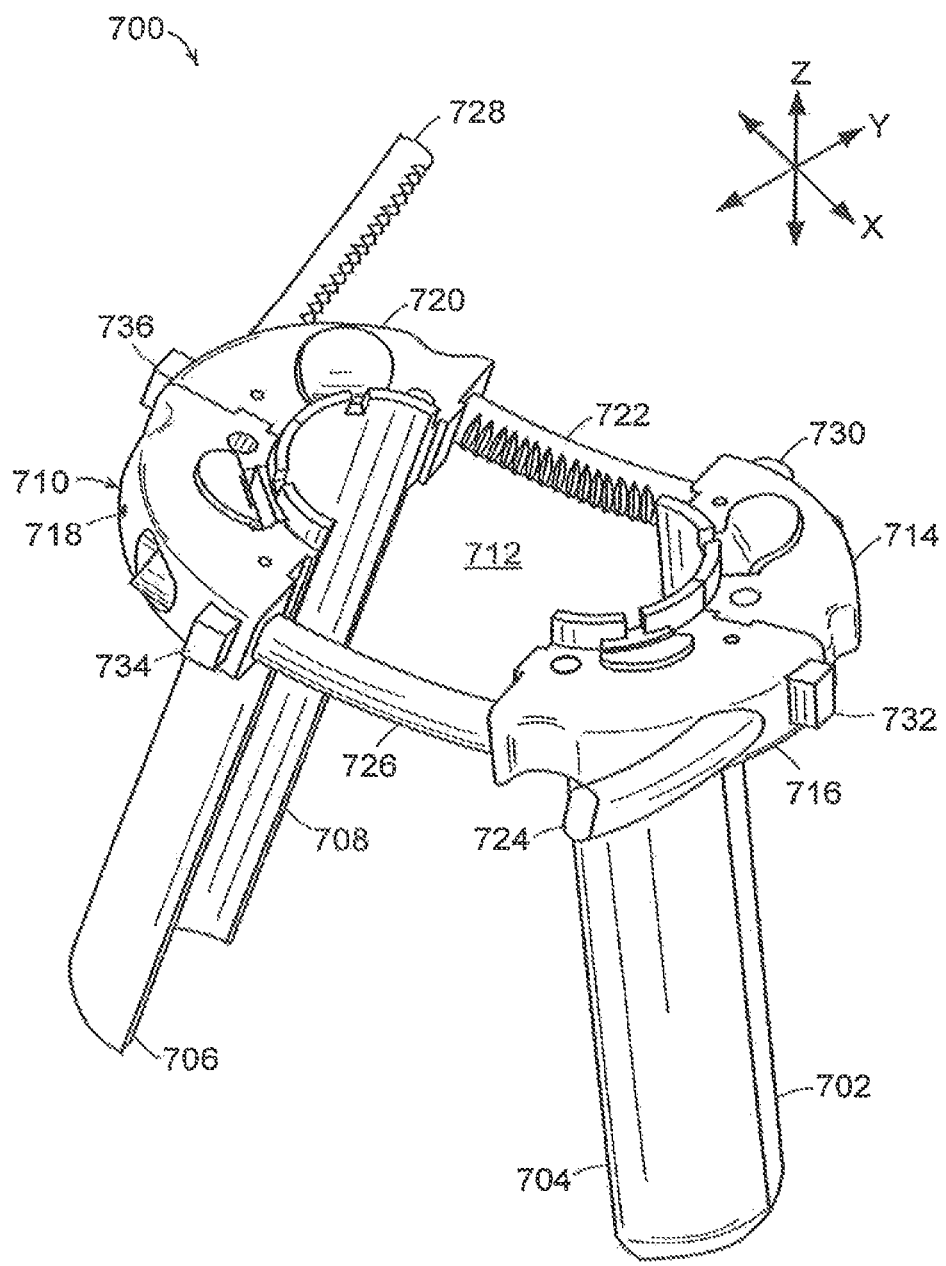
Figure 8:
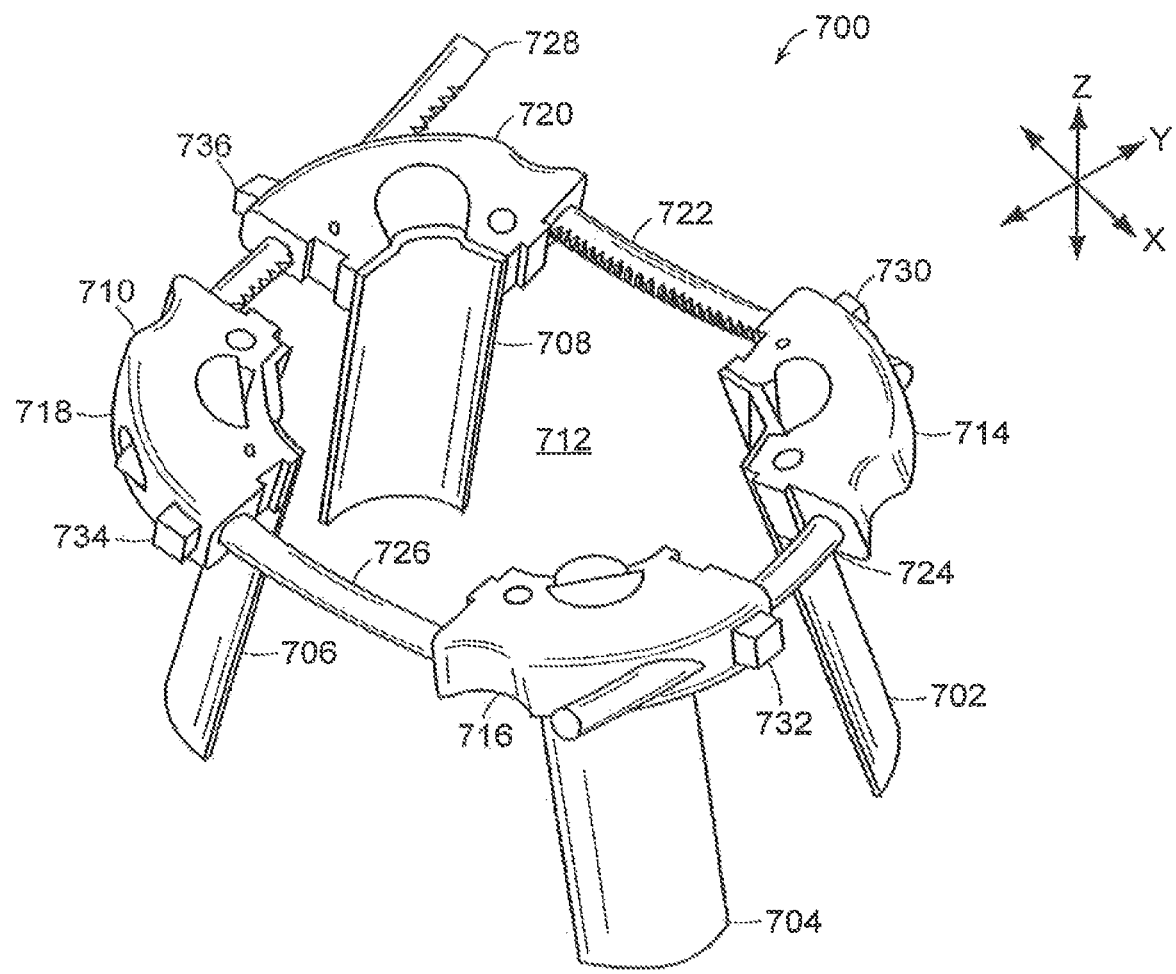

FIGS. 6-8 illustrates one embodiment of a retractor of the invention in three different positions or degrees of expansion. FIG. 6 illustrates refractor 700 in a fully collapsed or contracted position. Retractor 700 includes four retractor blades 702, 704, 706, 708 and an expandable frame 710 having a major plane (parallel to plane XY). Refractor blades 702, 704, 706, 708 are attached at their respective proximal ends to expandable frame 710. Retractor blades 702, 704, 706, 708 are arcuate or curved, and in this first position, their collective inner faces contact, thereby defining a conduit in the shape of a hollow cylinder.

In the contracted position illustrated in FIG. 6, the inner diameter of access portal 712, defined by base components 714, 716, 718, 720 of expandable frame 710, is reduced in size relative to its size in the positions illustrated in FIGS. 7 and 8. This allows retractor 700 to be inserted into an organism or surgical patient (e.g., a human or other mammal) through an incision of minimal size. Retractor 700 includes four ratchet arms 722, 724, 726, 728 and mechanisms for fixing the position of one base component relative to another base component that include ratchet release buttons 730, 732, 734, 736.

Retractor 700 is bisected by at least two planes that are substantially normal to the major plane. A first plane is parallel to the XZ plane and bisects retractor 700, running approximately between base components 714 and 716 and between base components 718 and 720. A second plane is parallel to the YZ plane and bisects retractor 700, running approximately between base components 714 and 720 and between base components 716 and 718.

FIG. 7 illustrates refractor 700 in a partially expanded, or partially translated, position. To expand retractor 700 from the position illustrated in FIG. 6 to the position illustrated in FIG. 7, force is applied to expandable frame 710 to move base component 714 along ratchet arm 722 and base component 718 along ratchet arm 726. In this manner, expandable frame 710 moves approximately in, or parallel to, the major plane from a first position (i.e., the one illustrated in FIG. 6) to a second position (i.e., the one illustrated in FIG. 7) substantially along the first plane and generally away from the second plane.

Ratchet arms 722, 724, 726, 728 are arcuate. Movement of base components 714, 716, 718, 720 along arcuate ratchet arms 722, 724, 726, 728 causes an asymmetric or uneven expansion and contraction of retractor 700. That is, as expandable frame 710 expands, an average distance between the ends of ratchet blades 702, 704, 706, 708 that are distal from expandable frame 710 increases more than the average distance between the ends proximal to expandable frame 710 and more than an average distance between base components 714, 716, 718, 720. When used during a surgical procedure, this unequal expansion allows the distal ends of the retractor blades to retract deep tissue while reducing the size of an incision needed to accommodate the expandable frame. In some embodiments, movement of the base components does not cause an asymmetric or uneven expansion and contraction of the retractor. For example, if the ratchet arms are straight, expansion and contraction of the expandable frame results in an equal amount of expansion and contraction of the distal ends of the blades. In some embodiments, the shape of the ratchet aims is chosen in order to produce a desired degree of asymmetric expansion.

The curvature of ratchet arms 722, 724, 726, 728 causes base components 714, 716, 718, 720 to move slightly out of the major plane as expandable frame 710 is moved to various positions or degrees of expansion and contraction.

In some embodiments (e.g., the one shown in FIG. 6), the base components are arranged in such a way that the expandable frame is substantially coplanar and arranged flat in the major plane. However, this invention also includes embodiments where one or more portions of the expandable frame is not substantially coplanar at one or more positions or degrees of expansion and contraction.

FIG. 8 illustrates retractor 700 in a position where expandable frame 710 is farther expanded from the position illustrated in FIG. 7. To expand retractor 700 from the position illustrated in FIG. 7 to the position illustrated in FIG. 8, force is applied to expandable frame 710 to move base component 716 along ratchet arm 724 and base component 720 along ratchet arm 728, substantially along the major plane. In this manner, expandable frame 710 moves from the second position the one shown in FIG. 7) to a third position (i.e., the one shown in FIG. 8) substantially along the second plane and generally away from the first plane.

If desired, expandable frame 710 is able to be expanded or contracted to many different positions by moving one or more of base components 714, 716, 718, 720 along ratchet arms 722, 724, 726, 728, respectively. In this way, retractor 700 can be expanded or contracted to a wide variety of desired positions.

Refractor 700 illustrates a connector that includes ratchet arms 722, 724, 726, 728, For example, FIG. 7 illustrates ratchet arm 726 of base component 716 partially extending through neighboring base component 718. Similarly, ratchet arms 724, 722, and 72$ extend through or partially through base components 716, 714, and 720, respectively. In this manner, the connectors connect base components 714, 716, 718, 720 and form expandable frame 710.

Retractor 700 also illustrates a mechanism for fixing the position of a first base component relative to a second base component. For example, FIG. 7 illustrates ratchet release button 734, which includes a series of teeth or grooves that engage a second series of complementary teeth or grooves on ratchet arm 726, thereby fixing the position of base component 718 relative to ratchet arm 726. Hence, ratchet release button 734 fixes the position of base component 716 (i.e., the "first base component") relative to base component 718 (i.e. the "second base component"). Pressing ratchet release button 734 disengages the complementary teeth, and allows base component 718 to move along ratchet arm 726 and provides for the movement of base component 71$ relative to base component 716, Similarly, the position of base component 716 relative to base component 714 is adjustable by engaging or disengaging ratchet release button 732, the position of base component 714 relative to base component 720 is adjustable by engaging or disengaging ratchet release button 730, and the position of base component 720 relative to base component 718 is adjustable by engaging or disengaging ratchet release button 736.

To adjust retractor 700 from the position illustrated in FIG. 8 to the position illustrated in FIG. 7, ratchet release buttons 736 and 732 are pressed, thereby allowing expandable frame 710 to move along the second plane and generally towards the first plane. Similarly, ratchet release buttons 734 and 730 are used to adjust expandable frame 710 along the first plane and generally towards the second plane. In this manner, expandable frame 710 can be adjusted to one or more different positions, allowing retractor 700 to be expanded or contracted to a desired extent.

In some embodiments, the expandable frame includes a connector that comprises one or more hinges which attach two or more base components. FIGS. 9-12 illustrate four different views of retractor 900. Retractor 900 includes retractor blades 902, 904, 906, 908 which are attached to expandable frame 910. Expandable frame 910 includes base components 912, 914, 916, 918. Each base component 912, 914, 916, 918 is constructed or formed from a continuous piece of material that includes each retractor blade 902, 904, 906, 908, respectively. Expandable frame 910 includes ratchet arms 920, 922, which are attached to base components 918, 916, respectively. Ratchet arms 920 extends from base component 918 into the accommodating hole of base component 912, thereby connecting base component 918 to base component 912. Similarly, ratchet arm 922 connects base component 916 to base component 914. Retractor 900 includes mechanisms for fixing the position of a first base component relative to a second base component that comprise ratchet release levers 924, 926. Ratchet release levers 924, 926 provides the same function as the ratchet release buttons illustrated previously and are used to release the positions of base component 914 relative to ratchet arm 922 and base component 912 relative, to ratchet arm 920, respectively.

Expandable frame 910 also includes a connector that comprise hinges 927, 928. Hinge 927 rotatably connects base component 912 to base component 914 and hinge 928 rotatably connects base component 916 to base component 918. Retractor 900 also includes mechanisms for fixing the position of a first base component relative to a second base component that comprises levers 930, 932. Lever 930 locks or immobilizes the rotation of hinge 927, thereby fixing the position of base component 912 relative to base component 914. Lever 932 locks or immobilizes the rotation of hinge 928, thereby fixing the position of base component 918 relative to base component 916. Expandable frame 910 defines access portal 934.

Figure 9:
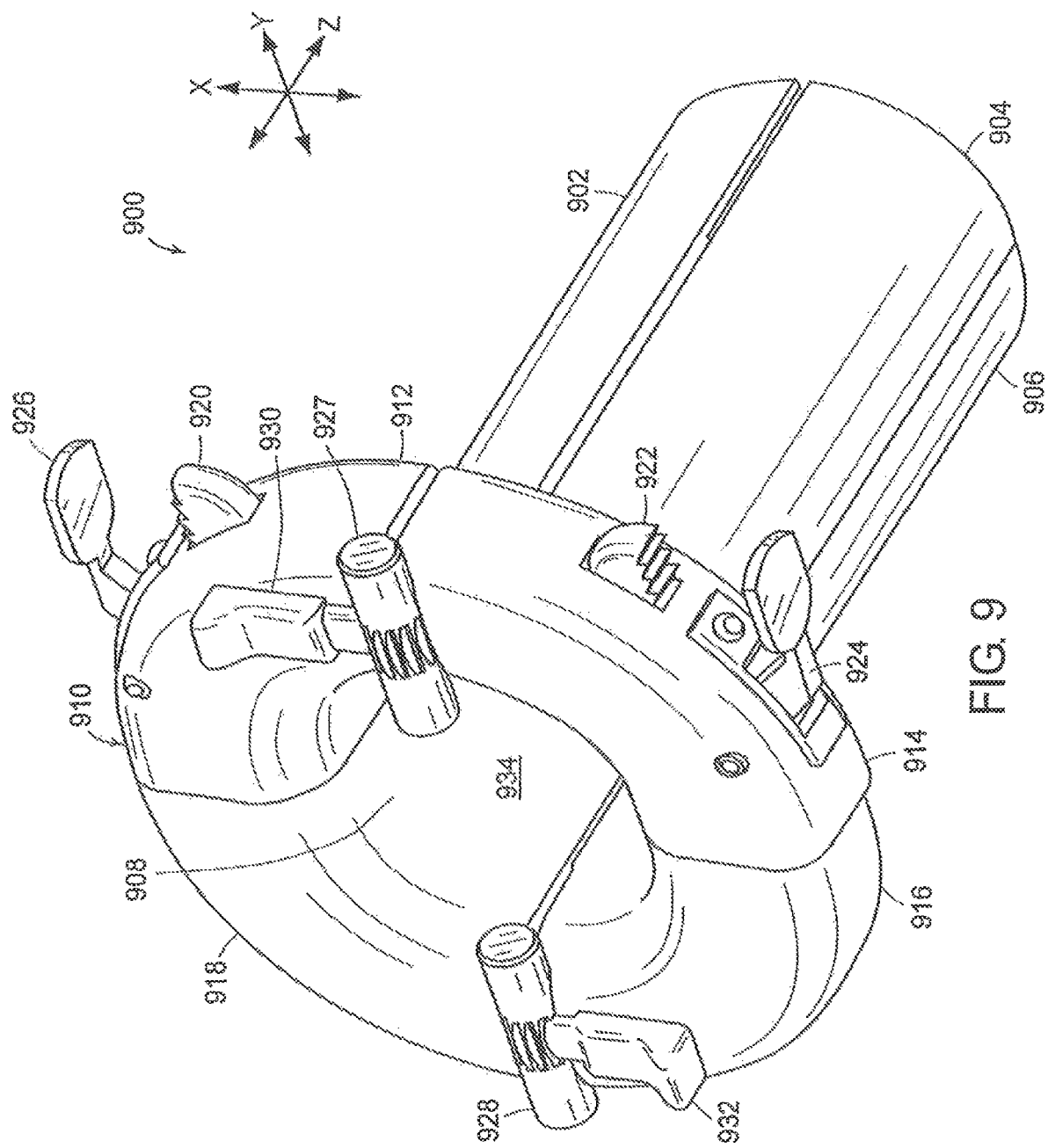
FIGS. 9-12 illustrate four different views of one embodiment of a retractor of the invention.
Figure 10:
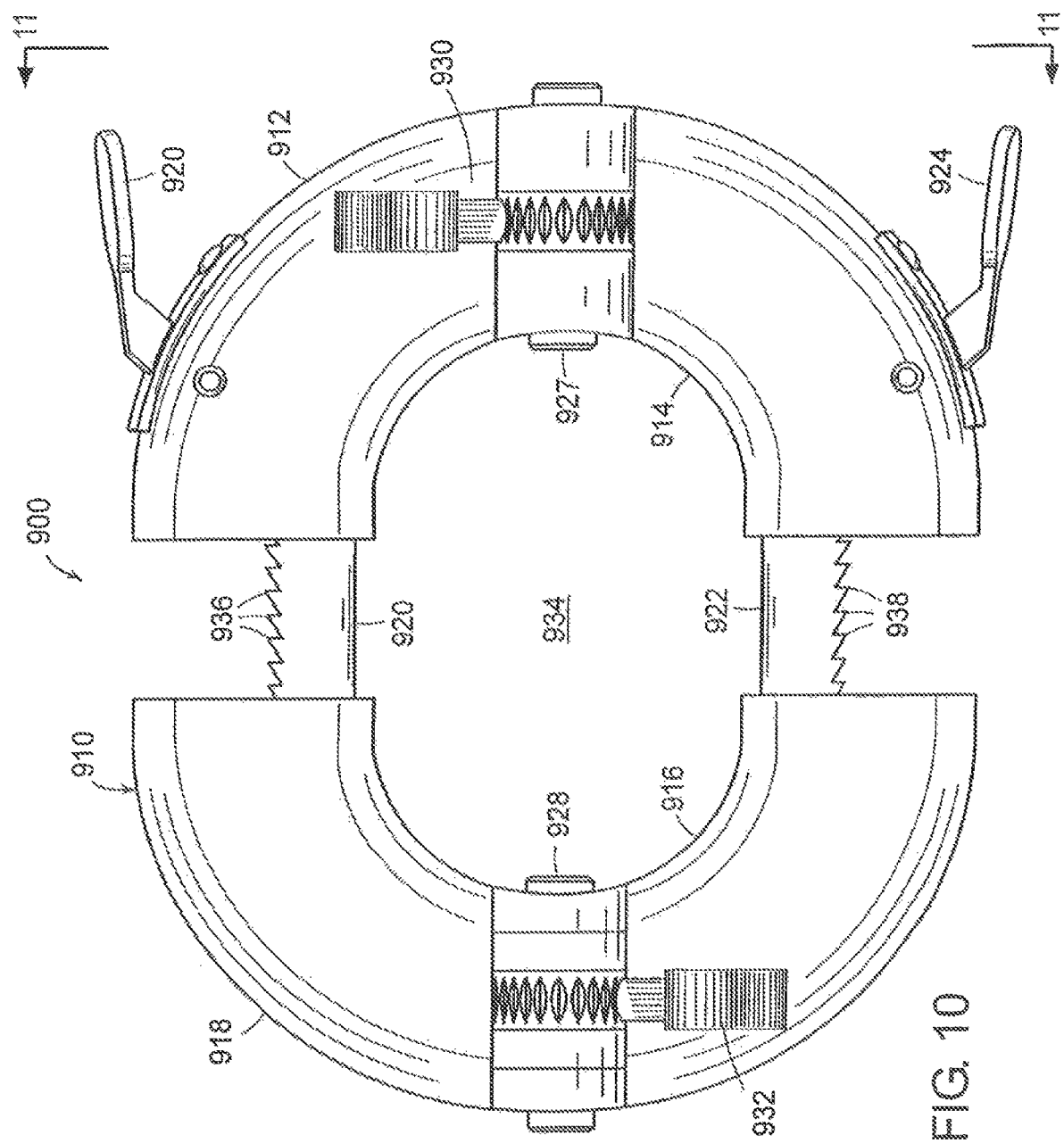

FIG. 10 illustrates a top-down view of retractor 900 after expandable frame 910 has been moved from the first position, illustrated in FIG. 9, to a second position. Ratchet anus 920, 922 are substantially straight and provide for movement of base component 912 relative to 918 and movement of base component 914 relative to base component 916.

Ratchet lever 926 engages teeth 936 on the side of ratchet arm 920, thereby fixing the position of base component 918 relative to base component 912. Similarly, ratchet lever 924 engages teeth 938 on the side of ratchet arm 922, thereby fixing the position of base component 916 relative to base component 914.

Figure 11:
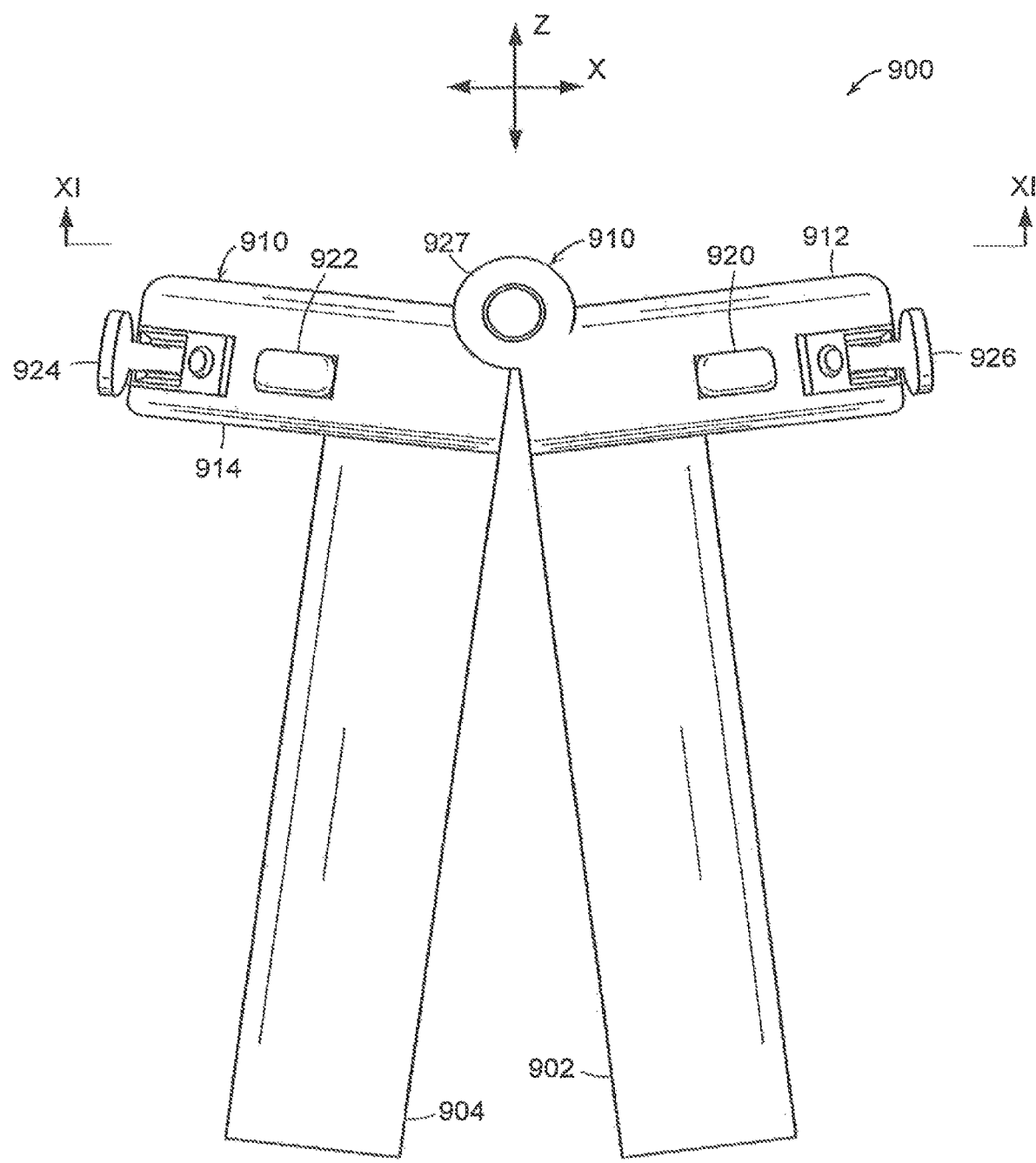
Figure 12:
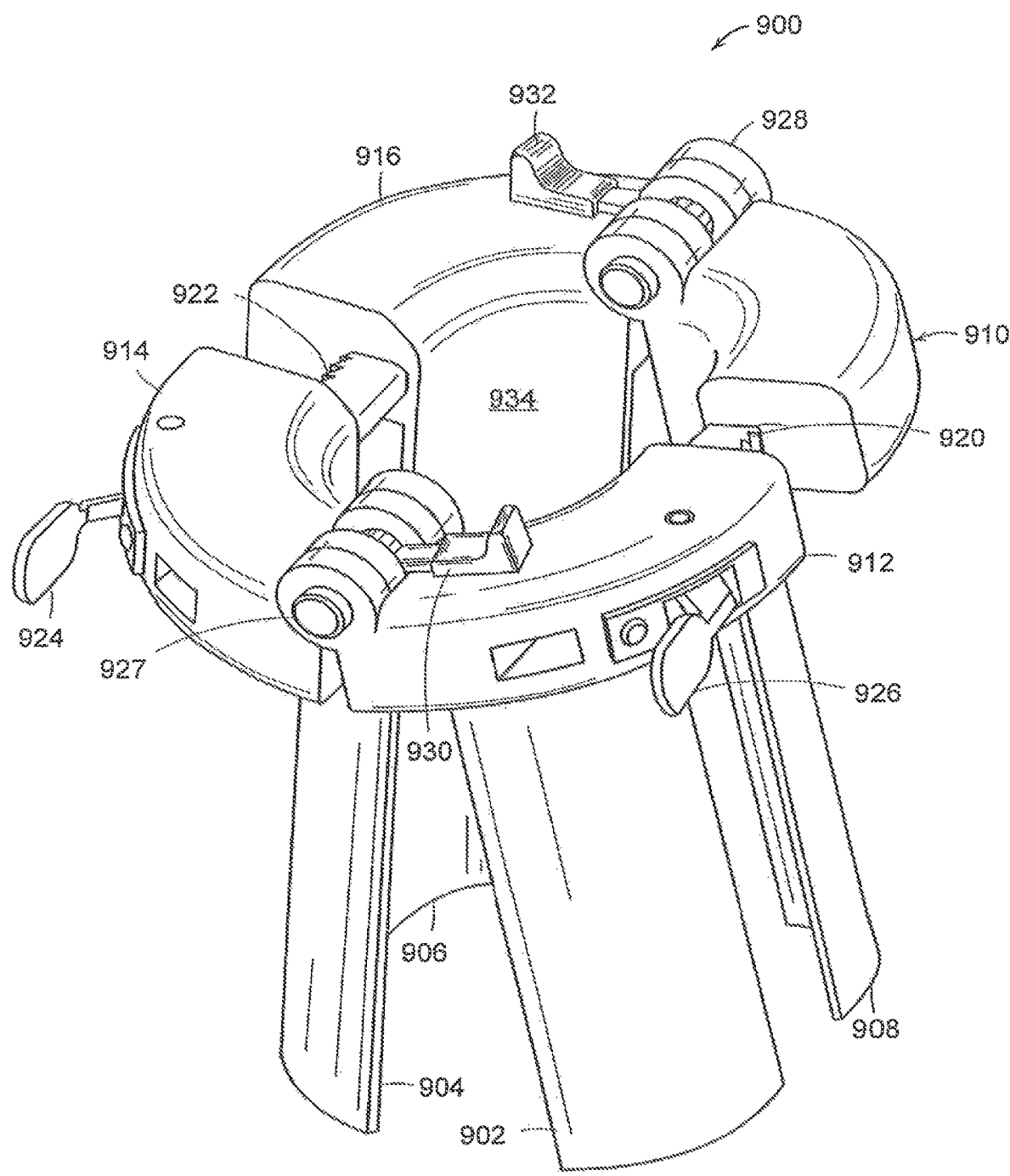

FIG. 11 illustrates a side view of retractor 900 after expandable frame 910 has been moved from the second position to a third position by rotating about hinge 927 and hinge 928 (not shown in FIG. 11). Hinges 927, 928 provide for movement of base components 914, 916 relative to base components 912, 918. The rotation results in an average distance between distal ends of retractor blades 902, 904 that is larger than both the average distance between the two proximal ends of retractor blades 902, 904 and the average distance between the two base components 912, 914. FIG. 12 illustrates an additional view of retractor 900 after expandable frame 910 has been moved to the third position.

Optionally, one or more blades of a retractor include one or more blade extensions that are telescopically and slidably attached to the blade. In some embodiments, the retractor includes a blade extension fixation mechanism that, when engaged, immobilizes or secures the blade extension at a desired telescoped length. One example of a blade extension fixation mechanism is one or more series of teeth or ridges on the blade and/or blade extension which slidably secure the extension to the blade. Another example of a blade extension fixation mechanism includes a series of teeth on the blade and a tab on the blade extension. The tab engages the teeth on the blade to immobilize the blade extension. Applying force to the tab disengages it from the teeth and allows the blade extension to slide relative to the blade. Many other blade extension fixation mechanisms are encompassed by this invention, such as hooks, levers, latches, screws, locking mechanism, combinations thereof, and the like. Additionally, the blade extension fixation mechanisms can include an automated mechanism, such as one or more motorized screws.

Optionally, a retractor includes a mechanism for preventing the blade extension from disengaging from a blade as it moves relative to the blade. An example of such a mechanism include one or more grooves or tracts on the blade and/or blade extension which slidably secure the extension to the blade. The grooves allow the extension to slide relative to the blade, but prevent the extension from disengaging from the blade. Many other mechanisms for preventing the blade extension from disengaging from a blade are encompassed by this invention.

Optionally, the blade extension includes a telescope tab which provides a telescopic attachment point to ease the act of telescoping the blade extension.

Figures 13A, 13B, 13C:
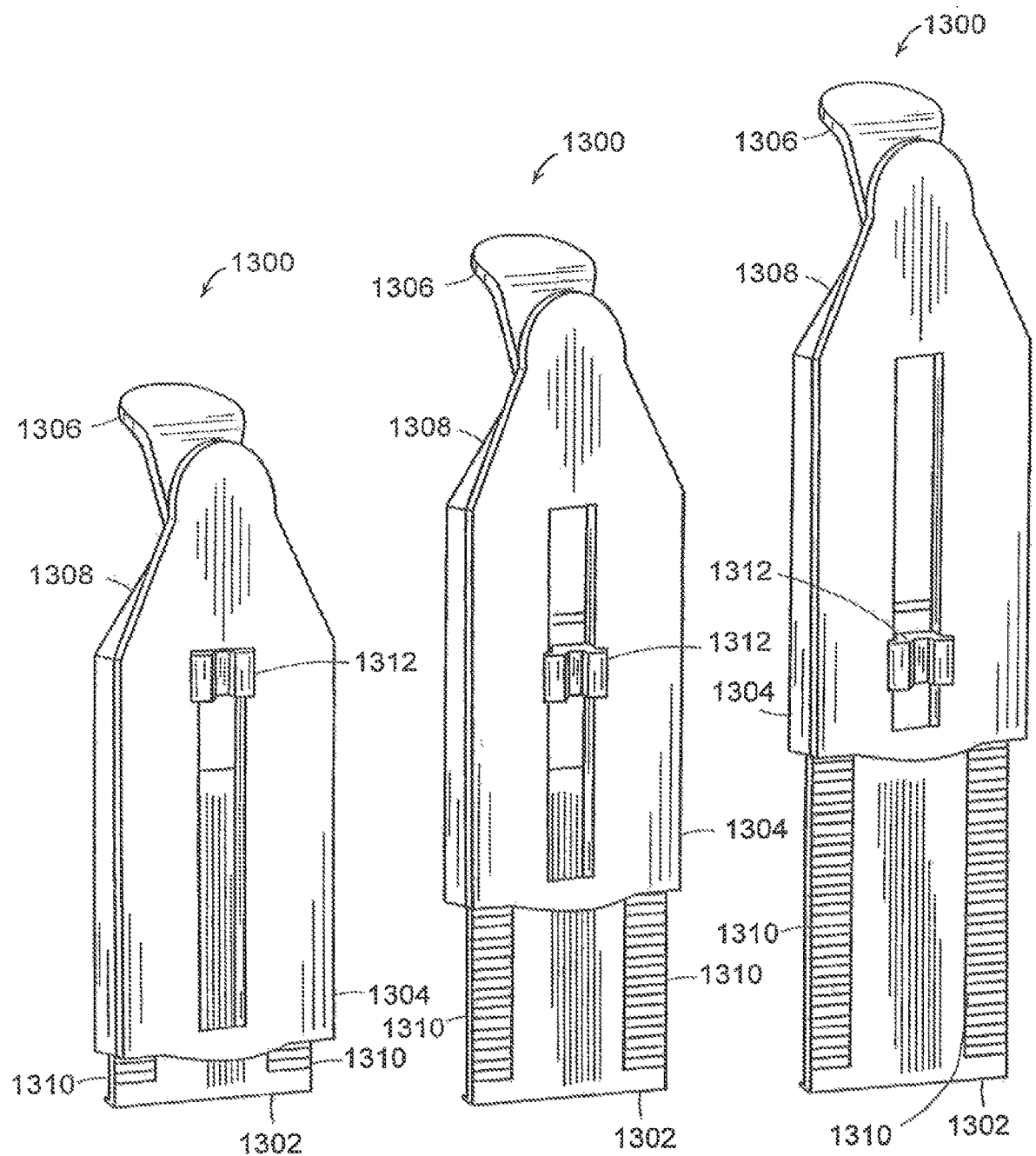
FIGS. 13A-13C illustrate the inner face of a blade of one embodiment of the invention with a blade extension at progressively longer telescopic lengths.

The inner face of blade 1300 is illustrated in FIGS. 13A, 13B, and 13C, with blade extension 1302 extending from distal end 1304 of blade 1300 at progressively longer telescopic lengths. Blade 1300 includes an attachment mechanism that comprises clip 1306 at proximal end 1308. Blade 1300 includes blade extension fixation mechanism comprising two series of teeth 1310 which extend at least a portion of the length of blade extension 1302. A complementary series of teeth forcibly engage both tracts of teeth 1310, keeping blade extension 1302 at a desired telescopic length. Blade extension 1302 includes telescopic attachment point 1312 which protrudes through an opening in the inner face of blade 1300.

Figure 14:
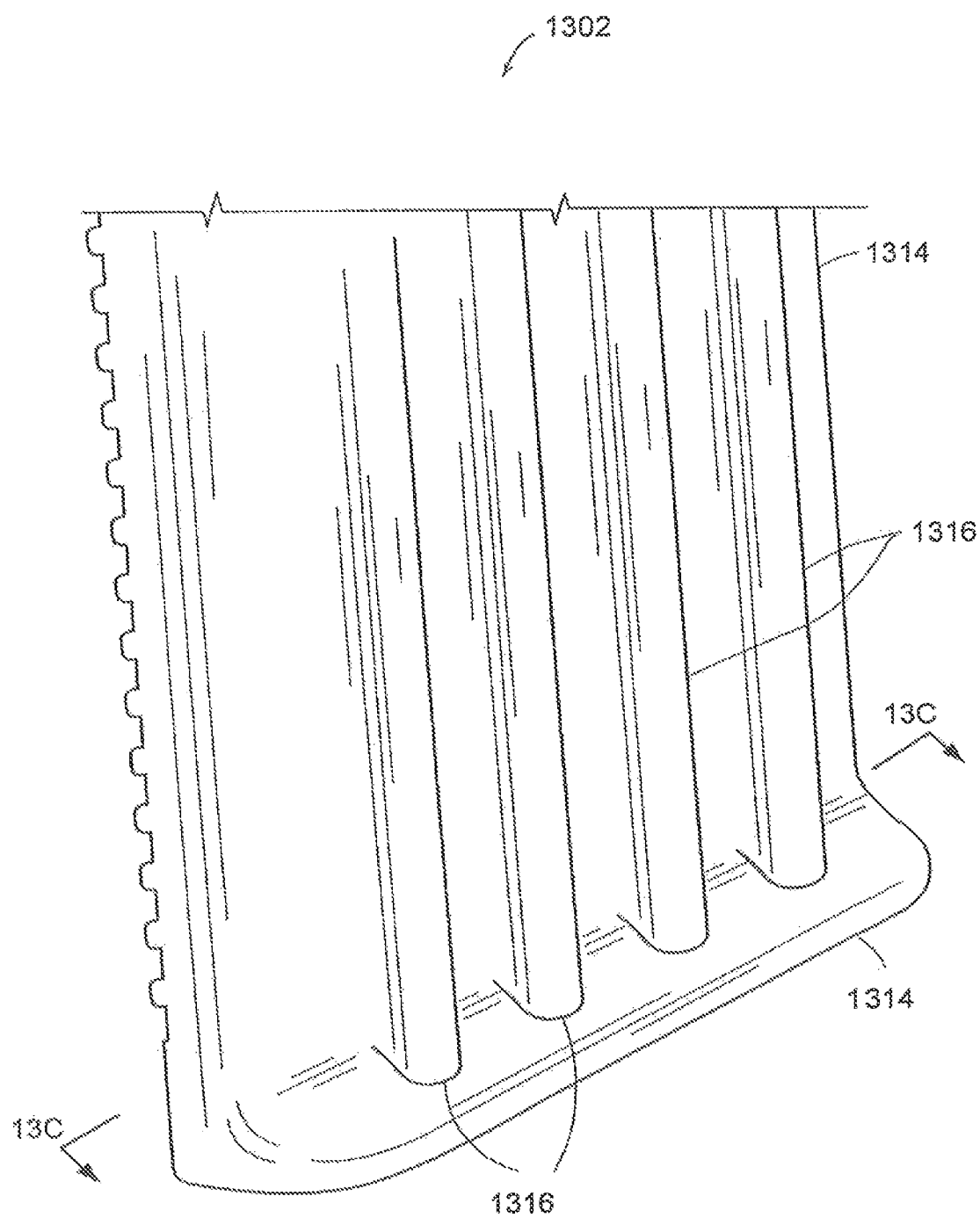
FIG. 14 illustrates a close up view of the distal end of the outer face of the blade extension shown in FIGS. 13A-13C.

Optionally, one or more blades and/or blade extensions include a toe-out protrusion extending from the distal end of the outer face. FIG. 14 illustrates a close up view of distal end 1314 of the outer face of blade extension 1302. Toe-out protrusion 1314 extends from the outer face of blade extension 1302. Toe-out protrusion 1314 allows blade extension 1302 to more effectively retract tissue from a surgical site compared to a similar blade extension lacking a toe-out protrusion. Blade extension 1302 also includes ridges 1316 which extend at least a portion of the length of blade extension 1302, and provide more effective retraction of tissue from a surgical site compared to a similar blade extension lacking ridges. In further embodiments, the toe-out protrusion extends at an angle from the face of the blade or blade extension at an angle (e.g., a right angle or an angle greater or lesser than 90°).

In some embodiments, the outer face of one or more blade and/or blade extensions include a textured surface to assist the blades or extensions in gripping tissue. This provides for improved retraction of tissue at a surgical site. For example, portions of the outer faces can have a rough texture, ridges (e.g., the ridges shown in FIG. 14), or similar surface textures.

Figure 15:
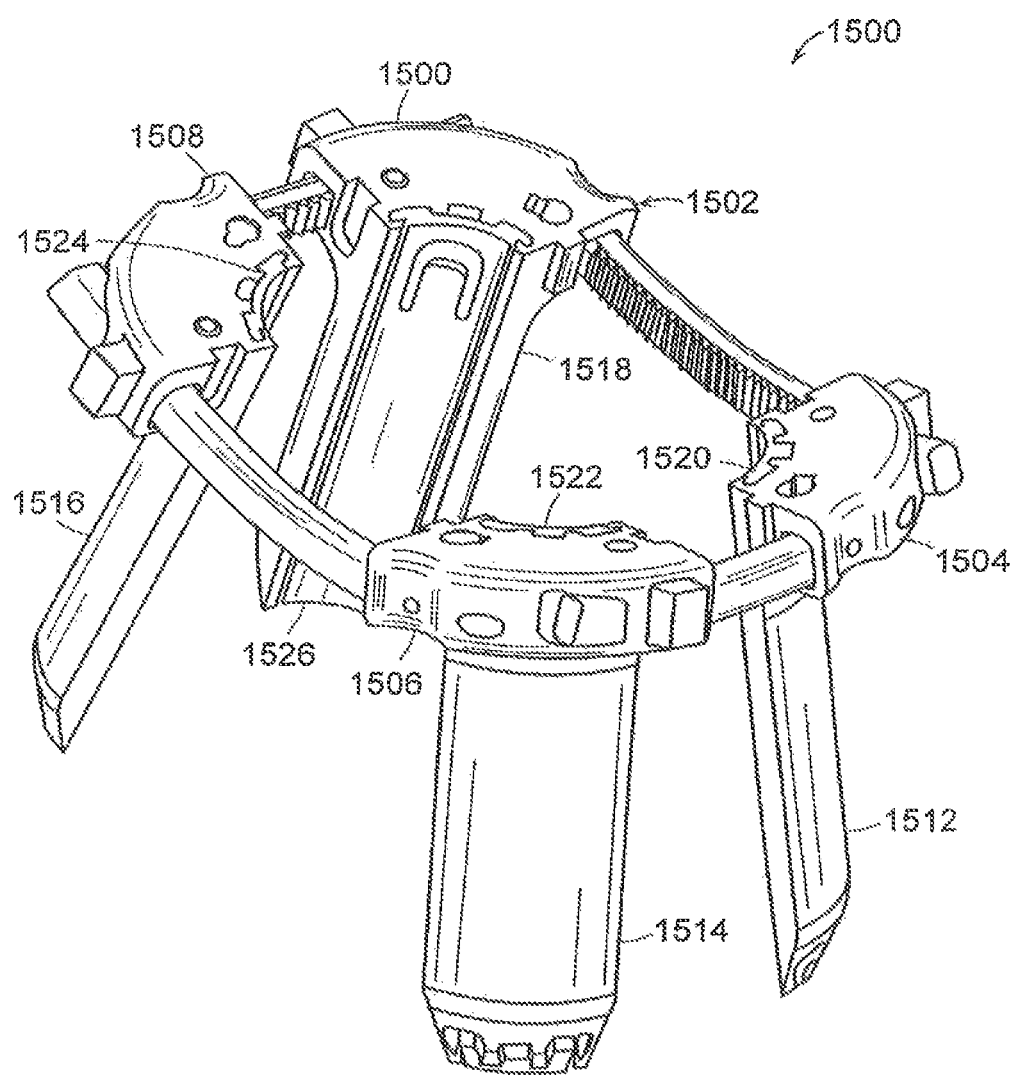
FIG. 15 illustrates one embodiments of a retractor of the invention that includes blade extensions.

FIG. 15 illustrates an embodiments of a retractor of the invention that includes blade extensions. Retractor 1500 includes expandable frame 1502 in a fully expanded position with the greatest average distance between base components 1504, 1506, 1508, 1510. Blades 1512, 1514, 1516, 1518 includes blade extensions 1520, 1522, 1524, 1526, respectively. FIG. 15 illustrates expandable frame 1502 at an expanded position without the blade extensions 1520, 1522, 1524, 1526 telescoped from blades 1512, 1514, 1516, 1518, respectively.

Figure 16A:
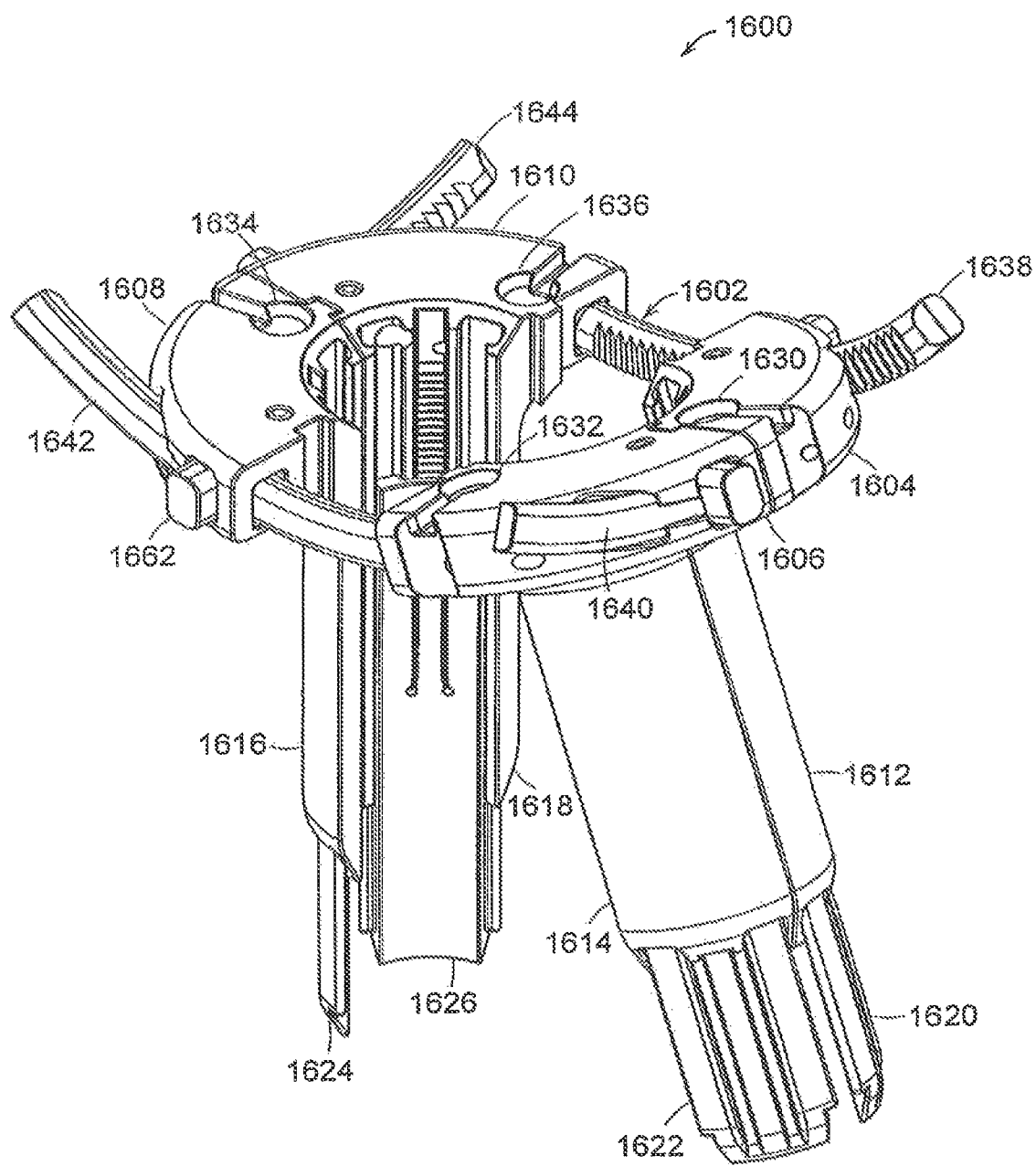

FIG. 16A illustrates another embodiment of the invention that includes retractor 1600, Retractor 1600 includes expandable frame 1602 (which is at a slightly less expanded position than expandable frame 1502 illustrated in FIG. 15) and blade extensions 1620, 1622, 1624, and 1626 partially telescoped from blades 1612, 1614, 1616, and 1618, respectively. Retractor 1600 also comprises a plurality or connectors that include arms 1638, 1640, 1642, and 1644.

Figure 16B:
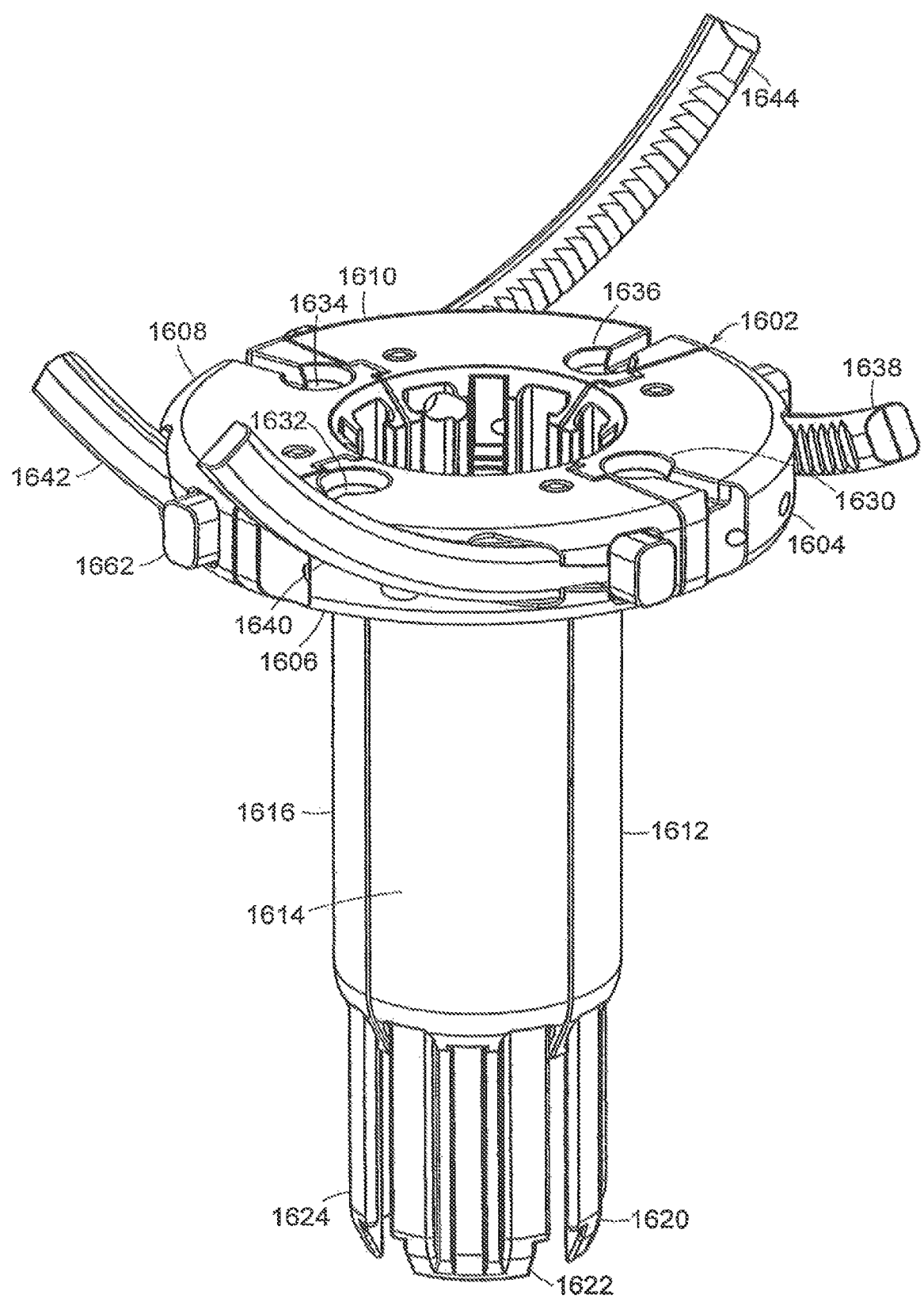

FIG. 16B illustrates retractor 1600 with expandable frame 1602 in a contracted or condensed position and extensions 1620, 1622, 1624, and 1626 partially telescoped from blades 1612, 1614, 1616, and 1618, Retractor 1600 includes a plurality of universal attachment points, including attachment points or holes 1630, 1632, 1634, and 1636. Attachment holes 1630, 1632, 1634, and 1636 can be used to attach surgical instruments, additional blades, retractor support structures (e.g., rigid arms), and the like.

Figure 16C:
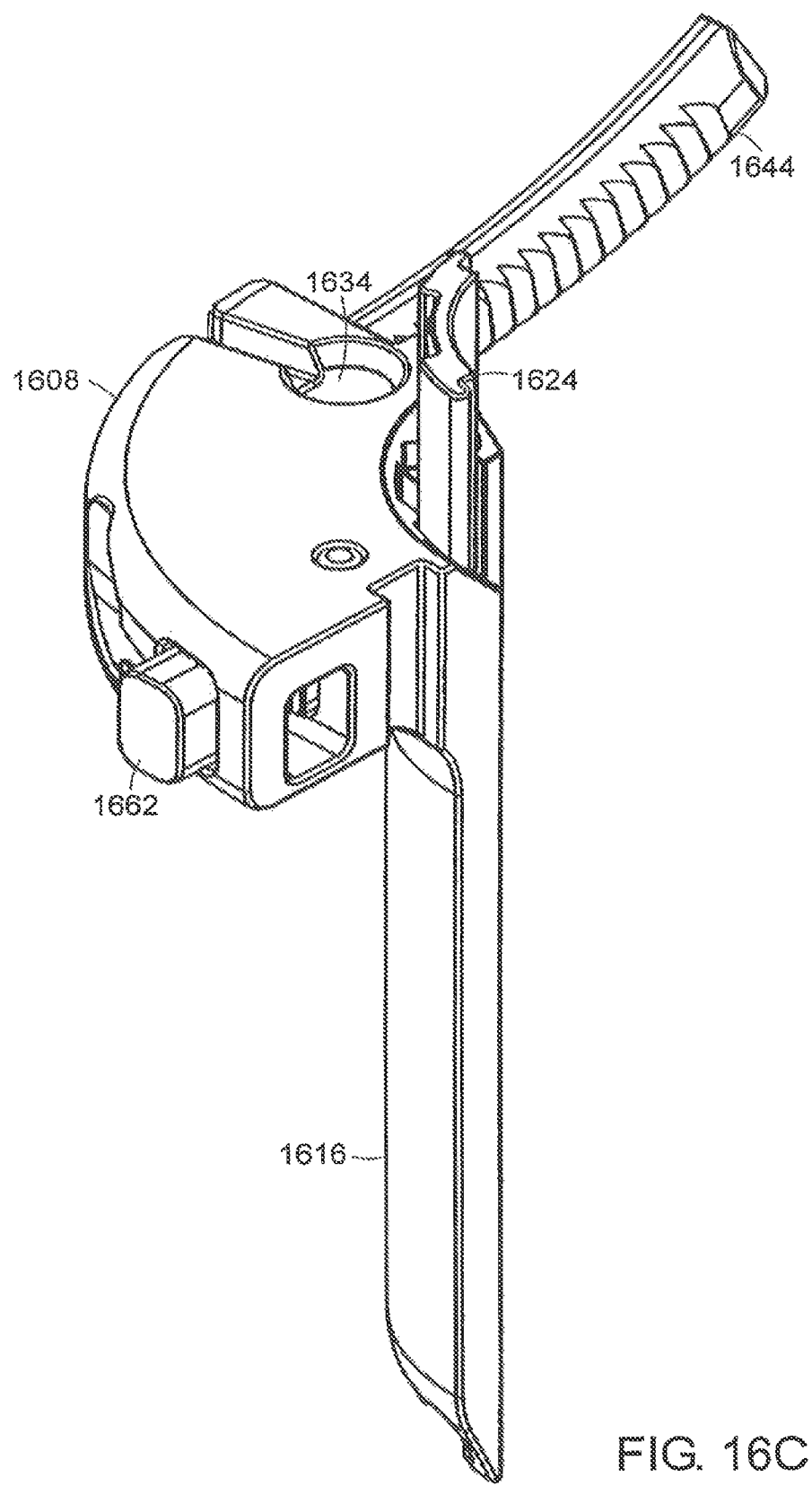
Figure 16D:
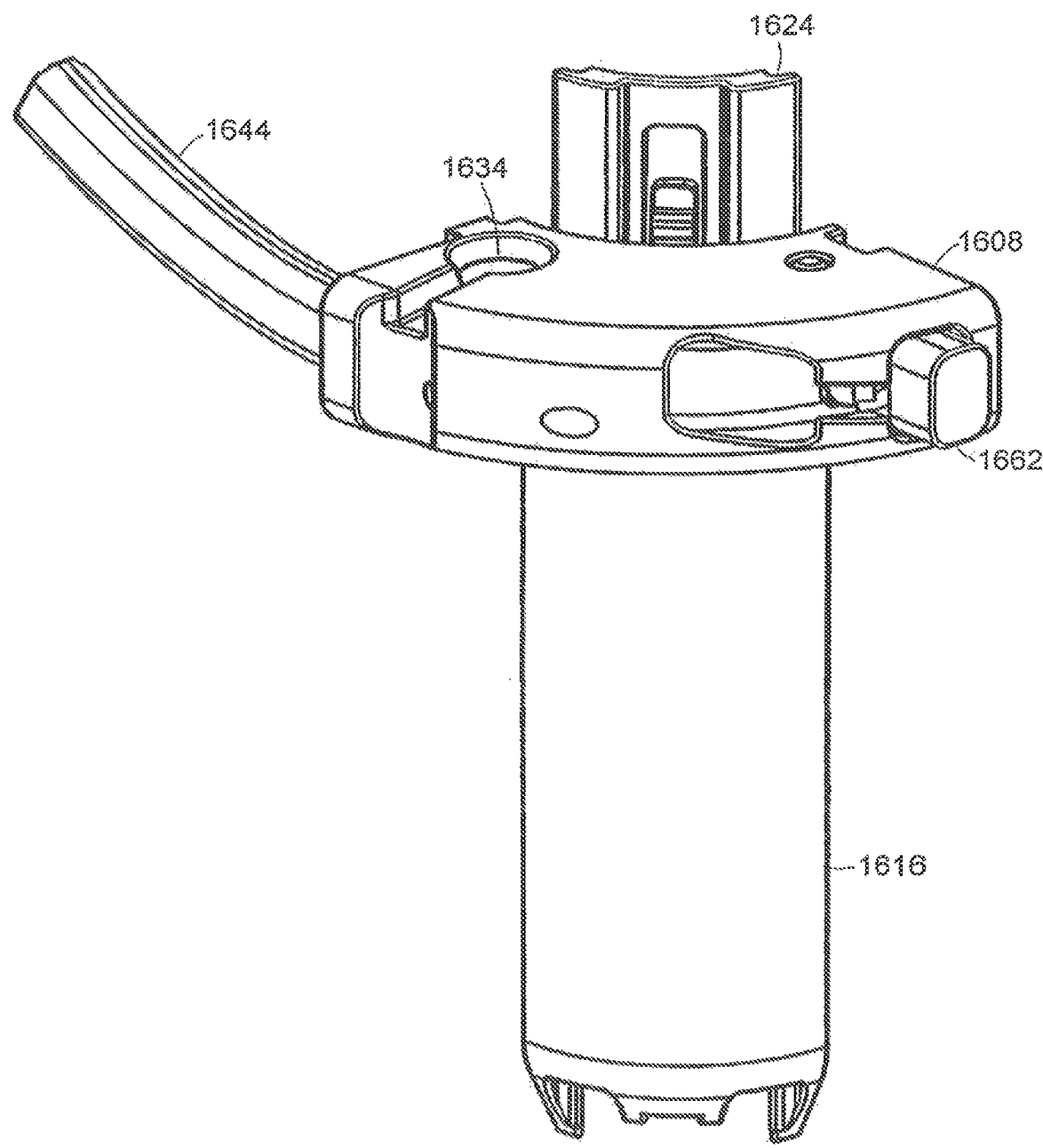

FIG. 16C illustrates one perspective view of a portion of retractor 1600 that includes component 1608, extension 1624, and arm 1644. FIG. 16D illustrates another perspective view of a portion of retractor 1600 that includes component 1608 and extension 1624.

Figure 16E:
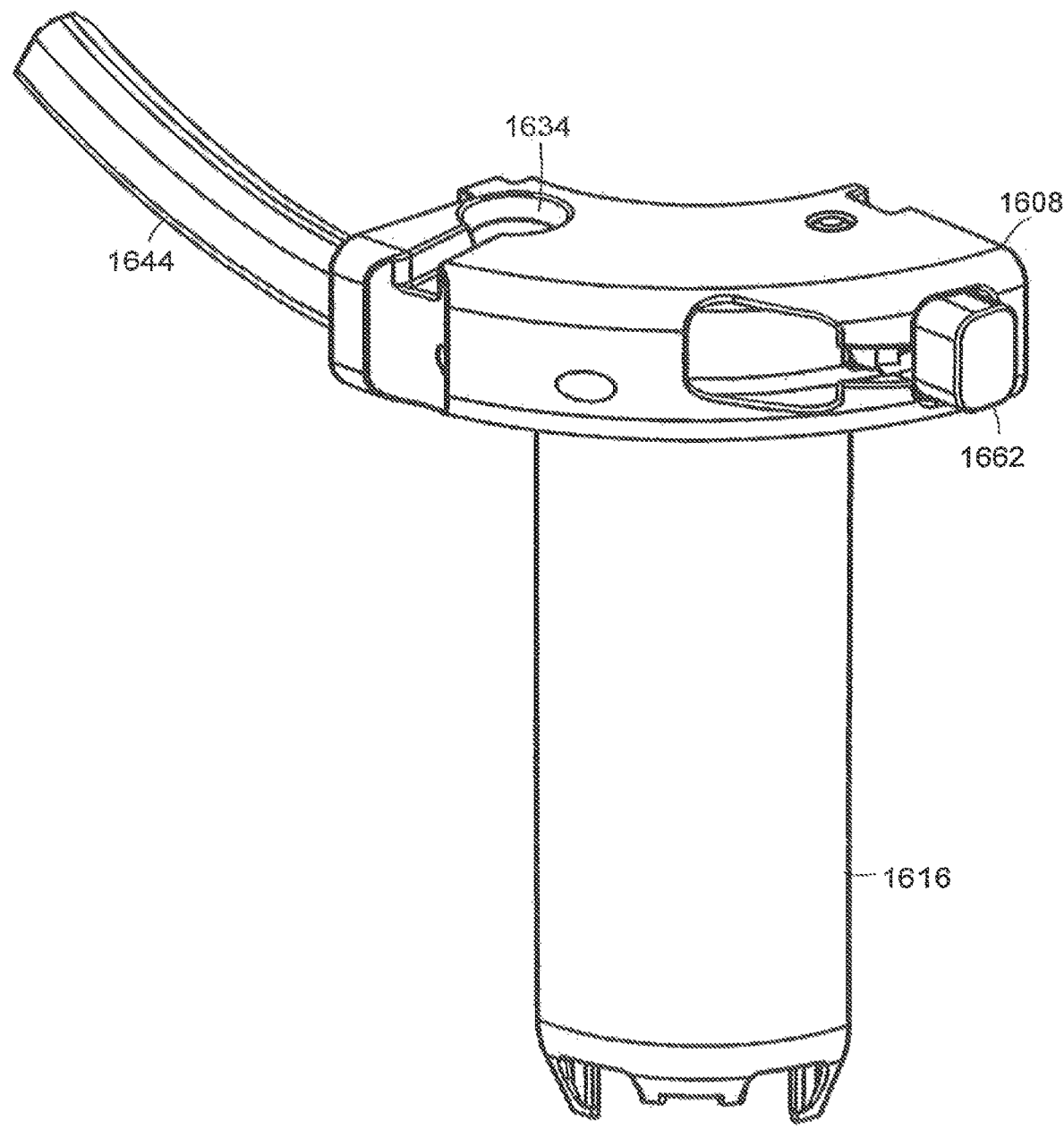
Figure 16F:
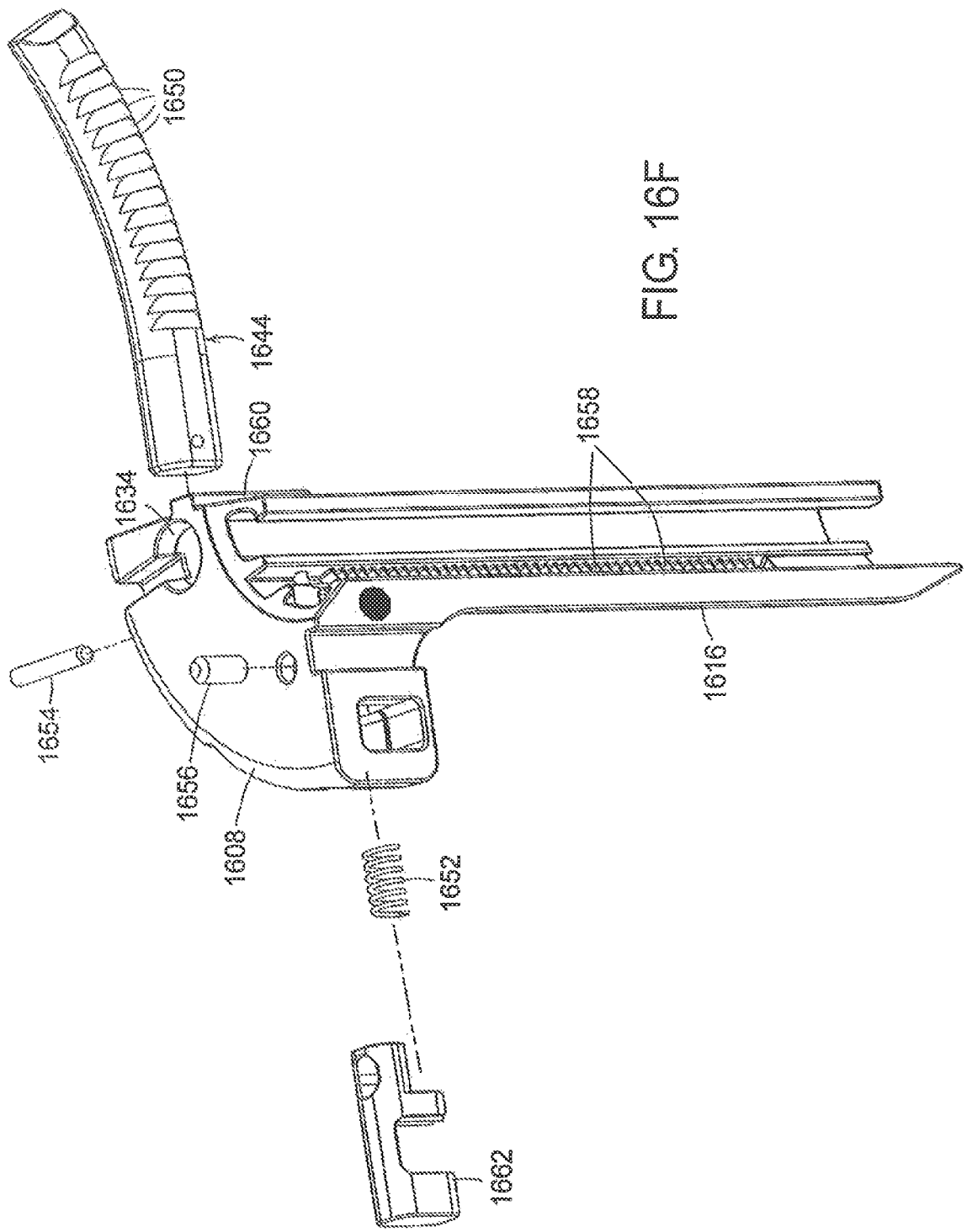

FIG. 16E illustrates yet another perspective view of a portion of retractor 1600 that includes component 1608, blade 1616, and aim 1644. In the perspective view shown in FIG. 16E, extension. 1624 has been removed from blade 1616, FIG. 16F illustrates a perspective view of a portion of retractor 1600 that includes a disassembled view of the portion of retractor 1600 that is illustrated in FIG. 16E. Ratchet arm release button 1662 is assembled to base component 1608 by using pin 1656. Spring 1652 provides sufficient force to engage arm 1642 (not illustrated in FIG. 16F) and frustrate movement of component 1608 relative to arm 1642, unless a practitioner depresses button 1662. Retractore 1600 is free to expand without pressing the buttons due to the ramping of the complementary teeth on the arms and buttons. To collapse, or contract refractor 1600, the practitioner of the invention presses the buttons to disengage the teeth of the arms and buttons. Arm 1644 is secured to base component 1608 with pin 1654. Ratchet arm 1644 includes a portion of a mechanism for securing the relative position of base component 1608 that includes teeth 1650.

Figure 16G:
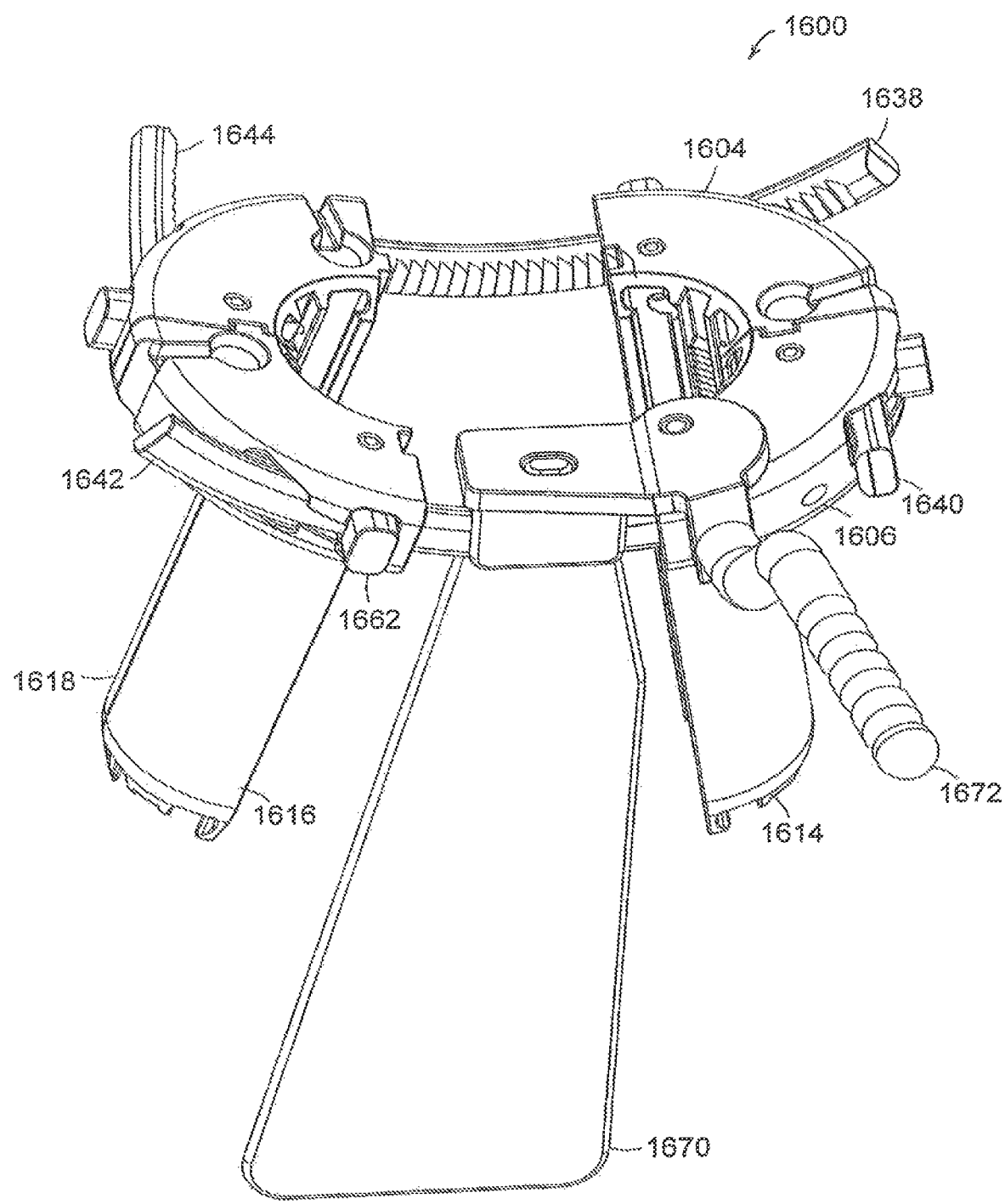

In some embodiments, the connectors of the retractors of this invention serve as attachment points for additional surgical instruments and/or retractor blades. FIG. 16G illustrates another perspective view retractor 1600 that includes blade 1670. Trapezoidal blade 1670 is attached or assembled to arm 1642. Handle 1672 is used to assemble blade 1670 to retractor 1600. A practitioner of the invention can use arm 1672 to assemble blade 1670 to retractor 1600 at attachment point 1632 (not illustrated in FIG. 16G).

Figures 16H, 16I:
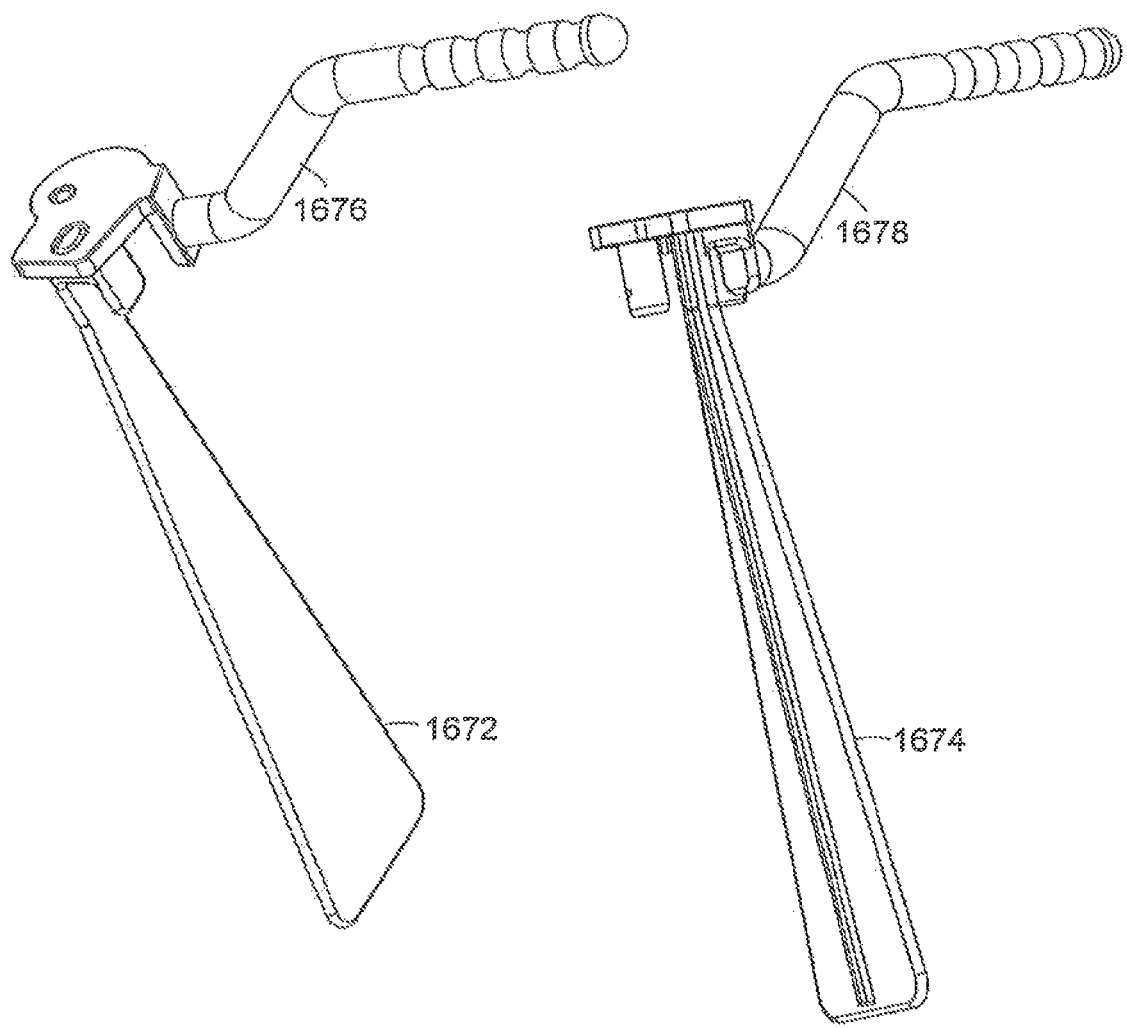

While blade 1670 comprises an trapezoidal shape, it will be recognized that the blades of the retractors of the invention can comprise a form or a shape of blades known in the art. FIGS. 16H and 16I illustrate two alternative blades 1672 and 1674 which are attached or assembled to arms 1676 and 1678, respectively.

In some embodiments, an inserter is use to direct the retractors of the present invention to desired location. FIG. 16J illustrates a portion of the invention that includes inserter 1680. Inserter 1680 includes a plurality of attachment pins 1682. Attachment pins 1682 secure inserter 1680 to some or all of the attachment holes of the frame of the retractor of the invention. A practitioner of the invention assembles or attaches inserter 1680 to a retractor of the invention and uses handles 1684 to position or direct retractor 1600 to a desired location within a mammalian anatomy.

Figure 16K:
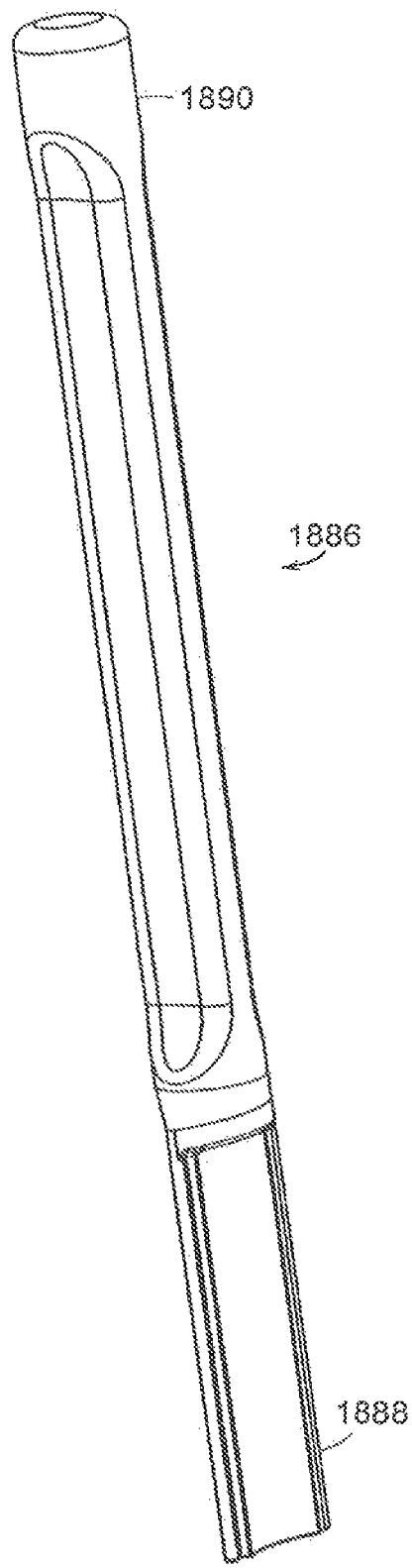
Figure 16L:
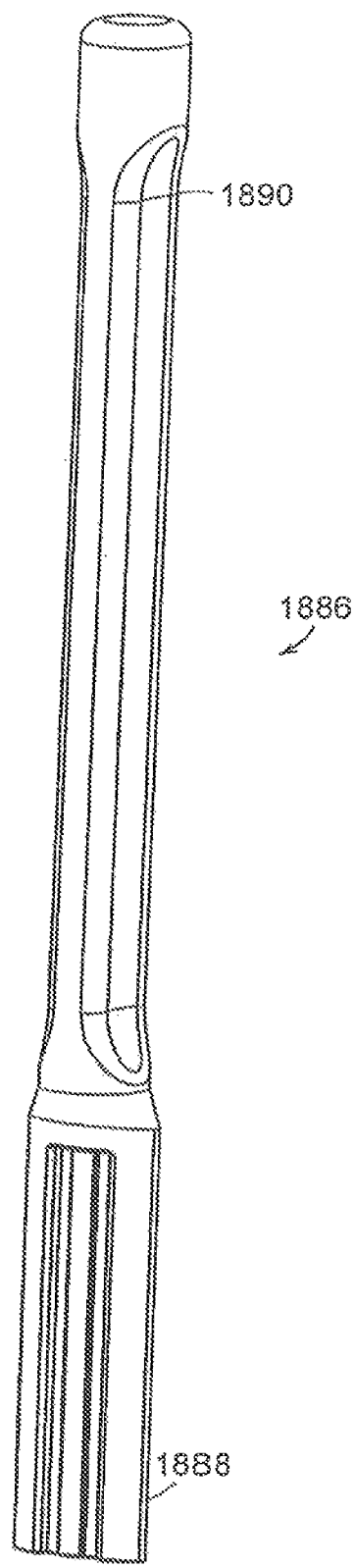

FIGS. 16K and 16L, illustrate perspective view of telescoping blade extender 1886. Telescoping blade extender 1886 includes distal end 1888 and proximal ends 1890. A practitioner uses proximal ends 1890 to slide blade extension(s) 1620, 1622, 1624, and/or 1626 with respect to blades 1612, 1614, 1616, and 1618 to a desired location within a mammalian anatomy, respectively.

Figure 16M:
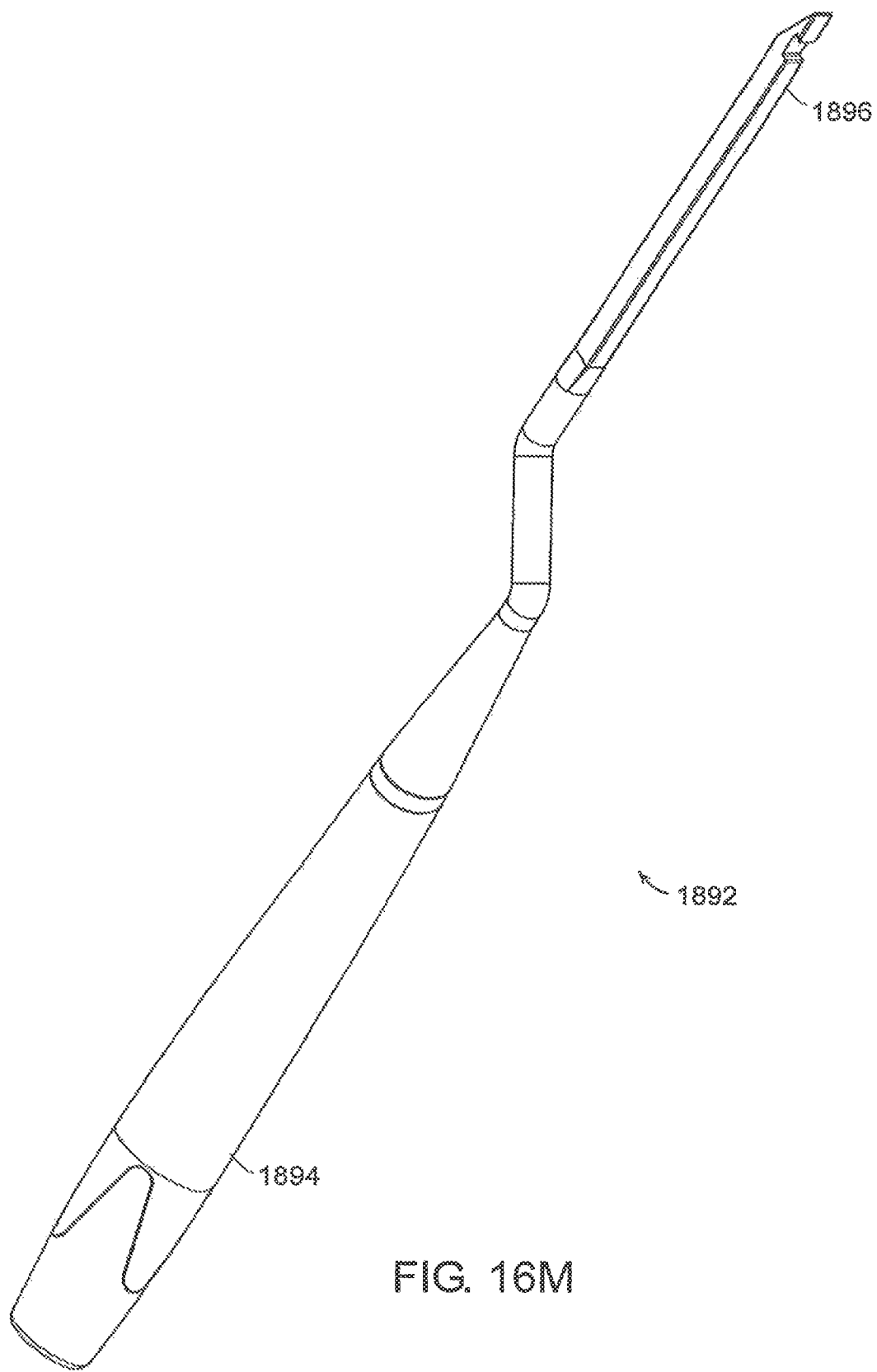

FIG. 16M illustrates a perspective view of telescoping blade remover 1892. Telescoping blade remover 1892 includes distal end 1896 and proximal ends 1894. A practitioner uses proximal ends 1894 to latch onto a blade extension and disengage it from a mammalian anatomy and/or reposition the extension to a desired location within a mammalian anatomy.

Figure 17A:
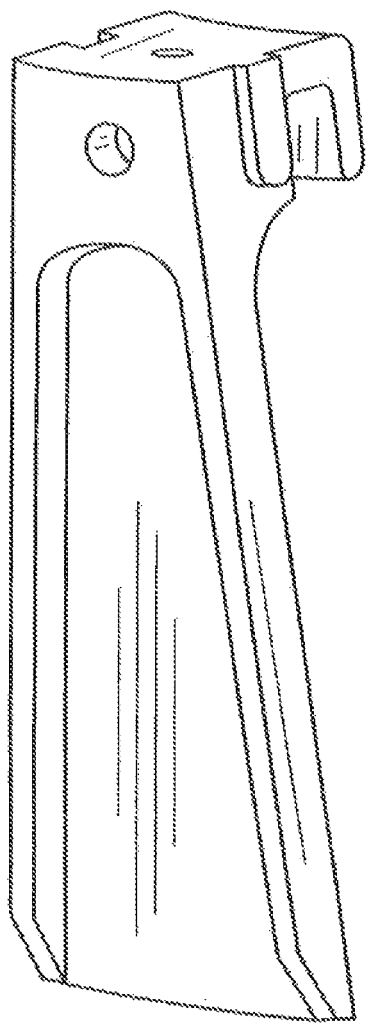
FIGS. 17A-17C illustrate various blade shapes for some embodiments of retractors of the invention.
Figure 17B:
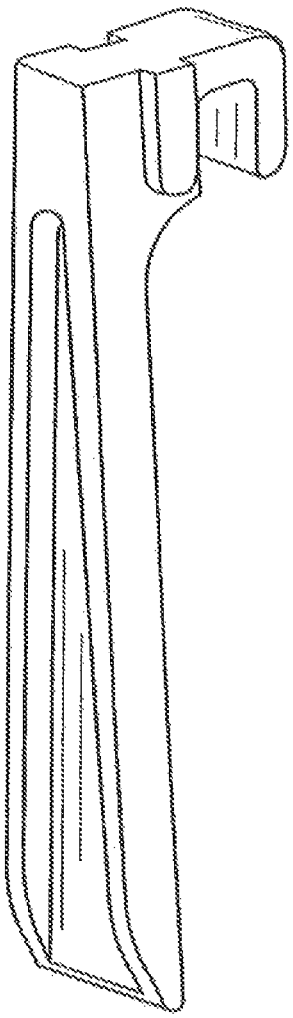
Figure 17C:
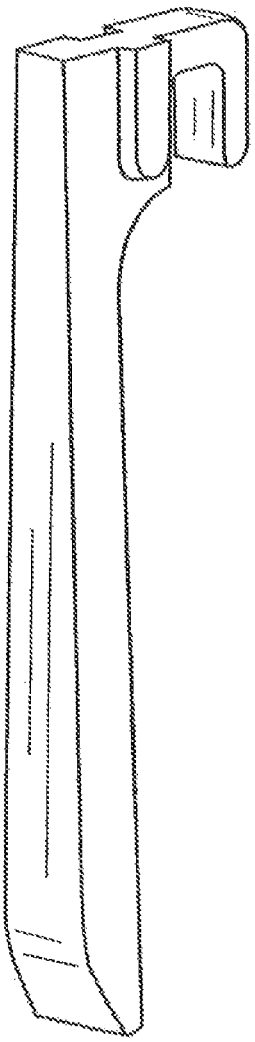

The blades and blade extensions of this invention can be any size or shape desired. In some embodiments, one or more blades or blade extensions are shaped and/or sized for a specific task. For example, a blade can be shaped to retract muscle tissue, adipose tissue, nerve tissue, or other types of tissue, Examples of various blade with disparate trapezoidal shapes are illustrated in FIGS. 17A-17C. The blades illustrated in FIG. 17A-17C are just a few examples of trapezoidal geometries and this invention includes a wide range different blade shapes (e.g., blades with non-trapezoidal geometries).

Figure 17D:
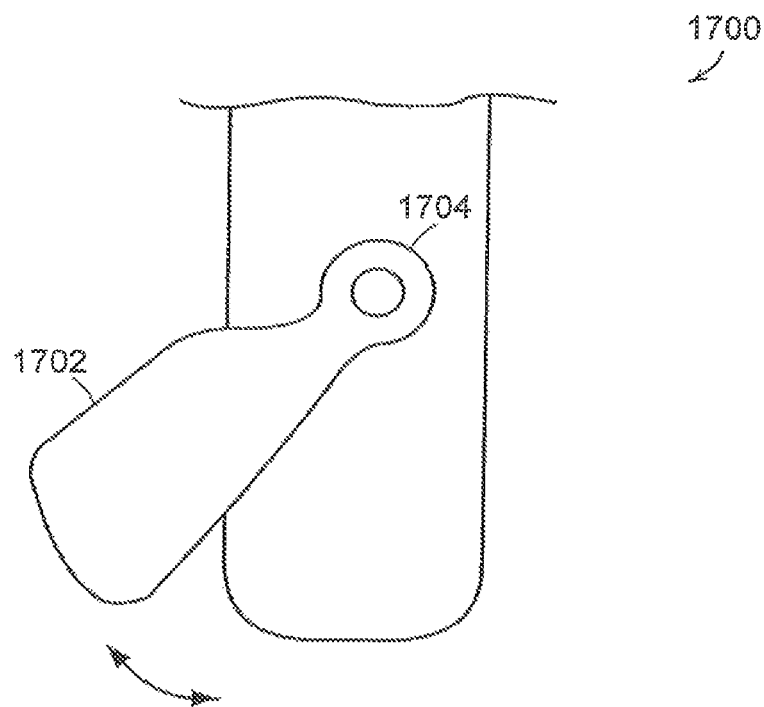
FIGS. 17D-17F illustrate optional blade features for some embodiments of retractors of the invention.
Figures 17E, 17F:
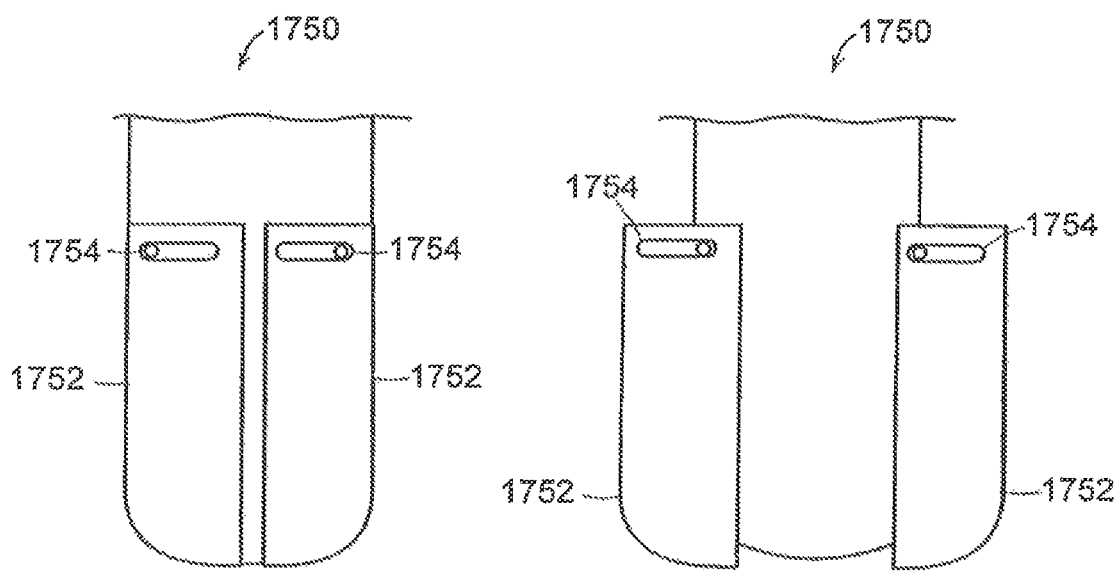

Optionally, the retractors of this invention include additional extensions at the distal ends of the blades or blade extensions. FIG. 17D illustrate the distal end of blade 1700, which includes pivoting extension 1702 that rotates about hinge 1704. FIGS. 17E and 17F illustrate another embodiment of an additional blade extension. Distal end of blade 1750 are slidably attached to two additional extensions 1752 by slides 1754. Optionally, additional extensions are fixable into a desired position.

Optionally, one or more surgical instruments are attached to the retractor to provide additional utility. Examples of such surgical instruments include surgical lighting source, a portion of a source for producing suction, or other surgical instruments that are known in the art, in some embodiments, surgical instruments are attached to an expandable frame with a mechanism for supporting surgical instruments. The surgical instruments can be attached prior to, at some intermediate state of; or after the expansion of the retractor. In some embodiments, the inner or outer face of the blades or blade extensions include longitudinal grooves or tracts which can be used to slide or otherwise guide surgical instruments down the length of the blades or blade extensions and into or near a surgical site.

Figure 18:
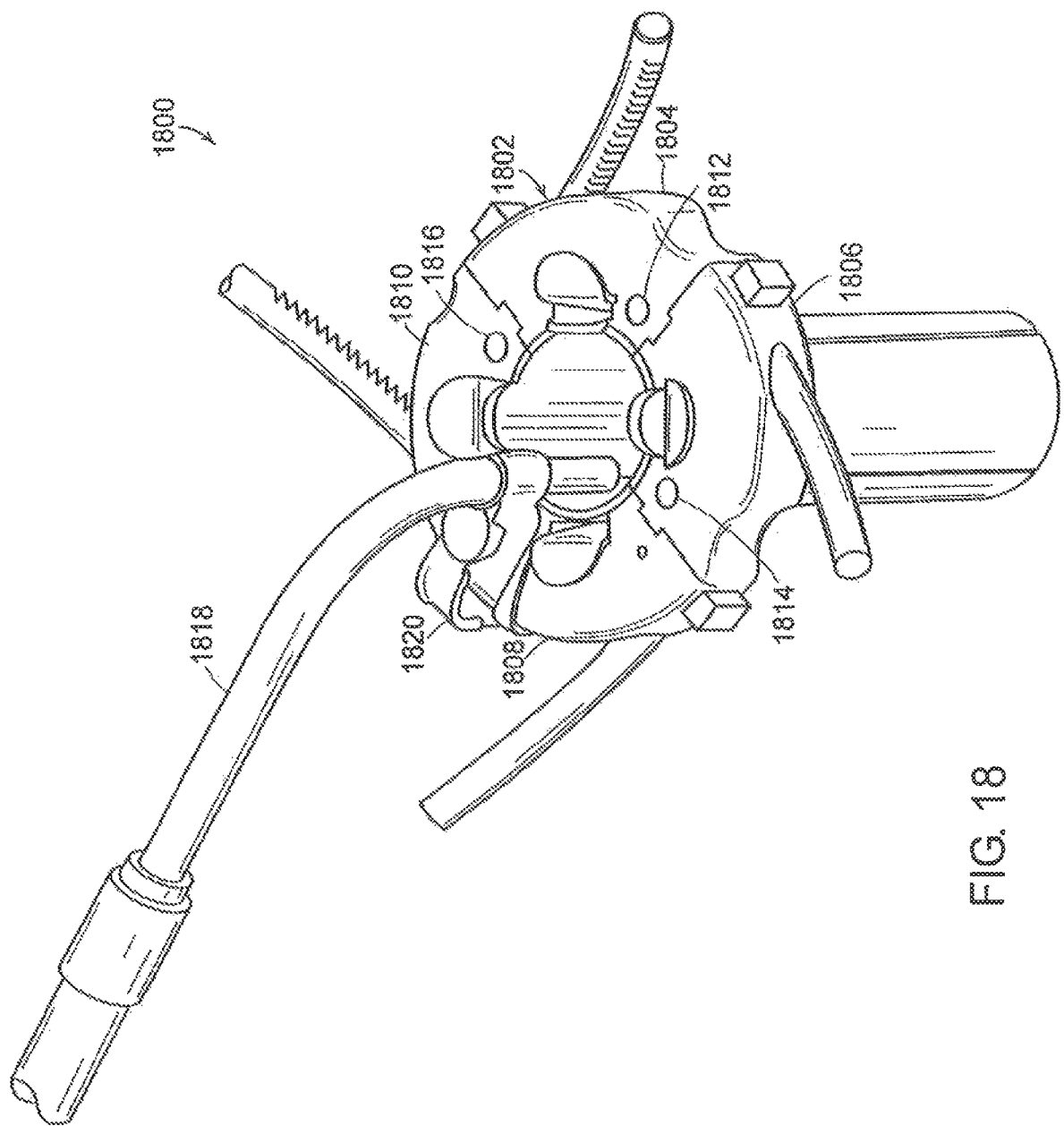
FIG. 18 illustrates one embodiment of a retractor of the invention.

FIG. 18 illustrates retractor 1800, which includes expandable frame 1802. Expandable frame 1802 includes base components 1804, 1806, 1808, 1810. Base components 1804, 1806, 1810 define attachment holes 1812, 1814, 1816, respectively. Light source 1818 is attached to base component 1808 with a mechanism for supporting surgical instruments that comprises instrument clip 1820 at an attachment hole on base component 1808.

Figure 19:
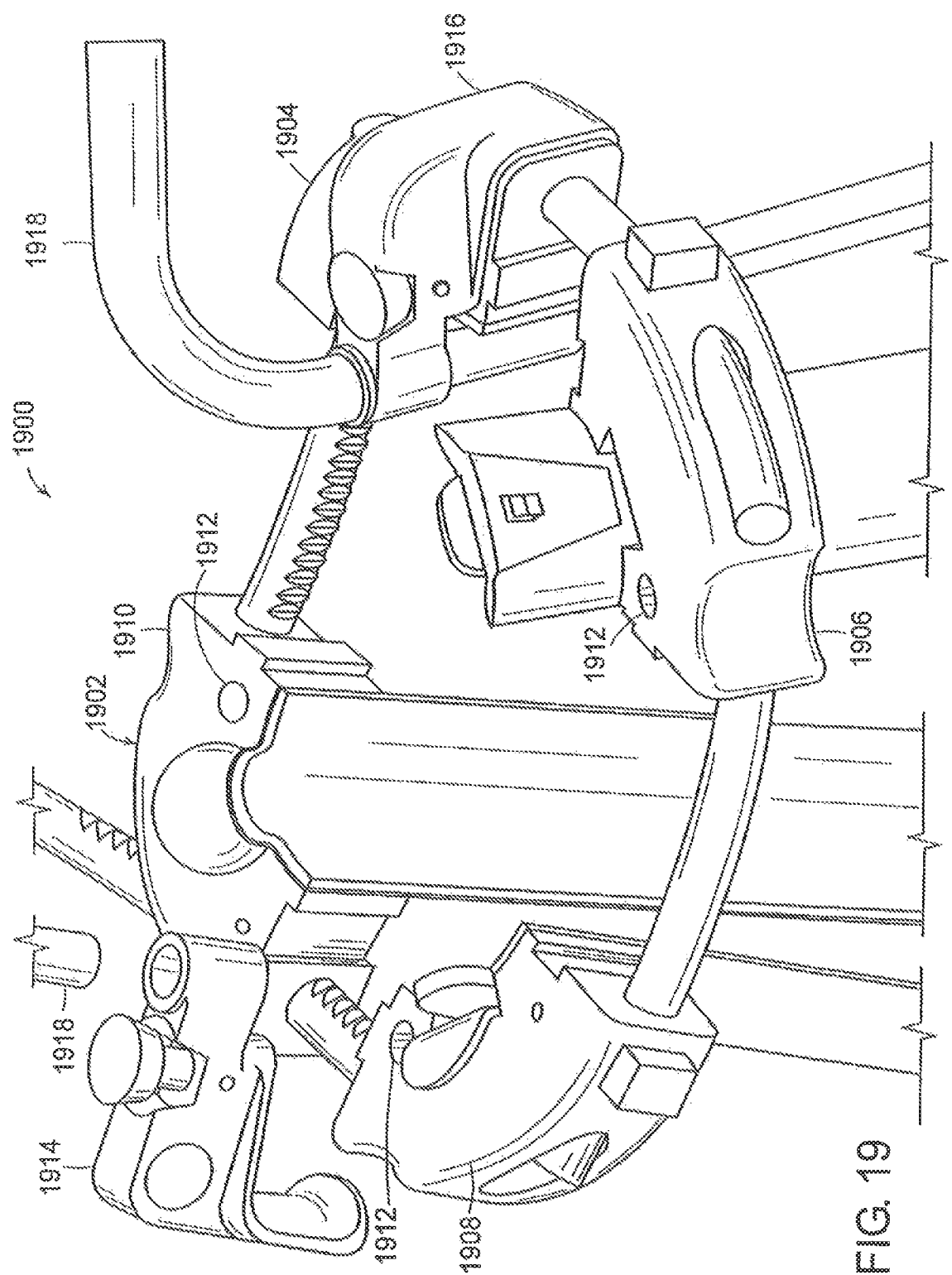
FIG. 19 illustrates one embodiment of a retractor of the invention.

FIG. 19 illustrates retractor 1900 which includes expandable frame 1902, Expandable frame includes base components 1904, 1906, 1908, 1910. Base components 1904, 1906, 1908, 1910 define attachment hole 1912, Attachment hole 1912 provides an attachment site for instrument clips 1914, 1916. Instrument clips 1914, 1916 secure instruments, such as surgical lighting source 1918, to the expandable frame.

Figure 20:
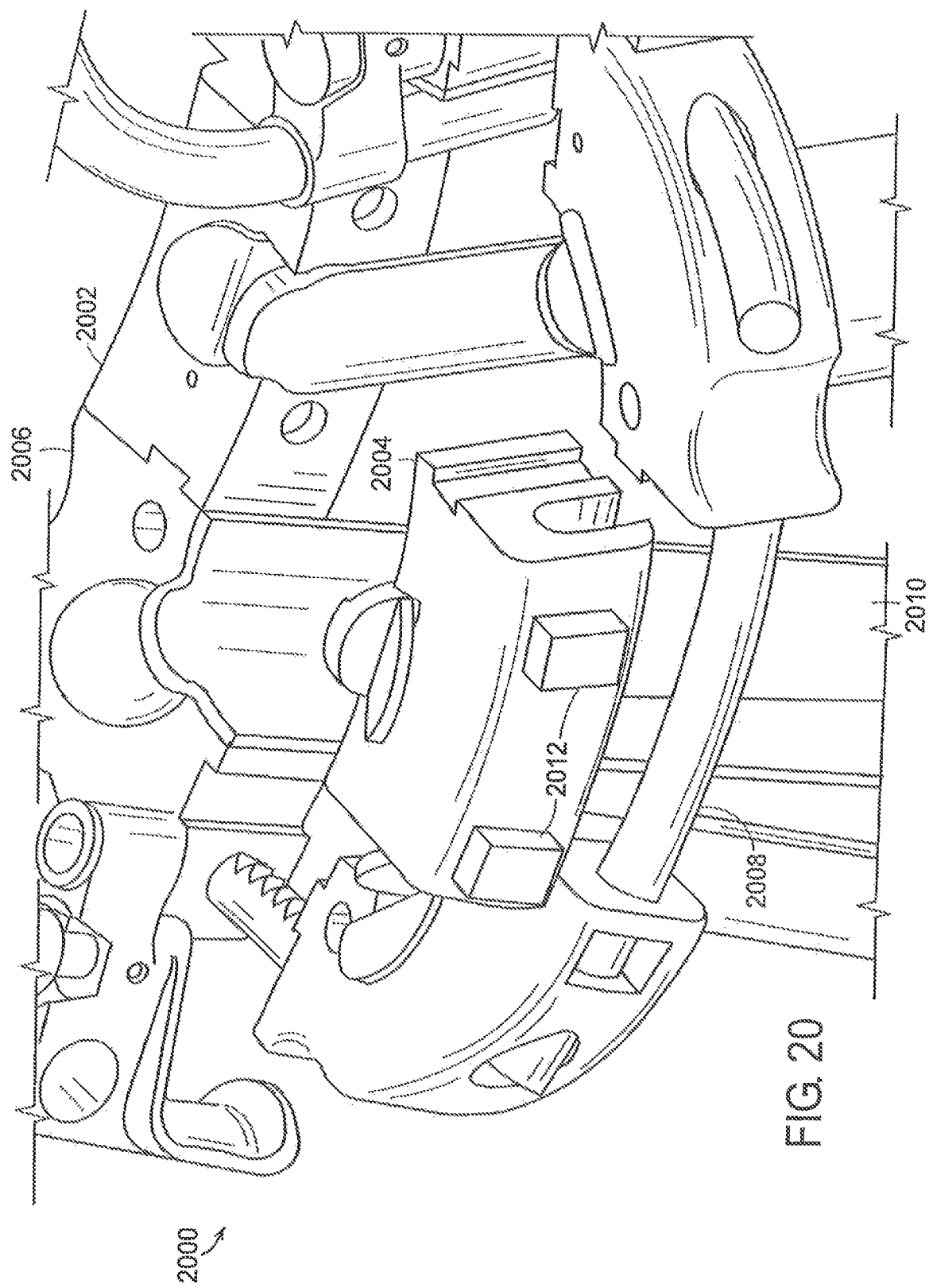
FIG. 20 illustrates one method of attaching additional blades to one embodiment of a retractor of an invention.

In some embodiments, extra blades are attached to the retractor to provide additional utility. FIG. 20 illustrates attachment of additional blades to retractor 2000, which includes base components 2002, 2004. Base components 2002, 2004 are attached to expandable frame 2006 along exposed ratchet arms, such as ratchet arm 2008. Base component 2004 includes blade 2010 and ratchet release buttons 2012. Ratchet release buttons 2012 secure base component 2004 at a relative position to ratchet arm 2008.

Figure 21A:
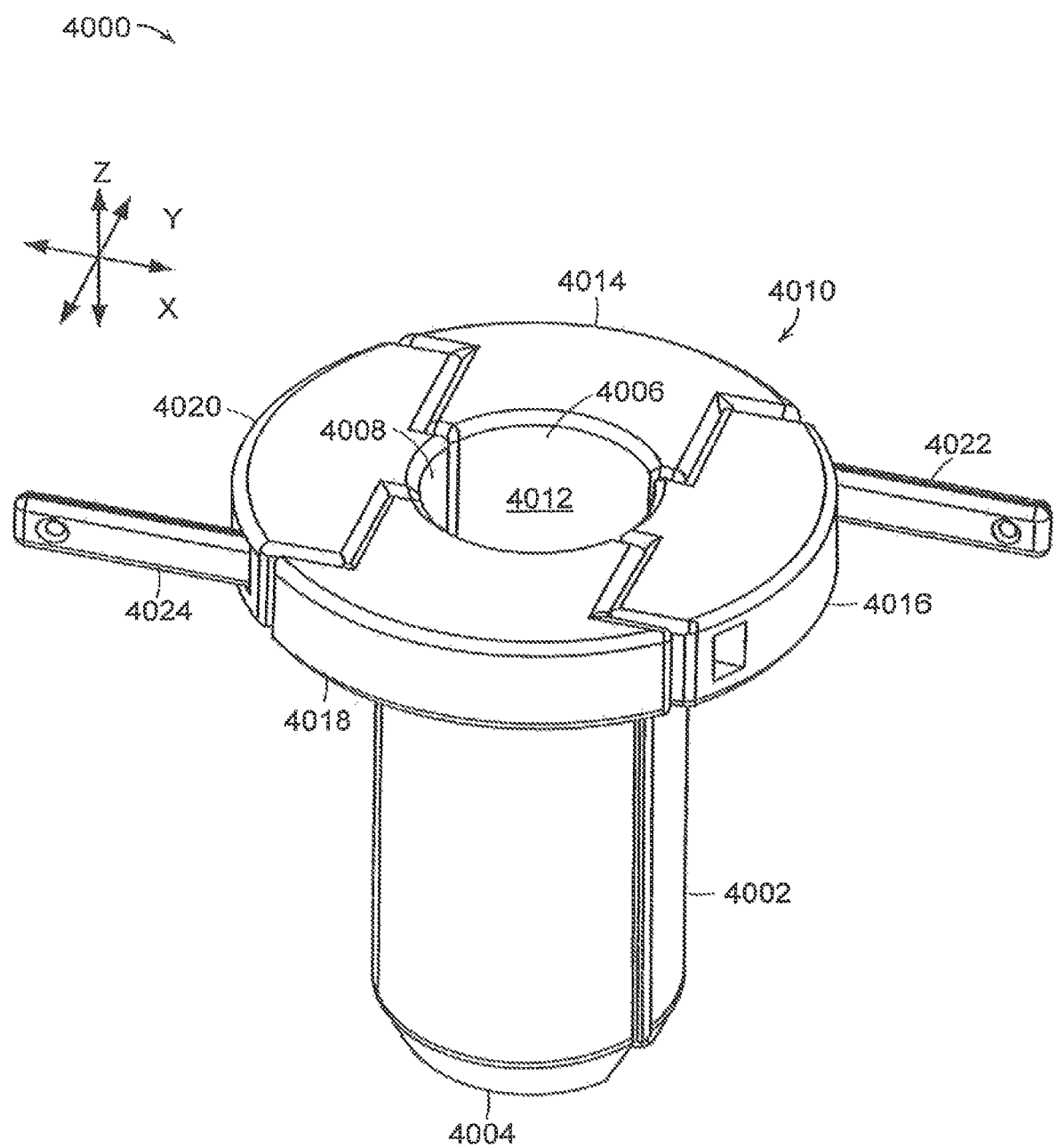
FIGS. 21A-21D illustrates one embodiment of a retractor of the invention.
Figure 21B:
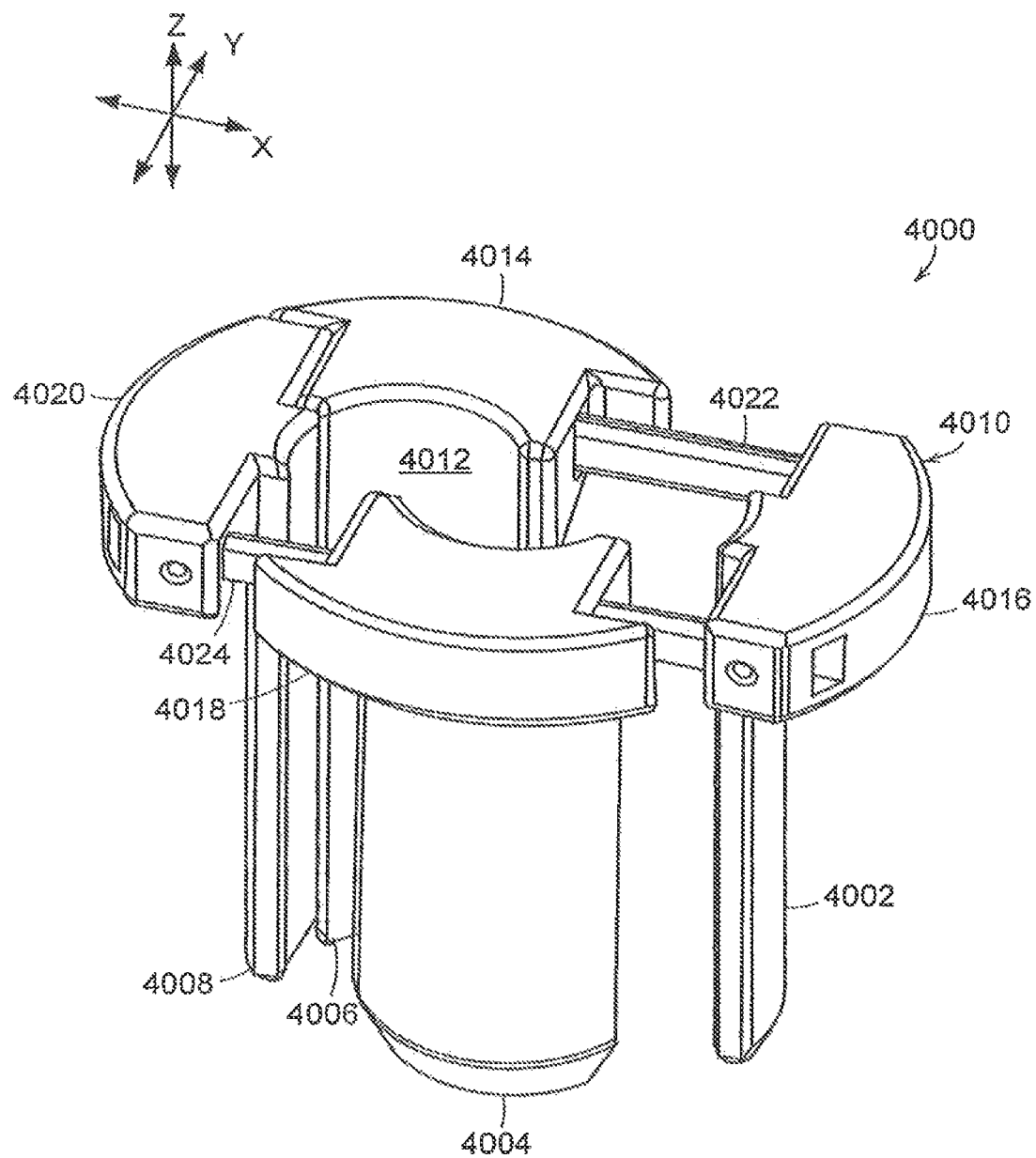
Figure 21C:
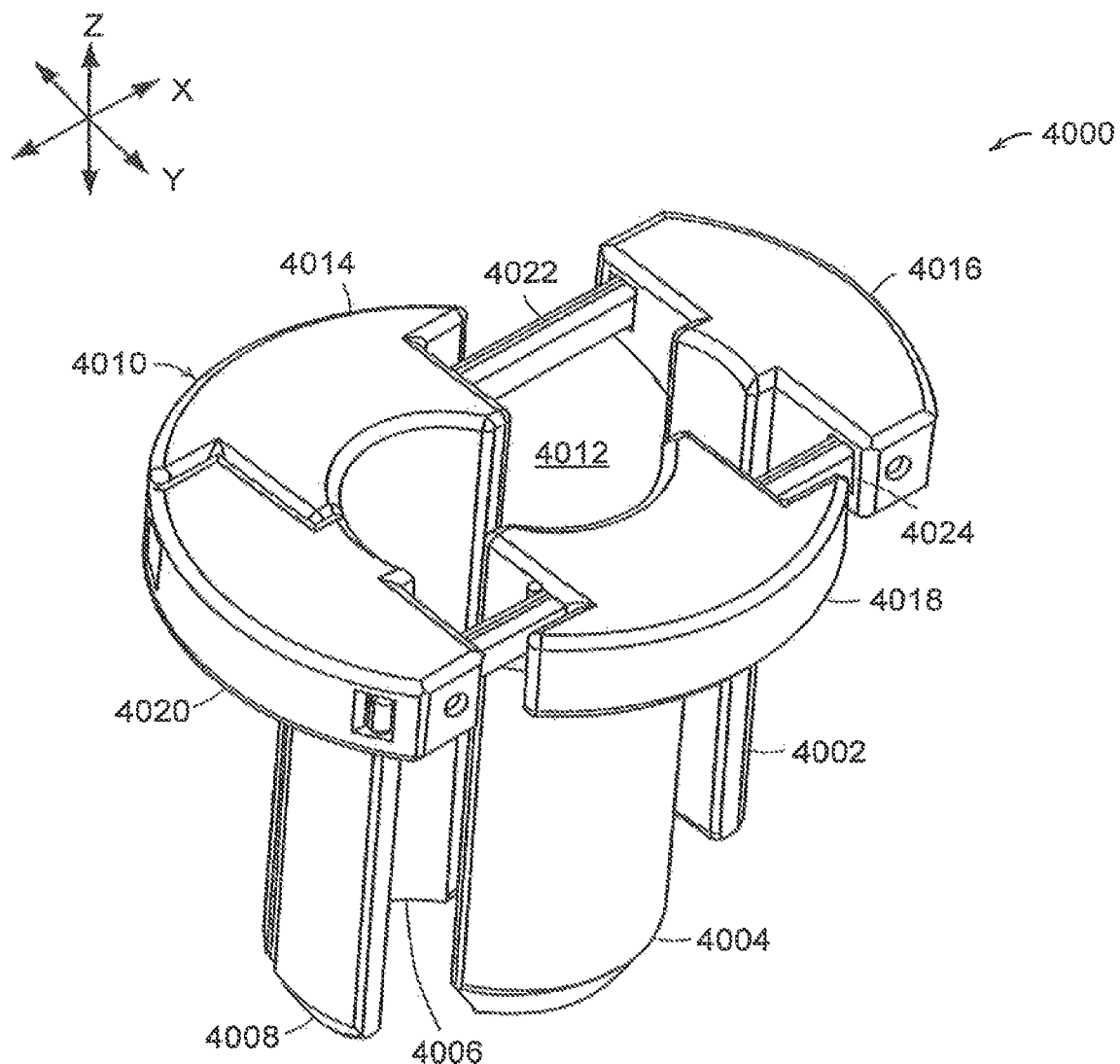
Figure 21D:
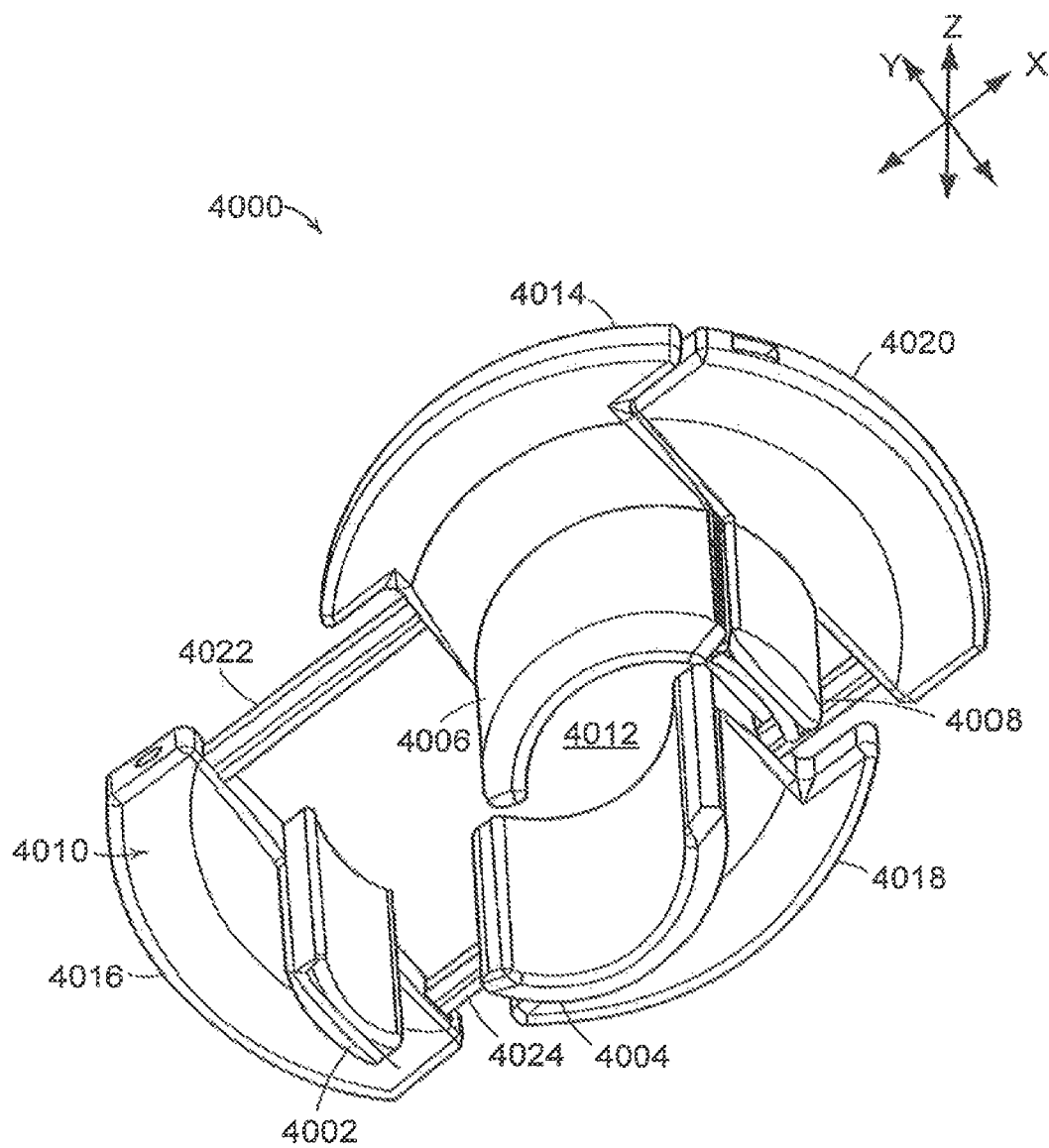

FIGS. 21A-21D illustrates retractor 4000 which is yet another embodiment of a retractor of the invention, FIG. 21A illustrates retractor 4000 in a first position in which the retractor is fully collapsed or contracted position. FIG. 21B illustrates retractor 4000 in a second position in which the retractor has been expanded or opened. FIG. 21C illustrates another view of retractor 4000 in the second position. FIG. 21D illustrates a bottom view of retractor 4000 in the second position.

Retractor 4000 includes expandable frame 4010 having a major plane parallel to the XY plane. Expandable frame 4010 comprises a first base component 4014, a second base component 4016, a third base component 4018, and a fourth base component 4020. While retractor 4000 is illustrated in FIGS. 21A-21D as having four base components, in other embodiments, the retractor comprises two, three, or more than four base components. Optionally, retractor 4000 includes at least one mechanism for supporting surgical instruments (not illustrated in FIGS. 21A-21D). Examples of suitable mechanisms for supporting surgical instruments include those that are described herein, such as instrument clips similar to that illustrated in relation to FIGS. 1, 2, and 18, or attachment grooves.

Base components 4014, 4016, 4018, 4020 are connected to one another using connectors that include two rods 4022, 4024. Rod 4022 connects first base component 4014, second base component 4016 and fourth base component 4020, and rod 4024 connects second base component 4016, third base component 4018, and fourth base component 4020. Rods 4022 and 4024 extend completely through first base component 4014 and third base component 4018, respectively. In the position illustrated in FIG. 21A, rods 4022 and 4024 also extend completely through second base component 4016 and third base component 4020, respectively. Base components 4016 and 4020 can translate along a length of rods 4022 and 4024. Base component 4014 can translate along a length of rod 4022 and base component 4018 can translate along a length of rod 4024.

The retractor also includes one or more mechanisms for fixing the position of one base component (not illustrated in FIGS. 21A-21D) relative to another base component. Examples of suitable mechanisms for fixing the position of one base component relative to another base component are described herein, and include the mechanisms for fixing the position of one base component relative to another base component that are illustrated in FIGS. 1-3, 6-8, and 9-12, as well as other ratchet, screw, or retaining mechanisms.

Retractor 4000 includes retractor blades 4002, 4004, 4006, and 4008, which are attached to base components 4016, 4018, 4014, and 4020, respectively. Retractor blades 4002, 4004, 4006, 4008 are arcuate or curved, and in the first position illustrated in FIG. 21A, their collective inner faces contact, thereby defining a conduit in the shape of a hollow circular cylinder having a smooth or substantially seamless profile. In some embodiments, the conduit can be an elliptical cylinder.

In some embodiments, at least a portion of retractor 4000 includes a radiolucent material. For example, a portion of the retractor can include radiolucent plastics, aluminum, thin stainless steel, titanium, nitinol, or cobalt chrome.

Optionally, the retractor blades can include integral sleeve inserts. For example, a retractor blade can include a blade extension that is telescopically and slidably attached to a retractor blade. The retractor can also include a blade extension fixation mechanisms that, when engaged, immobilizes a blade extension relative to the remainder of the retractor blade, Examples of blade extensions and fixation mechanisms are described herein, such as in relation to FIGS. 13A-13C, 16, and 17D-17F.

In some embodiments, one or more of the retractor blades has a toe-out protrusion which allows the blades to grip tissue and provides for better retraction of tissue. Examples of such a toe-out protrusion are described herein, such as in relation to FIG. 14.

The major axis of retractor blades 4002, 4004, 4006, 4008 are normal to the major plane of the expandable frame. In some embodiments, one or more of the blades are attached to the expandable frame such that the blade is rotatable about the major axis of the blade and fixable at a desired point of rotation about the major axis. For example, a blade can be attached to the base component with a vertical hinge that allows the blade to be rotated from side to side. In other embodiments, one or more of the blades are attached to the expandable frame in such a way that the blade is rotatable about an axis that is parallel to the major plane of the expandable frame. For example, a blade can be attached to the base component with a horizontal hinge that allows the blade to be rotated up and down.

Retractor 4000 is bisected by at least two planes that are substantially normal to the major plane XY. A first plane is parallel to the XZ plane and bisects retractor 4000, running approximately between base components 4014 and 4018 and bisects base components 4016 and 4020. A second plane is parallel to the YZ plane and bisects retractor 4000, running approximately between base components 4016 and 4020 and bisects base components 4014 and 4018.

In the contracted position illustrated in FIG. 21A, the inner diameter of access portal 4012, defined by base components 4014, 4016, 4018, 4020 of expandable frame 4010, is reduced in size relative to its size in the positions illustrated in FIGS. 21B-21D. This allows retractor 4000 to be inserted into an organism or surgical patient (e.g., a human or other mammal) through an incision of minimal size.

Once retractor 4000 has been inserted into the desired anatomical location, retractor 4000 can be expanded or deployed. For example, a spreader instrument (such as the one described in relation to FIGS. 26-28) can be used to open the distal ends of the retractor blades. Retractor 4000 can be used to retract and hold muscle at an angle that is about perpendicular to the greatest muscle force, thereby allowing for better or optimal placement of retractor blades due to anatomical constraints and reducing the problems associated with tissue creep which are caused by muscle and other tissue not being restrained from the working channel.

FIG. 21B illustrates retractor 4000 in a partially expanded, or partially translated, position. To expand retractor 4000 from the position illustrated in FIG. 21A to the position illustrated in FIG. 21B, force is applied to expandable frame 4010 to move base component 4016 along rod 4022 and relative to base component 4020 and rod 4024. A stop (not shown) located at the ends of rods 4022 and 4024 prevents attached components from translating off of the ends and disengaging the rods. Base components 4014 and 4018 can be slideably positioned at a desired position along rods 4022 or 4024, respectively. In this manner, expandable frame 4010 moves approximately in, or parallel to, the major plane from a first position (i.e., the one illustrated in FIG. 21A) to a second position (i.e., the one illustrated in FIG. 21B) substantially along the first plane and generally away from the second plane. Optionally, additional base components with or without retractor blades can be secured to rods 4022, 4024.

If desired, expandable frame 4010 is able to be expanded or contracted to many different positions by moving one or more of base components 4014, 4016, 4018, 4020 along one of rods 4022, 4024. In this way, retractor 4000 can be expanded or contracted to a wide variety of desired positions.

Rods 4022, 4024, as shown, are straight, so movement of the base components does not cause an asymmetric or uneven expansion and contraction of the retractor. In other words, expansion and contraction of the expandable frame results in an equal amount of expansion and contraction of the distal ends of the blades and the base components remain coplanar with one another or arranged flat in the major plane XY.

In other embodiments, the shape of the rods or other connector is chosen in order to produce a desired degree of asymmetric or curved expansion such that the expandable frame defines an access portal having an average diameter that is smaller than the greatest distance between the distal ends of any two blades when the expandable frame is in the second position. In some embodiments, one or more portions of the expandable frame are not substantially coplanar at one or more positions or degrees of expansion and contraction.

In some embodiments, the blades and/or blade extensions add additional structural rigidity to the expandable frame when the expandable frame is at one or more positions. For example, interlocking blades or blade extensions can be mechanically connected to one another along some portion of their edges or sides, thereby providing additional structural rigidity.

The retractors of this invention can be constructed of many different types of material, including a wide range of polymers, metals (e.g., titanium), and metal alloys (e.g., stainless steel, cobalt chrome, and titanium alloys). Some portions of the retractor may require a strong, rigid material (e.g., the bases, ratchet arms, and hinges of the expandable frame). Other portions of the retractor may require a flexible, durable material in order to withstand repeated distortions (e.g., a flexible tab of a fixing mechanism). Preferably, the materials of construction are biocompatible.

Additionally, the materials of construction can be chosen to provide favorable characteristics or lend additional advantages during some portion of the surgical process. For example, it is often necessary to take X-ray images and/or fluorimages of a subject during surgery. Hence in some embodiments, at least a portion of the retractor is constricted of radiolucent materials. However, it can be beneficial to have a reference point for a marker on an X-ray image. So in other embodiments, at least a portion of the retractor is made from a material that is radiopaque.

In some embodiments, this invention includes a method of forming a surgical site in an organism (e.g., a human or other mammal). In one embodiment, the method comprises the steps of a) creating an incision in the skin of a mammal; b) retracting the tissue of the mammal, at the incision with a retractor of this invention to form a surgical site.

In some embodiments, the surgical site is formed at a spinal column. In further embodiments, the surgical site is formed during a surgical procedure that includes at least one member of the group consisting of a transforaminal lumbar interbody fusion procedure, a posterior lumbar interbody fusion procedure, a posterolateral fusion procedure, and other approaches (e.g., anterior, lateral, anterior-lateral, and other areas of the spine such as, for example, cervical or thoracic areas). The retractors of this invention are also suitable for use in nonspinal surgical procedures.

In some embodiments, an obtruator is inserted into the incision before the retractor is inserted. In further embodiments, one obtruator and subsequent dilators are inserted to dilate the incision before the retractor is inserted.

Optionally, the retractor is assembled to an insertion tube before it is inserted into the organism. An insertion tube provides for easier insertion of a retractor into, and positioning within, an organism. In some embodiments, the insertion tube attaches to the expandable frame of a retractor.

Figure 22A:
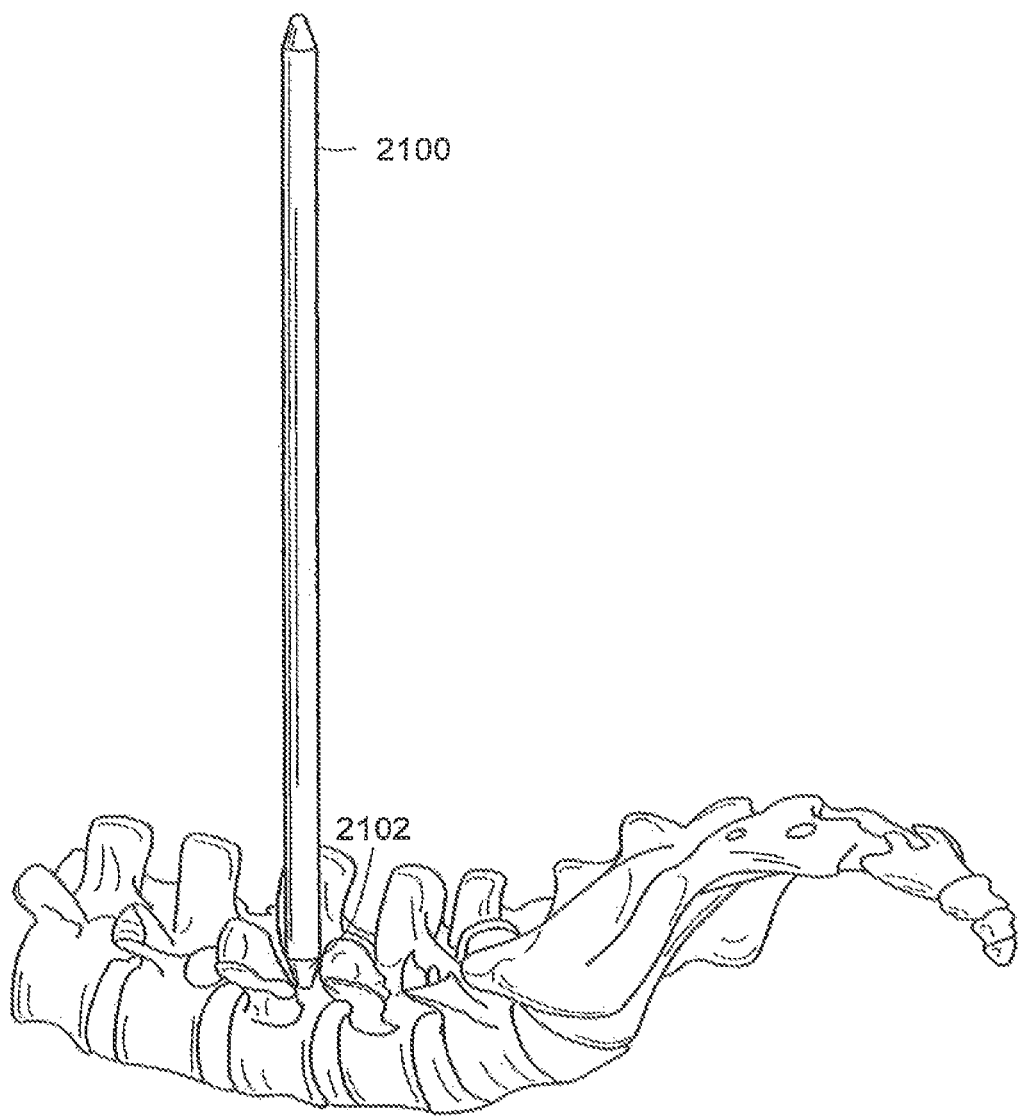
FIGS. 22A-22H illustrate one embodiment of a method used to retract tissue near the spine of a human.

In some embodiments, the retractor is inserted over an obtruator during insertion of the retractor to the depth of the surgical site or near the depth of the surgical site to be formed. FIGS. 22A-22H illustrate one embodiment of such a method used to retract tissue near the spine of a human. Soft tissue and some bone mass has been omitted from the figures for clarity, FIG. 22A illustrates obtruator 2100 after it has been inserted into an incision and forced down to the surgical site (i.e., next to the spinal column). Optionally, the obtruator is directed along a guide wire which has previously been tethered to the surgical site.

Figure 22B:
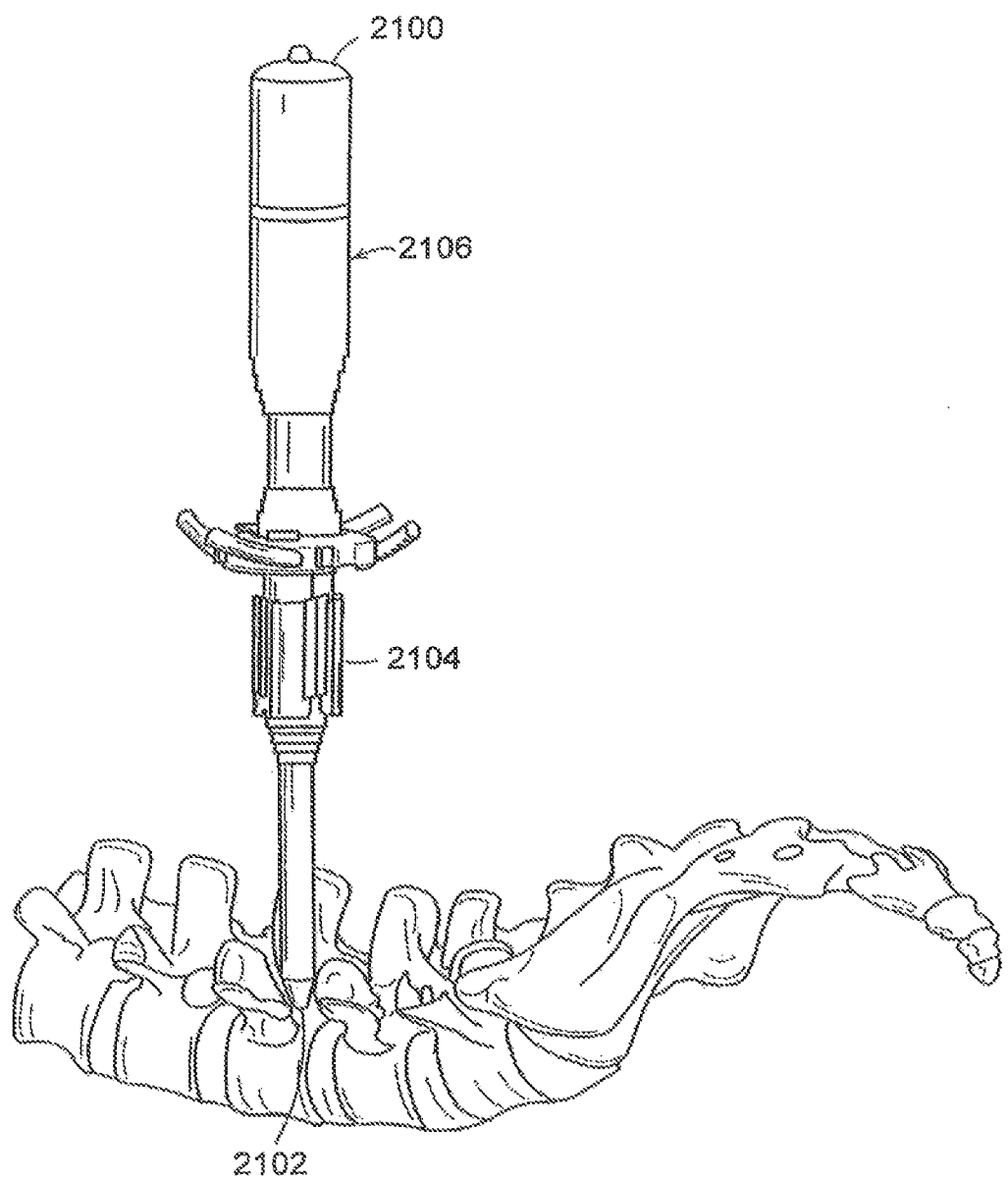

Once obtruator 2100 is in position at surgical site 2102, retractor 2104 is assembled to insertion tube 2106. The combined assembly of retractor 2104 and insertion tube 2106 defines a conduit that has an inner diameter that is greater than the outer diameter of obtruator 2100. This allows the combined assembly of retractor 2104 and insertion tube 2106 to, in turn, be assembled over obtruator 2100, as shown in FIG. 22B.

Figure 22C:
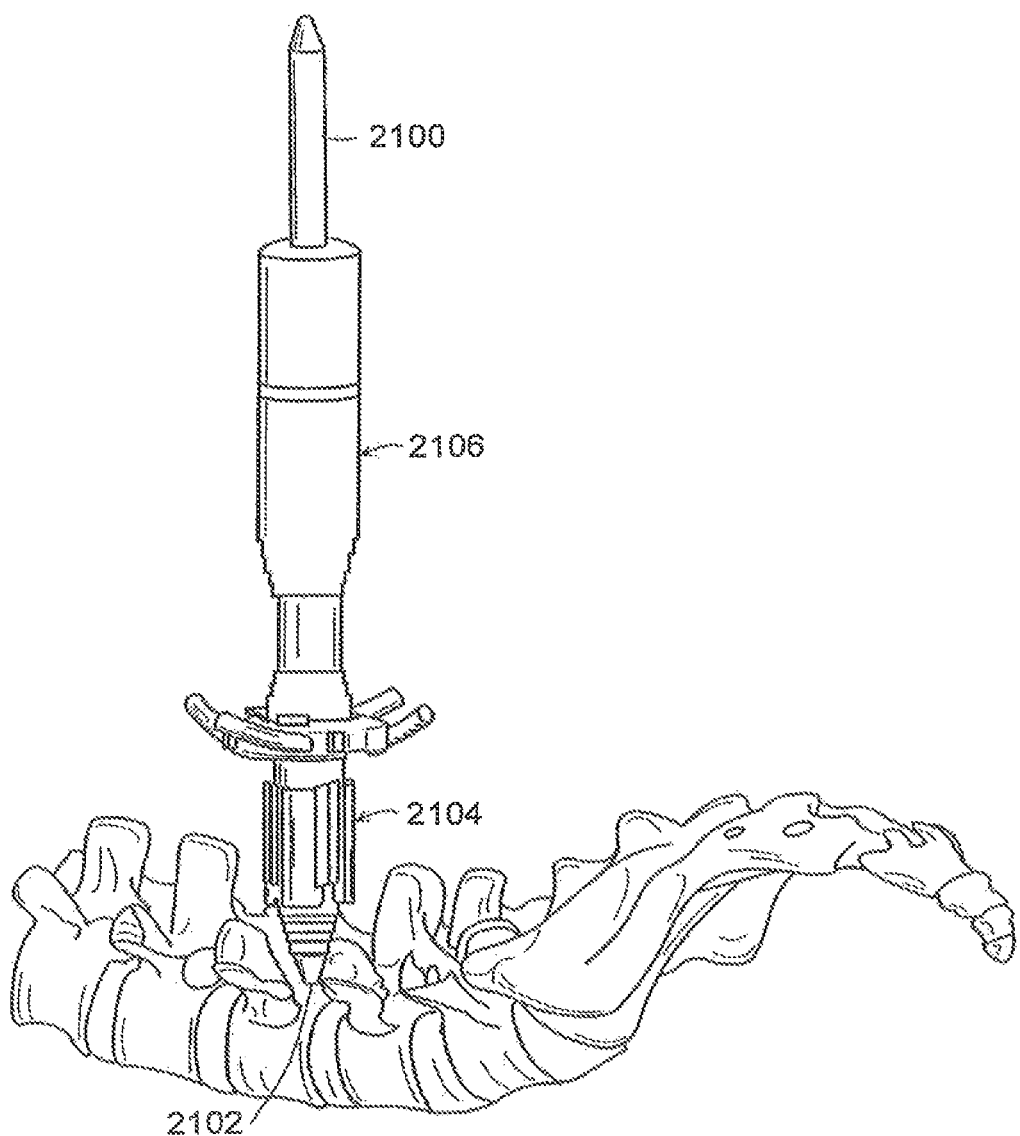
Figure 22D:
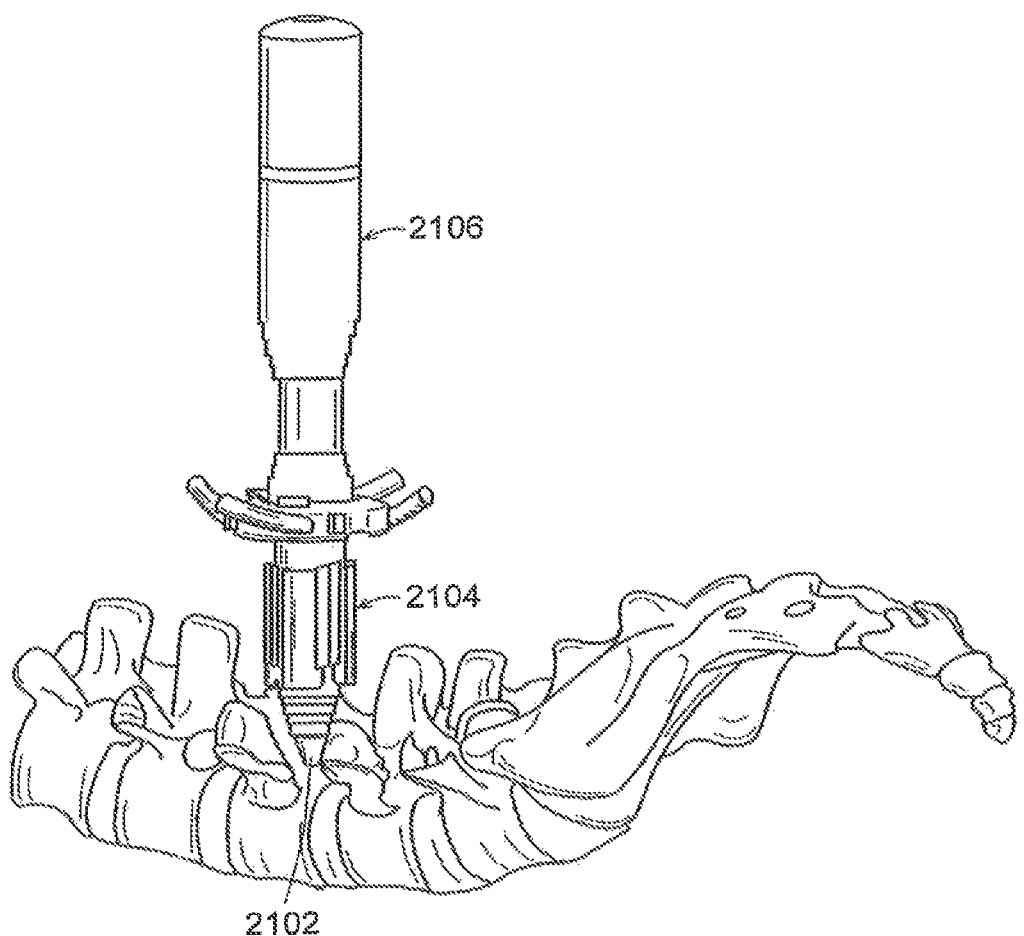

Once retractor 2104 is assembled over obtruator 2100, a surgeon or other practitioner of this embodiment pushes retractor 2104 down the length of obtruator 2100 to surgical site 2102 by applying force on insertion tube 2106, as shown in FIG. 22C. Once retractor 2104 is at surgical site 2102, obtruator 2100 is removed from the incision, leaving retractor 2104 in the incision and attached to insertion tube 2106, as shown in FIG. 22D.

Figure 22E:
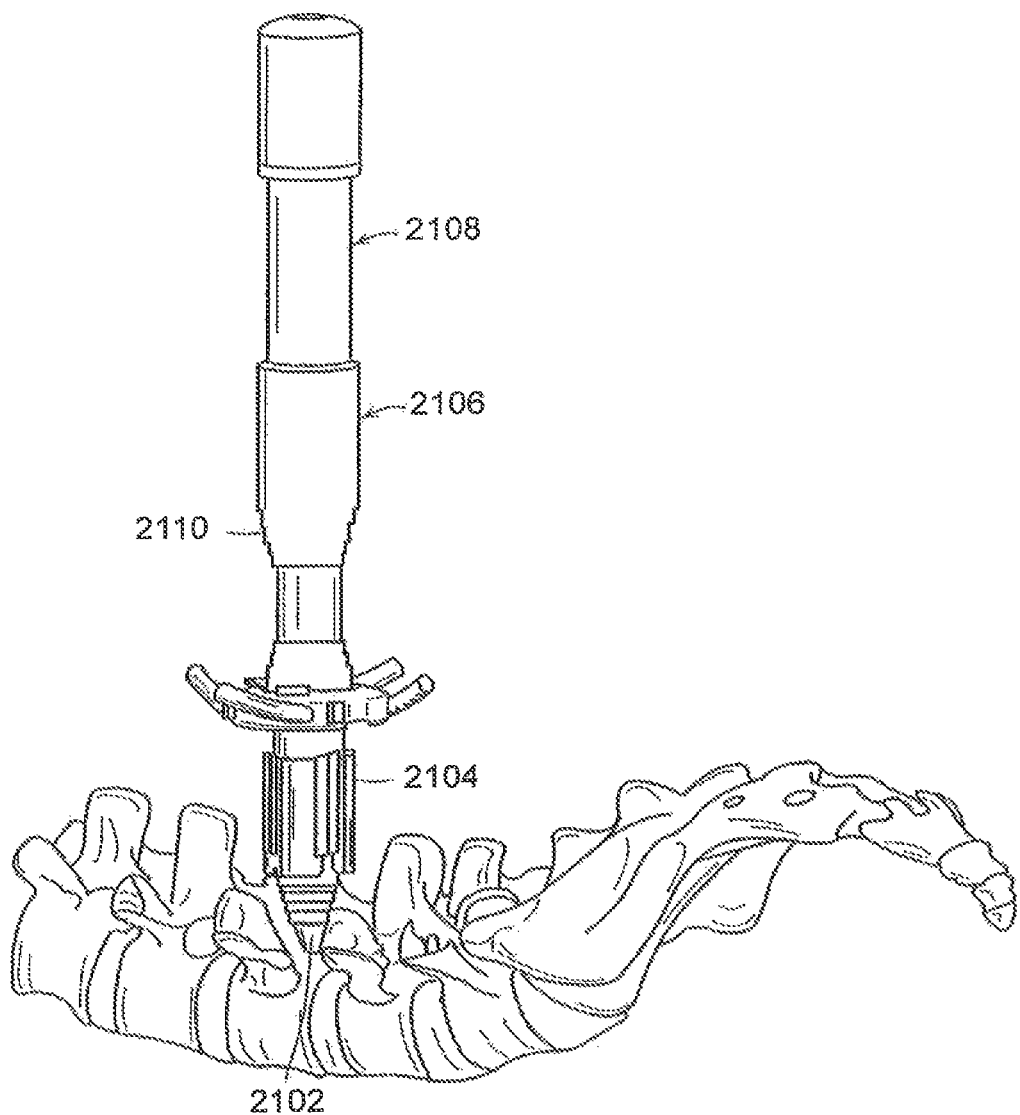
Figure 22F:
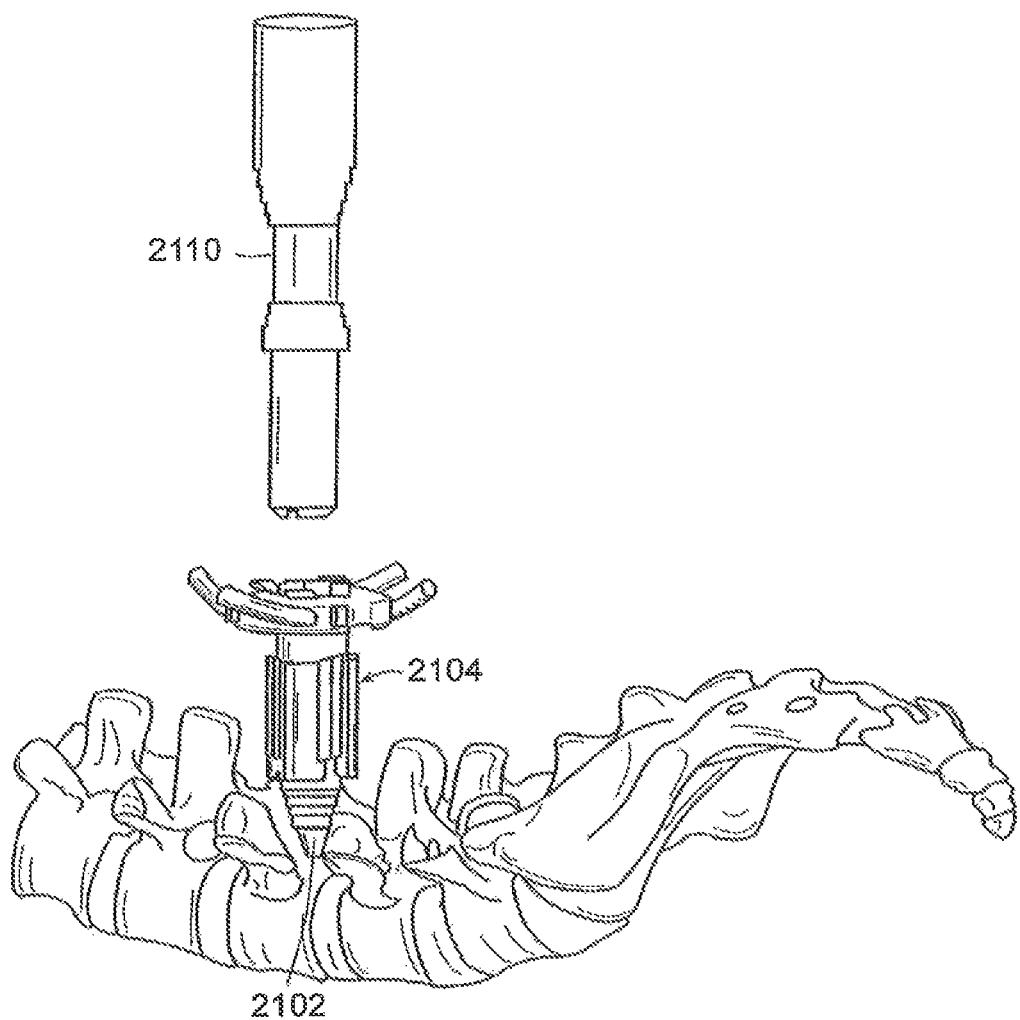

Outer sleeve 2110 contacts the frame and is used to position retractor 2104 to a desired depth and position (e.g., to the surgical site or above the surgical site to allow sufficient room for extension of the blade extensions). Alternatively or in addition, outer sleeve 2110 captures the proximal end of the blades that are inserted into the dovetail feature of the proximal end of retractor 2104. Inner sleeve 2108 is used to insert blades and/or blade extensions onto the retractor or to extend one or more blade extensions to a desired extent. Alternatively or in addition, inner sleeve 2108 is used to capture the distal end of the blade to prevent the blades from splaying when inserted into the incision. Blades and/or blade extensions can be inserted or positioned in any desired order or combination (e.g., all blades or extensions inserted or positioned simultaneously or individually). Inner sleeve 2108 is then removed from insertion tube 2106, as shown in FIG. 22E, followed by the outer sleeve 2110, as shown in FIG. 22F.

Figure 22G:
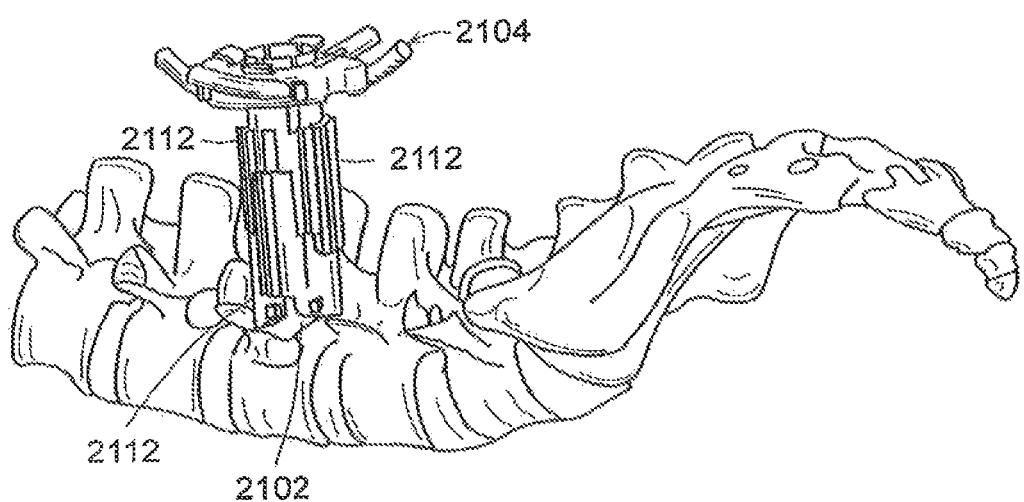

When all the portions of the insertion tube 2106 have been disassembled from retractor 2104, one or more blade extensions 2112 can be extended to a desired extent around the surgical site 2102, as shown in FIG. 22G. As shown in FIG. 22G, blade extensions 2112 are attached to the outer face of the blades of retractor 2104, however, in some embodiments, the blade extensions are attached to the inner face of the blades.

Figure 22H:
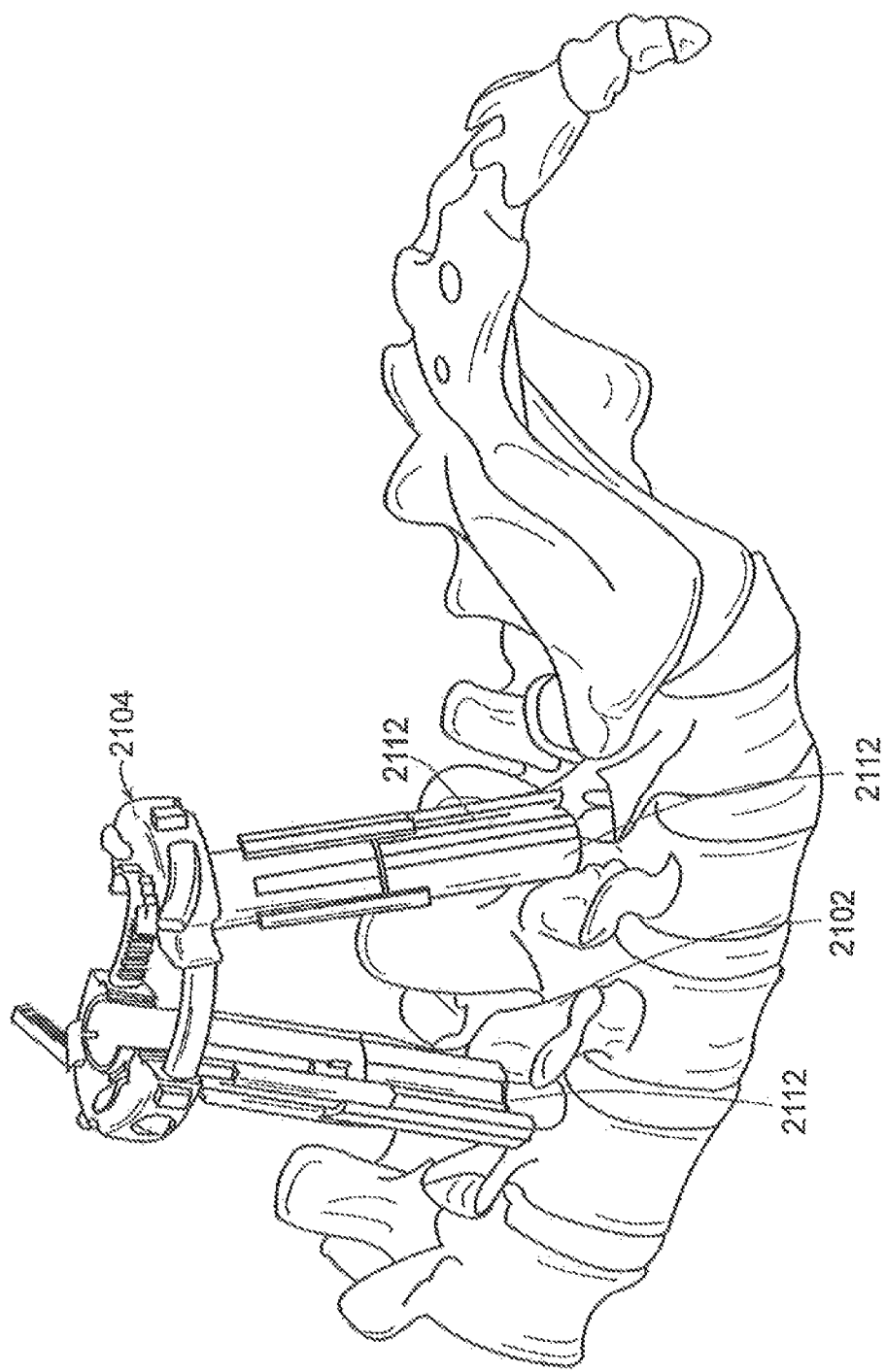

Finally, the expandable frame of retractor 2104 is moved to a desired position, such as the one shown in FIG. 22H. The surgical site is formed by the distal ends of the blades and/or blade extensions 2112. Optionally, the retractor is attached to a surgical retractor positioning mechanism (e.g. one or more rigid arms, not shown) which rigidly secures the refractor in the desired location.

Figure 23:
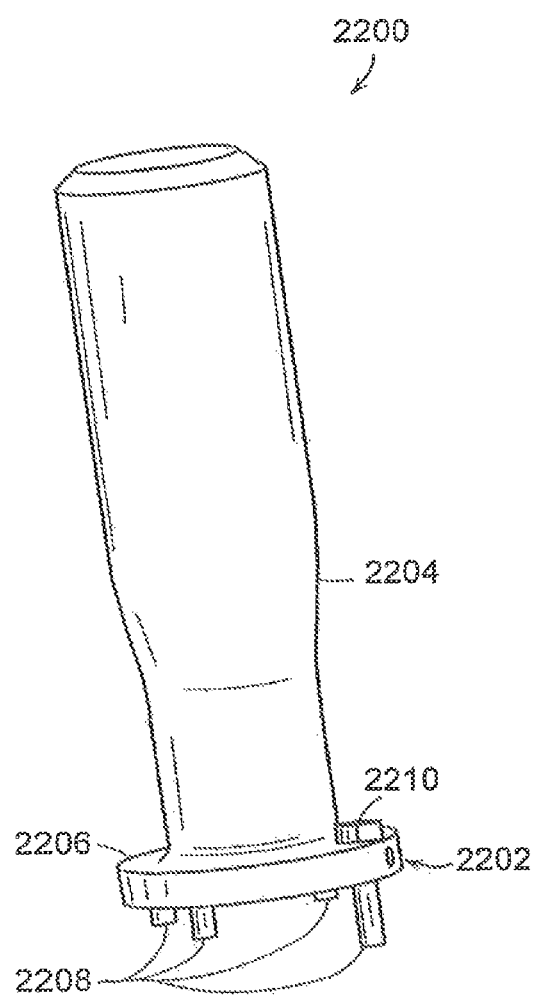
FIG. 23 illustrates one embodiment of an insertion tube.

FIG. 23 illustrates one embodiment of an insertion tube. Insertion tube 2200 includes attachment portion 2202, handle portion 2204, and stop 2206. Attachment portion 2202 includes various attachment prongs 2208 which are arranged in a pattern so as to match the top surface of an expandable frame. Handle portion 2204 provides a convenient place for a surgeon or other practitioner of this invention to apply force to an attached retractor. Stop 2206 ensures that a hand of a practitioner will not slip off of the handle portion 2204 as force is applied to insert and/or position an attached retractor. Stop 2206 includes lock 2210, which locks and secures one or more attachment prongs 2208 to a retractor. In some embodiments, the attachment prongs of an insertion tube provide a slight amount of resistance when secured to a retractor so the insertion tube remains attached during insertion of the retractor.

Figure 24:
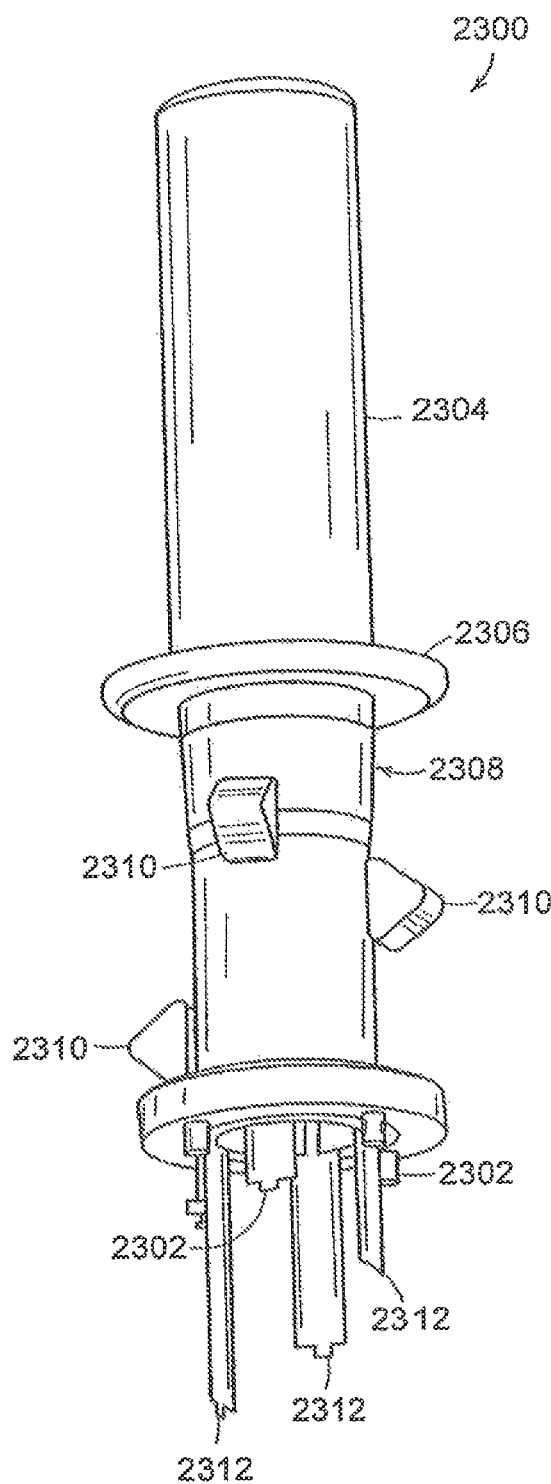
FIG. 24 illustrates another embodiment of an insertion tube.

FIG. 24 illustrates another embodiment of an insertion tube. Insertion tube 2300 includes attachment portions 2302, handle portion 2304, and stop 2306, all of which serve similar functions to the analogous portions in the embodiment of FIG. 23. However, insertion tube 2300 includes blade extension portion 2308, which includes one or more extender tabs 2310, which are mechanically connected to blade extender attachments 2312. By pushing sliding extender tabs 2310, a practitioner can lengthen blade extender attachments 2312 which are mechanically couple with one or more blade extensions in an attached retractor. In this manner, insertion lube 2300 allows a practitioner to insert a retractor, position a retractor, and/or extend one or more blade extenders to a desired telescopic length.

Figure 25:
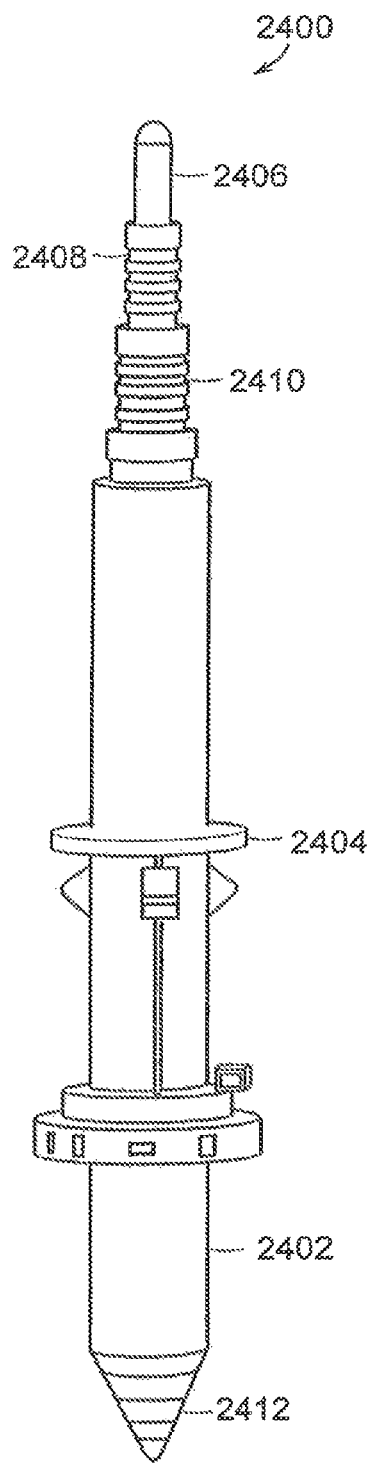
FIG. 25 illustrates one embodiment of an assembly of the invention that includes a retractor positioned over an obtruator and a series of dilators.

In some embodiments, a retractor of the invention is assembled (e.g., mechanically attached, or slipped or positioned over) to one or more obtruator and dilators before insertion into an organism. FIG. 25 illustrates such an assembly. Assembly 2400 includes retractor 2402, an insertion tube 2404, an obtruator 2406, and dilators 2408 and 2410.

Figure 26:
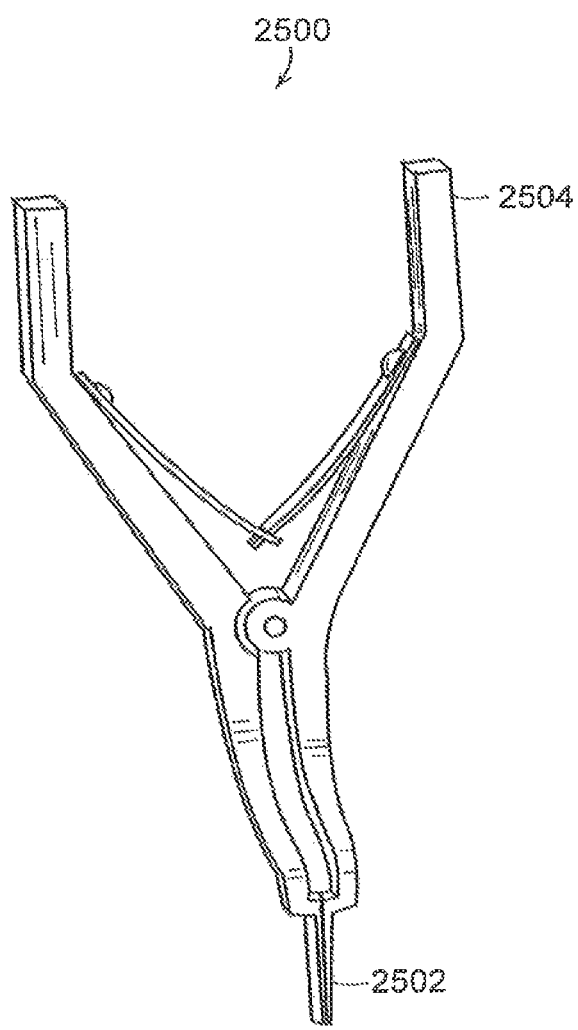
FIG. 26 illustrates one embodiment of a distraction instrument.

Once a retractor of the invention has been positioned in desired position relative to a surgical site, the expandable frame is moved to a desired position in order to form the surgical site. Optionally, one or more distraction instruments are used to move the expandable frame and retract tissue from the surgical site. FIG. 26 illustrates one embodiment of a distraction instrument. Distraction instrument 2500 has an attachment portion 2502 and a gripping portion 2504, Applying force to gripping portion 2504 causes attachment portion 2502 to splay or expand. By connecting attachment portion 2502 to a retractor, the application of force to the gripping portion will move an expandable frame into a desired position. In some embodiments, the attachment portion is attached to the outer diameter of the retractor, while in other embodiments it is attached to an inner diameter of the retractor (as illustrated in FIGS. 27 and 28).

In some embodiments, the expandable frame is expanded or contracted with the use of one or more keys or screws that engage the teeth on one or more ratchet arms and cause one or more base components to move relative to a ratchet arm. This provides for independent adjustment or each ratchet arm to a desired position or desired extent of expansion.

Figure 27:
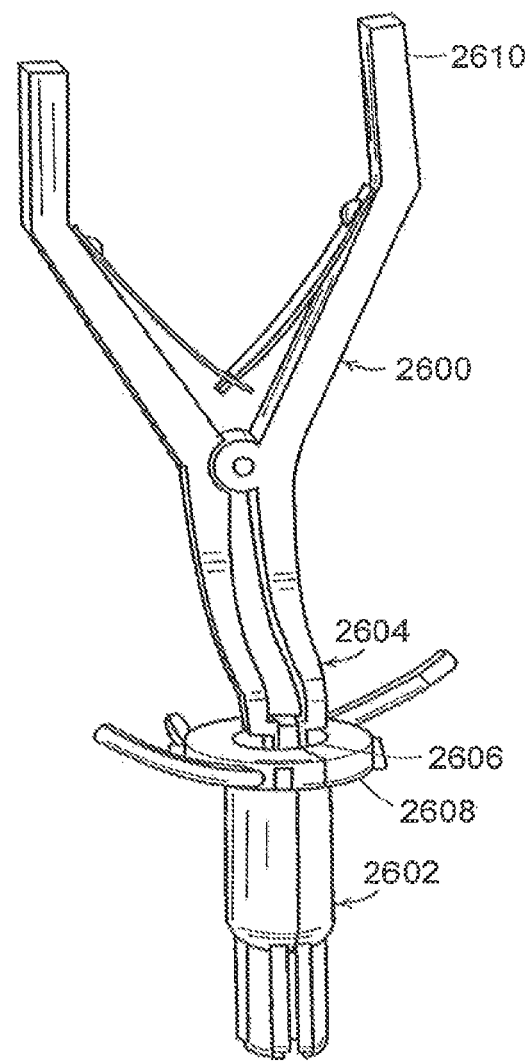
FIGS. 27 and 28 illustrate one method of expanding one embodiment of a retractor of the invention with one embodiment of a distraction instrument.
Figure 28:
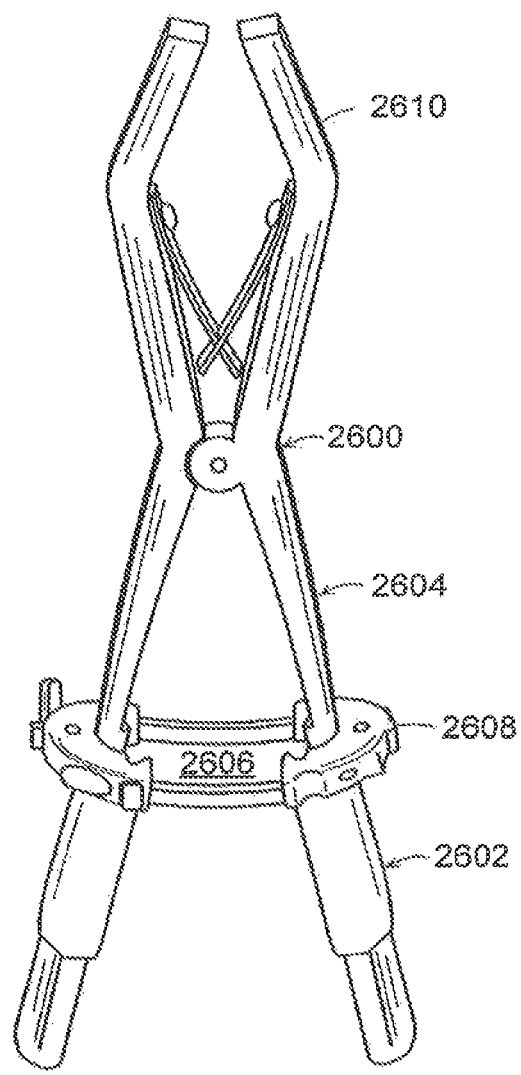

FIG. 27 illustrates the attachment of distraction instrument 2600 to retractor 2602. Attachment portion 2604 attaches to an inner diameter of access portal 2606 of expandable frame 2608. Squeezing gripping portion 2610 together causes attachment portion 2604 to splay, as illustrated in FIG. 28, thereby moving expandable frame 2608 into a desired position.

In some embodiments, this invention includes a method of forming a surgical site in an organism. In one embodiment, the method comprises the steps of creating an incision in the organism and retracting the tissue of the organism at the incision with a retractor of the invention to form a surgical site, thereby forming a surgical site defined at least in part by the distal ends of the blades. In some embodiments, the organism is a mammal. In further embodiments, the mammal is a human.

In some embodiments, the surgical site is formed near a spinal column. In further embodiments, a surgical site is formed during a surgical procedure that includes at least one member of the group consisting of a transforaminal lumbar interbody fusion procedure, a posterior lumbar interbody fusion procedure, and a posterolateral fusion procedure.

In some embodiments, the incision is first dilated with at least one obtruator before inserting the retractor. In a further embodiment, a retractor is inserted over the obtruator during insertion of the retractor to the depth of the surgical site to be formed.

Optionally, the refractor is attached to a surgical retractor positioning mechanisms that rigidly secures the retractor in a desired location. One example of a positioning mechanism is an adjustable rigid arm that attaches to a surgical table.

In some embodiments, this invention includes an assembly comprising a surgical retractor assembled to at least one obtruator. For example, this invention includes a surgical retractor which is mechanically attached to an obtruator. Optionally, the surgical refractor is not mechanically or rigidly attached to an obtruator, but is positioned or slid over an obtruator.

In another embodiment, this invention includes a surgical retractor, comprising an expandable frame that includes at least two base components, and at least one connector that connect the base components, wherein at least one base component is moveable along the connector; and at least two retractor blades attached to the expandable frame, wherein each blade has a proximal end attached to expandable frame, a distal end opposite the proximal end, and a major axis. Upon movement of the connector relative to at least one base component, the expandable frame moves from a first position to a second position, thereby increasing the average distance between two base components to a first distance and increasing the average distance between the distal ends of two retractor blades to a second distance, wherein the first distance is less than the second distance.

In another embodiment, this invention includes a surgical retractor, comprising an expandable frame that includes at least two base components, and at least one connector that connect the base components, wherein at least one base component is moveable along the connector; and at least two retractor blades attached to the expandable frame, wherein each blade has a proximal end attached to expandable frame, a distal end opposite the proximal end, a major axis, and an outer face, Upon movement of the connector relative to at least one base component, the expandable frame moves from a first position to a second position, thereby increasing the average distance between two base components. The combined outer faces of the retractor blade are cylindrical when the expandable frame is in a first position.

In another embodiment, this invention includes a surgical retractor, comprising a housing component having a central axis and including a cylindrical portion, wherein the cylindrical portion defines a conduit having an inner diameter normal to the central axis; and a blade portion that is contiguous with one end of the cylindrical portion, wherein the blade portion includes at least two blades, wherein a distal portion of each blade is moveable relative to the central axis; and a cylindrical expander component having an outer diameter, wherein the outer diameter is smaller than the inner diameter of the cylindrical portion and the expander component is movably attached to the housing component. In a first position, distal ends of the blade portion are proximate, and upon movement of the distal portion of the blades relative to the central axis, the blades move from a first position to a second position, thereby forming a continuous conduit down the length of the central axis. Optionally, at least one blade includes a tow-out protrusion.

Figure 29:
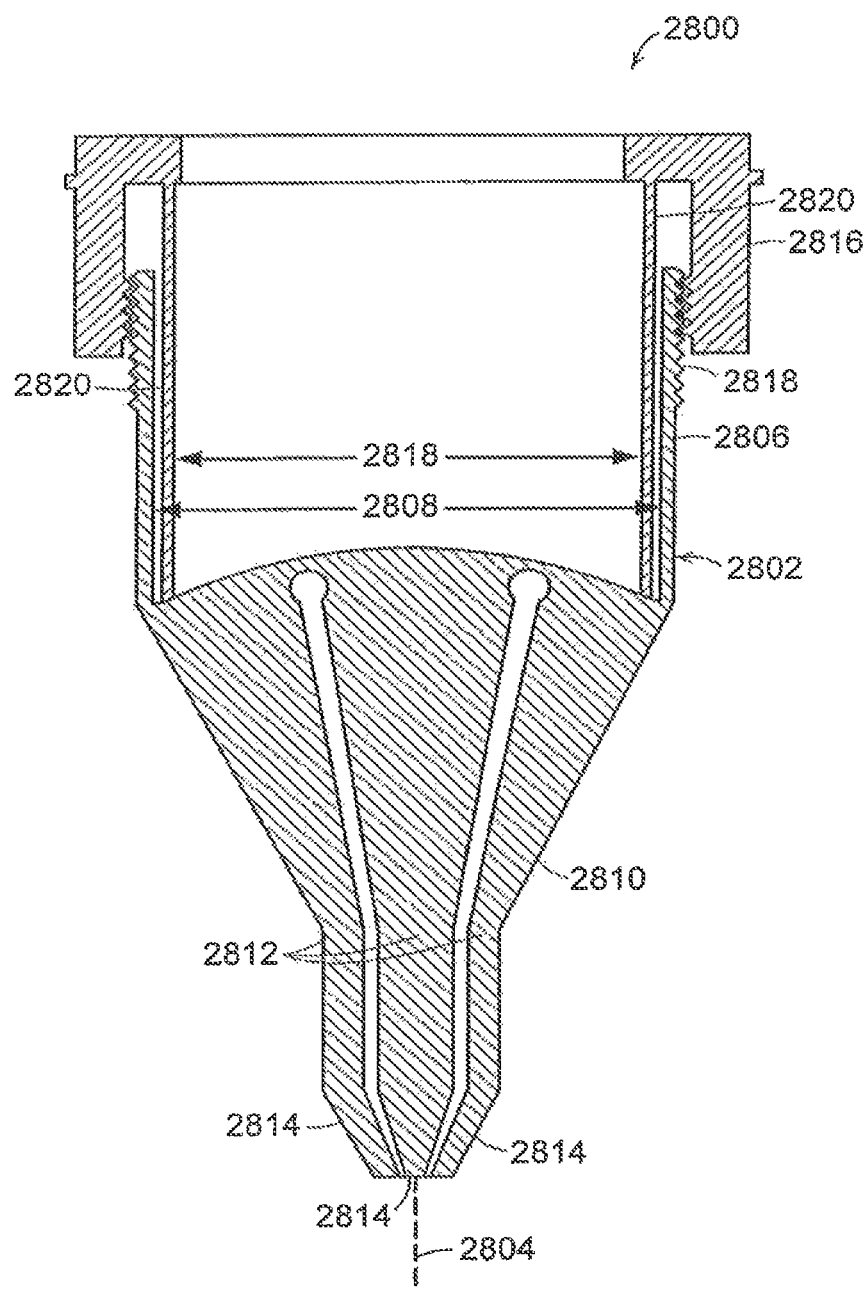
FIGS. 29 and 30 illustrates one embodiment of a retractor of the invention.
Figure 30:
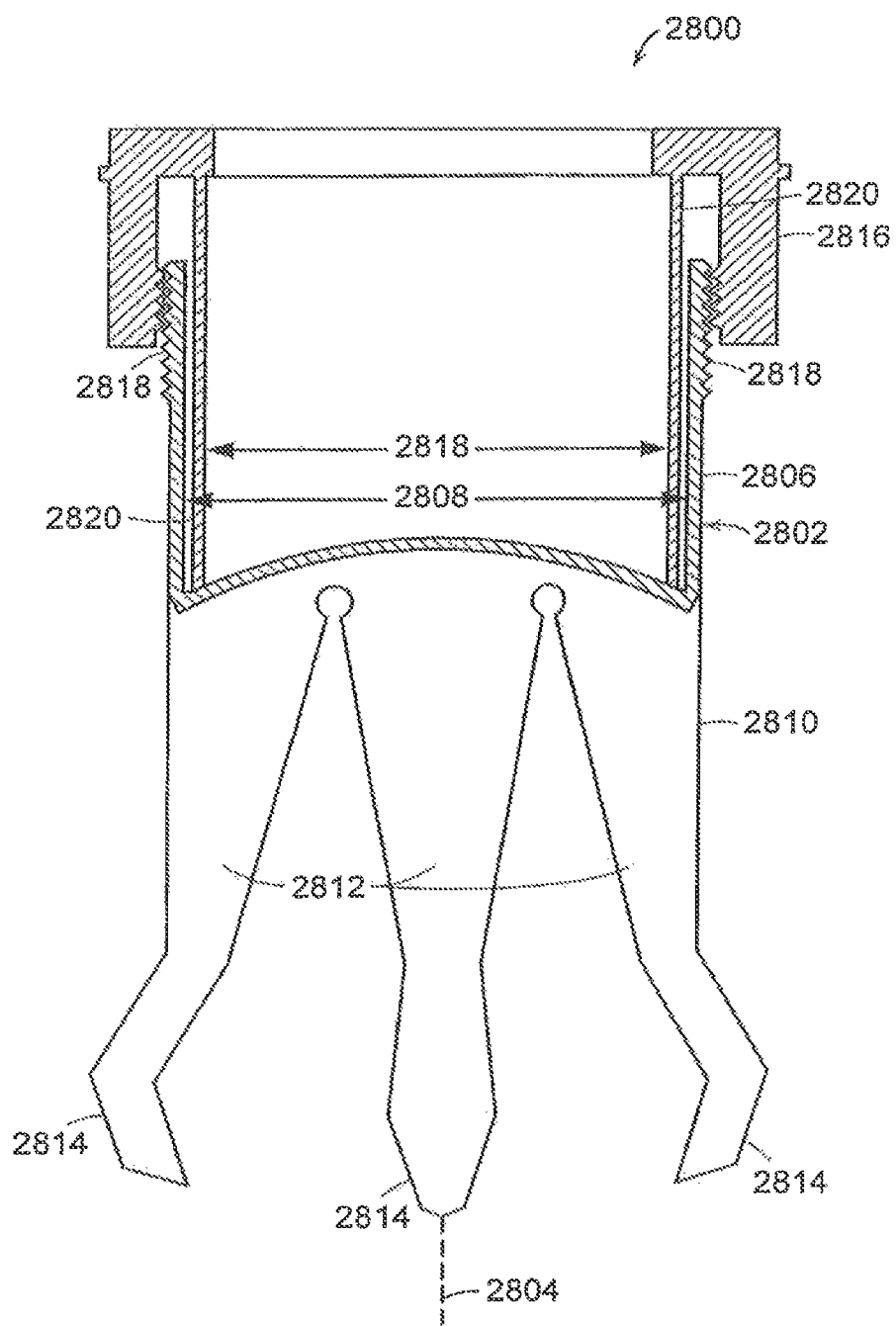

FIGS. 29 and 30 illustrates one embodiment of a retractor of the invention. FIG. 29 illustrates retractor 2800 in a first position. Retractor 2800 comprises housing component 2802 that has central axis 2804. Housing component 2802 includes cylindrical portion 2806 which defines a conduit having inner diameter 2808 normal to central axis 2804. Blade portion 2810 is contiguous with one end of cylindrical portion 2806 and includes blades 2812. Blades 2812 have distal portions 2814 that is moveable relative to central axis 2804. Cylindrical expander component 2816 is movably attached to housing component 2802 by screw threads 2818. Cylindrical expander component 2816 includes a blade expansion mechanism that comprises an extension 2820 that extends down the inner walls of cylindrical portion 2806.

FIG. 29 illustrates retractor 2800 in a first position, where distal ends 2814 are proximate to one another. FIG. 30 illustrates retractor 2800 after expander component 2816 has been rotated relative to housing component 2802. Such rotation causes expander component 2816 to press along screw threads 2818, pressing extension 2820 into the inner wall of blade portion 2810 and causing blades 2812 to move radially from central axis 2804, thereby expanding a surgical site.

In the first position illustrated in FIG. 29, distal ends 2814 were proximate to each other and blade portion 2810 formed a cone. In the second position illustrated in FIG. 30, distal ends 2814 are splayed or distant from each other and central axis 2804. In the first position, the conical shape of blade portion 2810 allow retractor 2800 to be easily inserted into an organism (e.g., through an incision) with a minimum of trauma to surrounding tissue. Once in a desired location, retractor 2800 can be expanded to the second position, thereby forming a surgical site and providing a practitioner access to that site.

Figure 31:
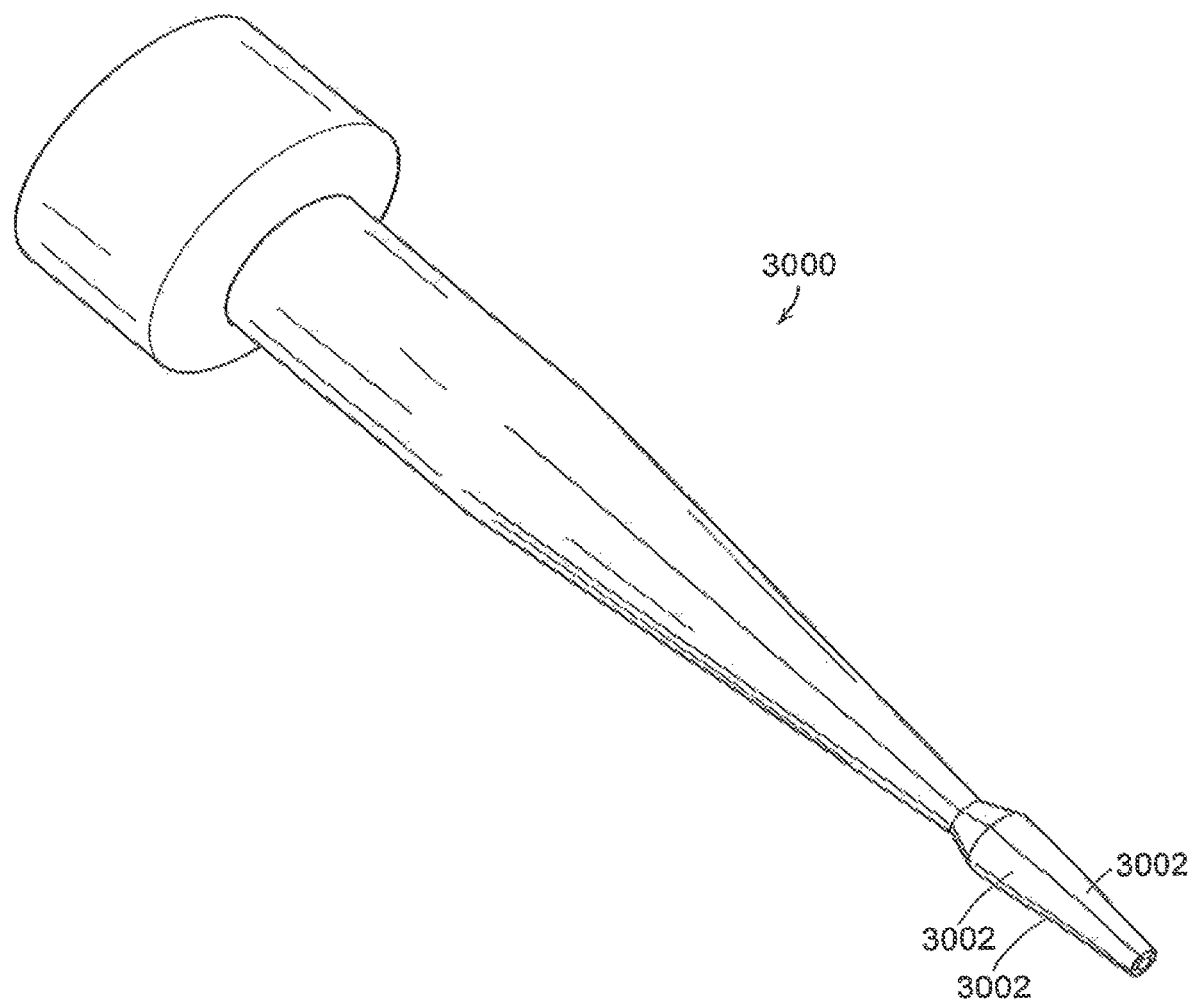
FIG. 31 illustrates one embodiment of a retractor of the invention with distal ends at a first position and FIG. 32 illustrates the retractor with distal ends at a second position.
Figure 32:
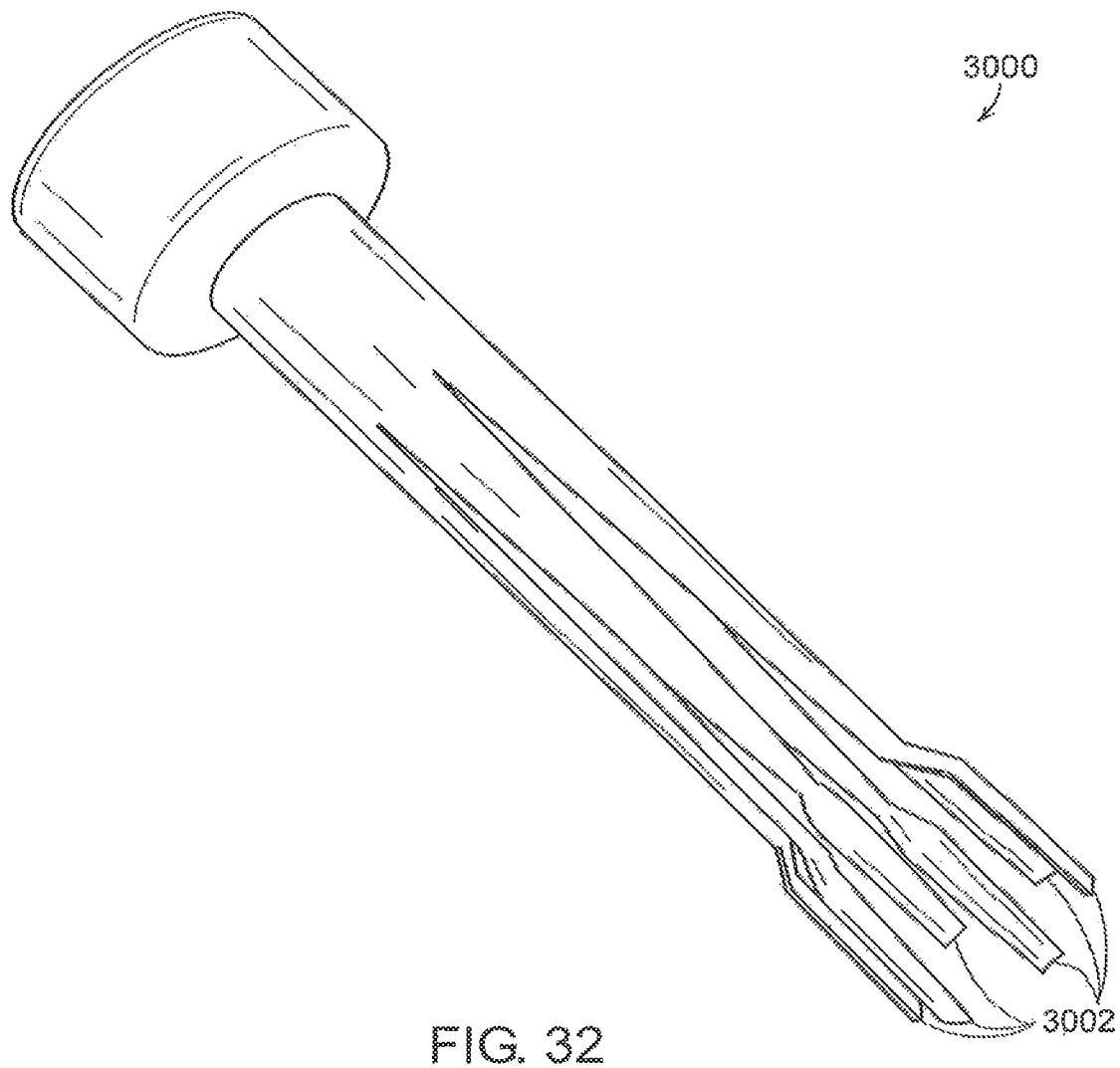
Figure 33:
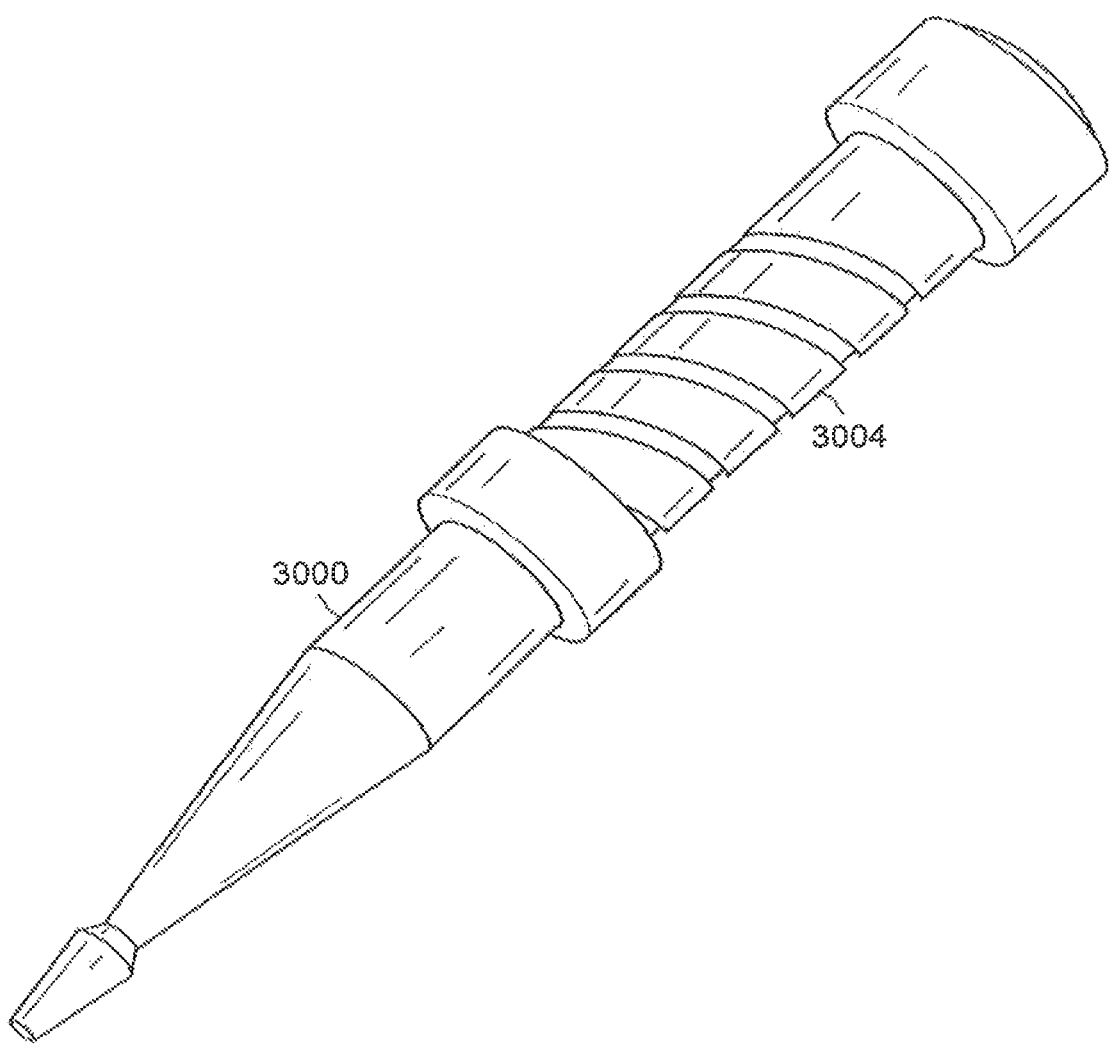
FIG. 33 illustrates the retractor shown in FIGS. 31 and 32 with one embodiment of an attached expander component.

FIG. 31 illustrates retractor 3000, with distal ends 3002 in a first position. FIG. 32 illustrates retractor 3000 with distal ends 3002 in a second position. FIG. 33 illustrates retractor 3000 with attached expander component 3004.

In another embodiment, this invention includes a method of performing surgery on an organism, comprising the steps of creating an incision in the organism, retracting the tissue surrounding the incision with a retractor to form a surgical site, and performing a surgical procedure at the surgical site.

In some embodiments, this invention includes an illuminated Surgical cannula. In one embodiment, an illuminated surgical cannula, comprises a surgical cannula that has an outer diameter, an inner diameter, a distal end, and a proximal end, wherein the inner diameter, the distal end, and the proximal end define an interior area; and an interface ring attached to the proximal end, wherein the interface ring includes a light source interface mechanism in photonic communication with an array of fiber optic wire, wherein the array is arranged to direct light towards the distal end of the cannula. The interior area is illuminated by the light source. In some embodiments, the interface ring includes a light source (e.g., a led light or some other light source).

In some embodiments, the cannula includes at least one fiber optic wire that is in photonic communication with the array of the interface ring at the proximal end and extends down at least a portion of the length of the cannula towards the distal end. In a further embodiment, at least a portion of the fiber optic wire is embedded in the cannula between the outer and inner diameters.

Optionally, at least a portion of the cannula is translucent. In some embodiments, at least a portion of the cannula is transparent. In further embodiments, the cannula tube incorporates features (e.g., bevels or surface roughness) that captures and redirects light to a desired location to aid in illumination.

FIG. 34 illustrates one embodiment of an interface ring. Interface ring 3300 includes a light source interface mechanism 3302. Light source interface mechanism 3302 directs light from an outside light source (e.g. a light source commonly used in an operating procedure) to an array 3304 of fiber optic wire 3306. Interface ring 3300 defines access portal 3308 that provides a practitioner access to an attached cannula. Array 3304 is disposed around interface ring 3300 and projects light down the length of a cannula. Optionally, array 3304 directs light to a cannula that comprises at least a portion of a light-conducting material. In some embodiments, an interface ring forms a complete circle and fits on top of a cannula or retractor of the invention. In other embodiments, an interface ring forms a portion of a circle (e.g., a half circle or a quarter circle) and fits on top of a cannula or retractor of the invention.

FIG. 35 illustrates a portion of a cannula that includes a light-conducting material. Cannula 3400 includes a plurality of fiber optic wires 3402. Fiber optic wire 3402 are embedded within the material forming the wall of cannula 3400. FIG. 36 illustrates interface ring 3300 assembled to a portion of a cannula 3400.

The cannula illustrated in the figures is just one embodiment of a cannula of the invention. The illuminated cannula, or portions thereof (e.g., an interface ring), can be used with any retractor of the invention.

Figure 37A:
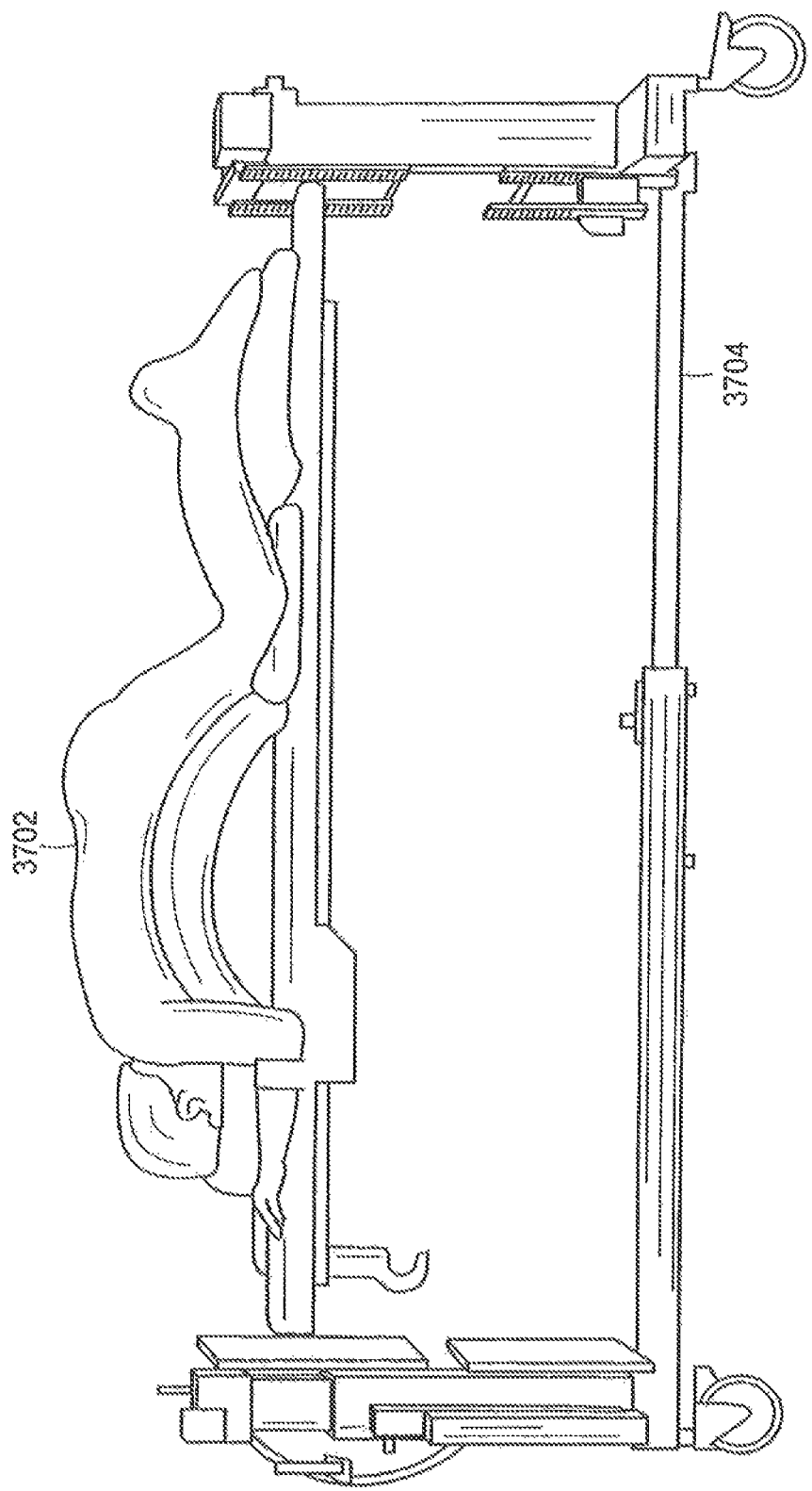
FIGS. 37A-37U illustrate embodiments of the invention that include a method of using a retractor (e.g., a retractor of the invention) during a surgical procedure on the spine of a human and related instruments and tools.

In some embodiments, this invention features methods of performing surgical procedures on the spine of a human using retractors of the present invention. FIGS. 37A-37U illustrate embodiments of the invention that include a method of using a retractor (e.g., a retractor of the invention) during a surgical procedure on the spine of a human and related instruments and tools of the invention.

FIG. 37A illustrates patient 3702 in a prone position on table 3704 (e.g., a Jackson Table or other table used for image procedures) in such a way so as to provide an unrestricted view for imaging. In some embodiments, a frame (e.g., a Wilson frame) is used to assist the practitioner in placing patient 3702 in a desired position. Additionally, sockets (e.g., a Clark Socket) can be positioned on the table rail lateral to the patient's mid or upper thigh, thereby facilitating subsequent placement of a rigid arm assembly.

Proper targeting of the surgical site eases surgery and minimizes the need to enlarge an incision. In some embodiments, the multifidus and longisimus muscles that run parallel to the spine are dilated. Optionally, fluoroscopy is used to locate a desired level and close attention is made to keep the targeted surgical site at the center of the fluoroscopic view. For example, for a transforminal lumbar interbody fusion, the center of the target is generally the medial border of the facet joint of the desired disc level. An incision template may be used (with or without fluoroscopic guidance) to locate the incision's center over the disc space of the proper level to be operated on. Pressing the retractor into the skin of patient 3702 will make an imprint and provide a good indication of the size of the needed incision.

Once the surgical site has been targeted, a longitudinal r incision slightly larger than the retractor of the invention (e.g., a retractor of the invention that is in a semi- or fully-contracted or condensed form) is made. In some embodiments, only the skin is incised since dilators can be used to pierce and dilate the fascia.

Figure 37B:
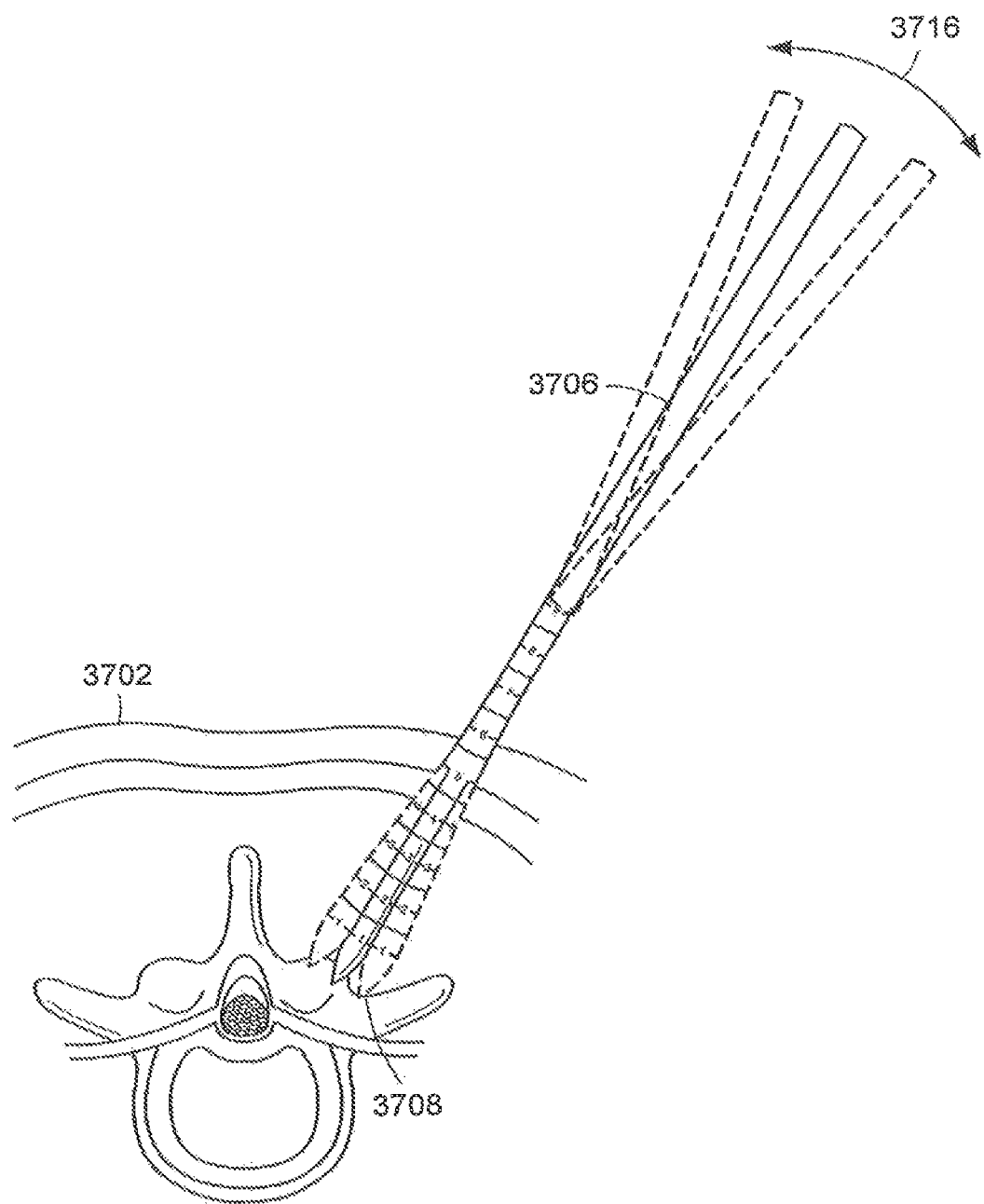

Once the incision is made, a dilator is inserted into the incision, bluntly piercing the fascia to dilate the paravertebral muscle tissue down to the laminar level, as illustrated in FIG. 37B. Optionally, the fascia is incised prior to the insertion of the first dilator. The dilator's position may be confirmed fluoroscopically. With careful tactile sensation, the paravertebral muscles are swept free from the lamina, base of the spinous process, and over the facet joint with a gentle wanding motion along line 3716, thereby facilitating visualization and ensuring the subsequent dilators and retractor is fully seated against the facet.

Figure 37C:
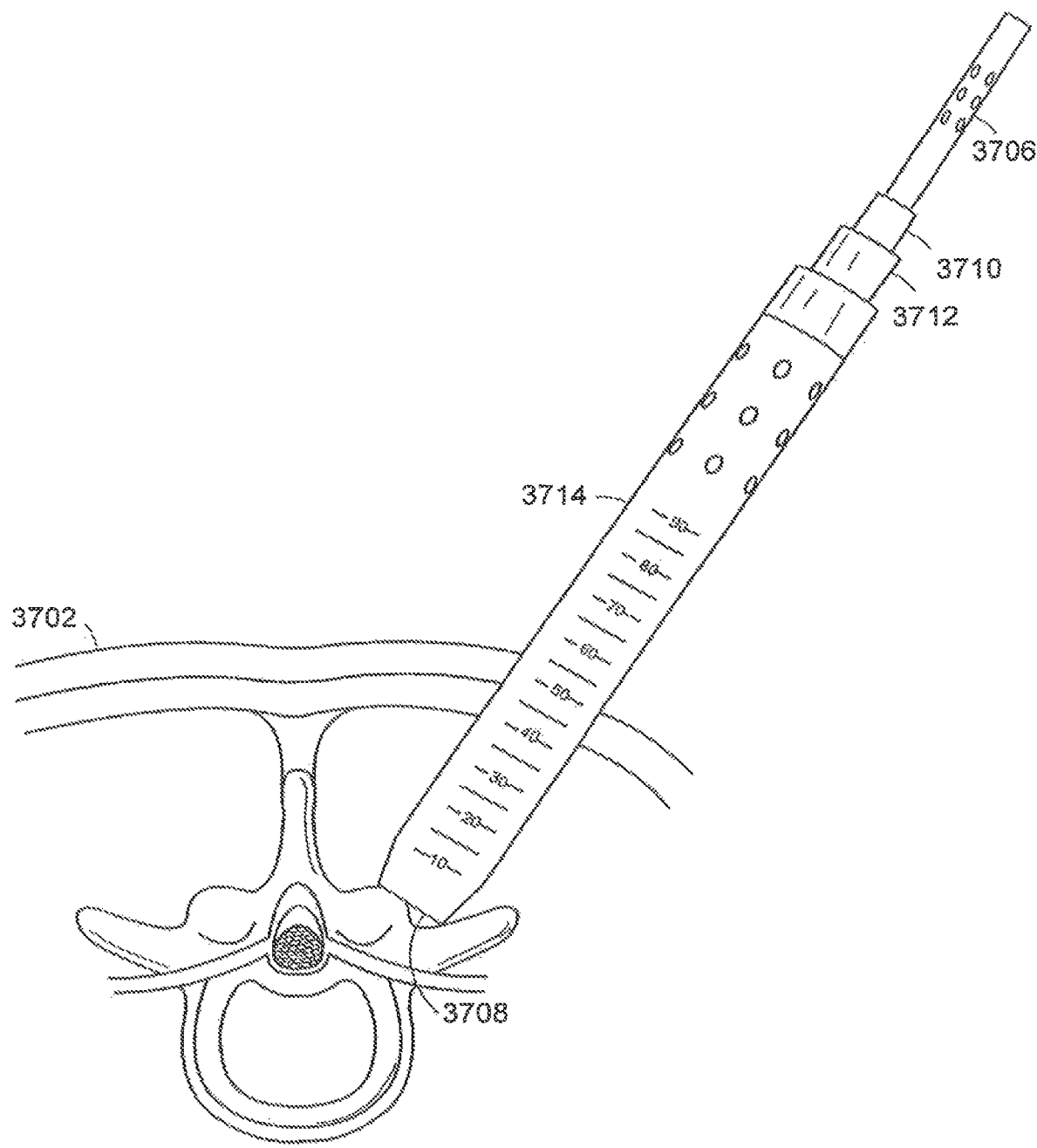

As shown in FIG. 37C, sequential dilation is performed by passing the next largest dilator 3710 over dilator 3706 and directed down to surgical site 3708. Similarly, dilator 3712 is then passed over dilator 3710 and then dilator 3714 is passed over dilator 3712. In some embodiments, an introducer is utilized to insert the larger dilators.

In some embodiments, depth measurements are taken from the where the skin contacts the dilator. The depth is most effectively measures with dilators 3710 or 3712, as these dilators will be flush to the bone and produce the most accurate measurement.

Once the incision has been dilated, a retractor of the invention is directed to surgical site 3708. In some embodiments, the retractor is directed to surgical site 3708 with an open Wiltse approach where the natural muscle plane is located through mobilized midline incision or a lateral incision.

Figure 37D:
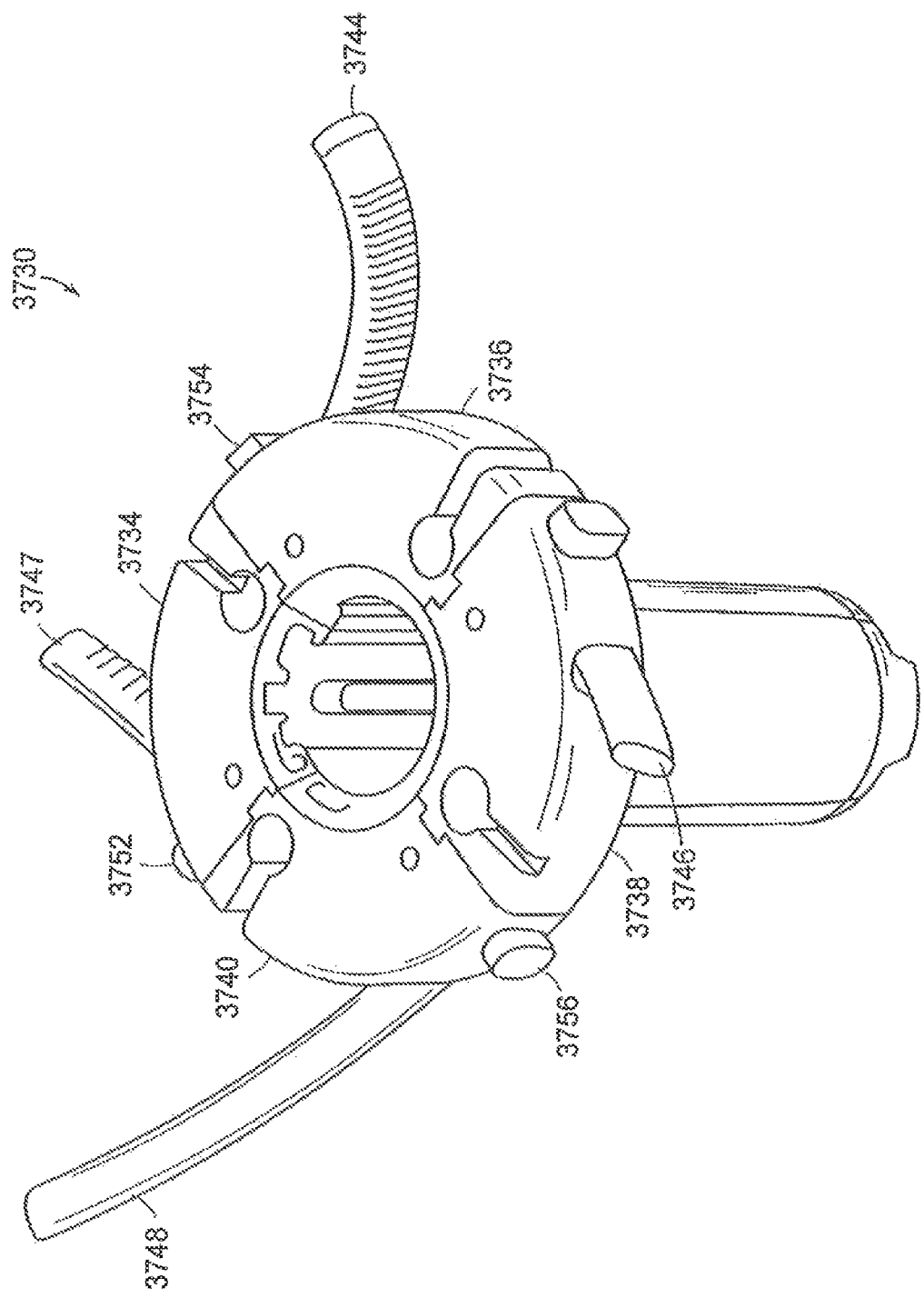

The retractor is assembled before it is directed to surgical site 3708. FIG. 37D illustrates assembled retractor 3730. Retractor 3732 includes base components 3734, 3736, 3738, and 3740.

FIG. 37E illustrates one step of the assembly process. Base component 3740 includes arm 3742. Base component 3734 includes arm 3744 and defines arm hole 3750. Release button 3752 is depressed to disable the locking mechanism of component 3734, and arm 3742 is directed through hole 3750, thereby connecting or assembling component 3740 to component 3734. Similarly, component 3736 is assembled to component 3738.

Figure 37F:
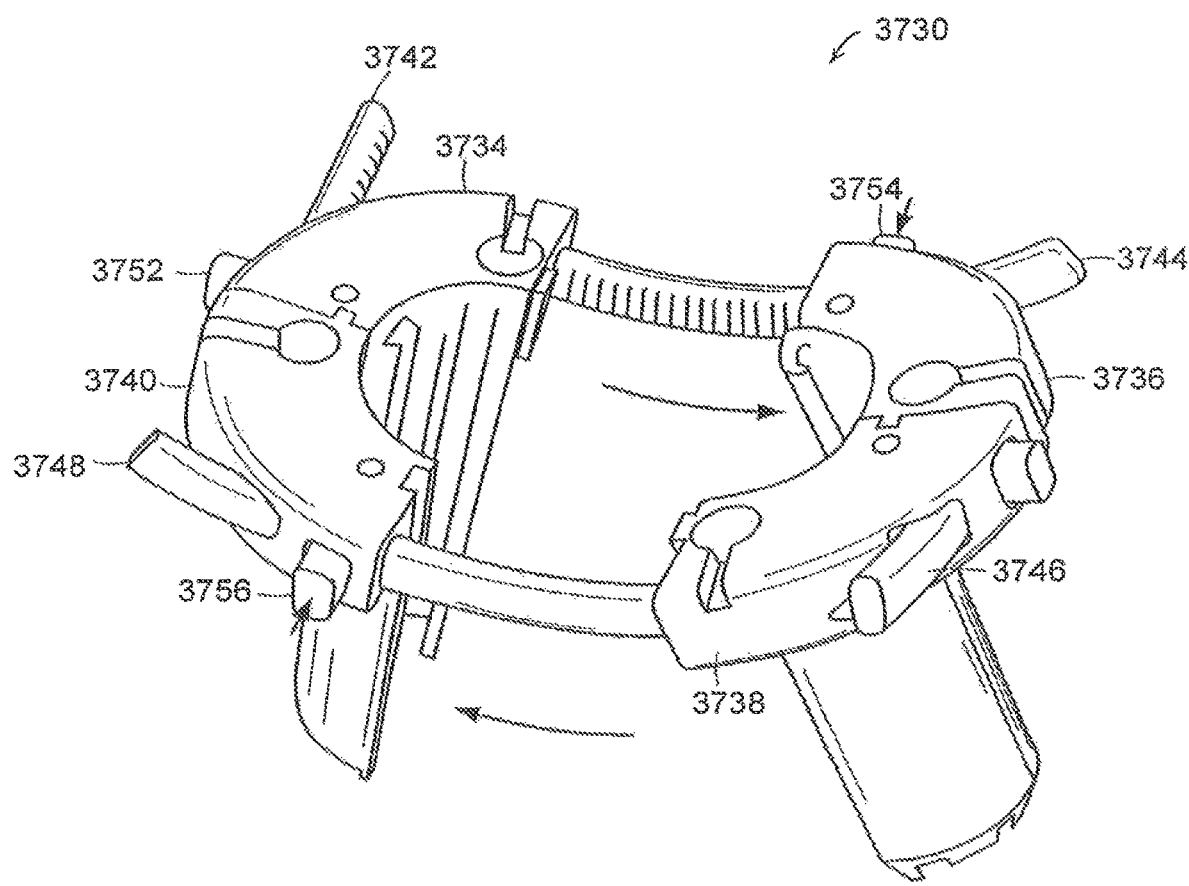
Figure 37G:
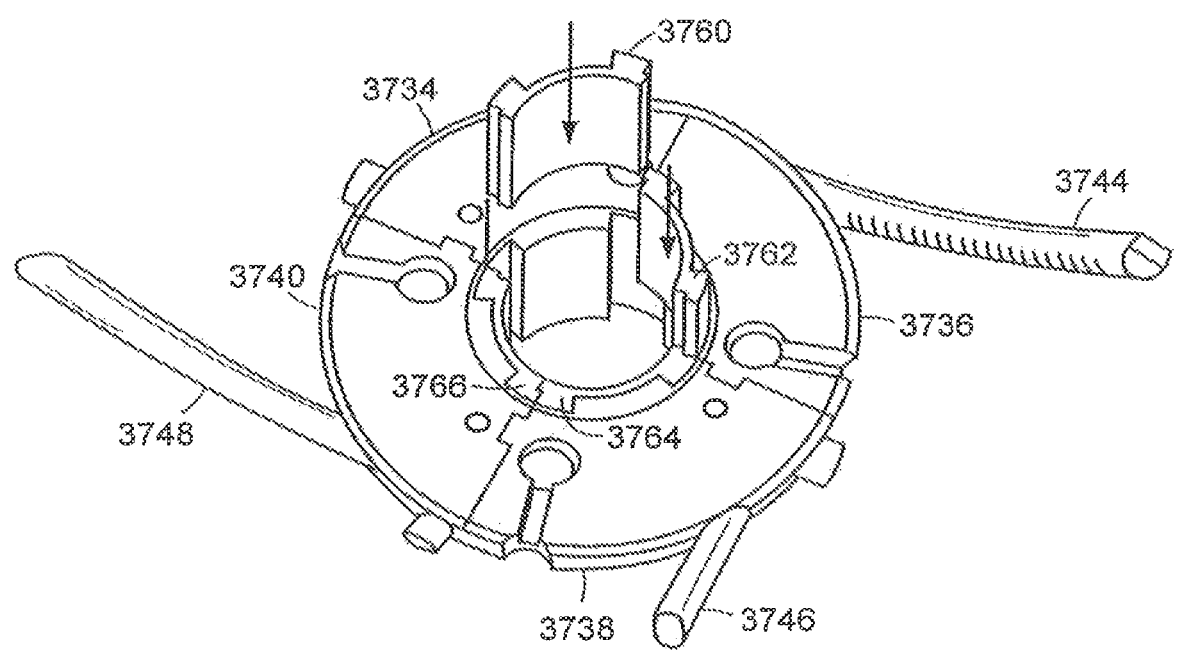
Figure 37H:
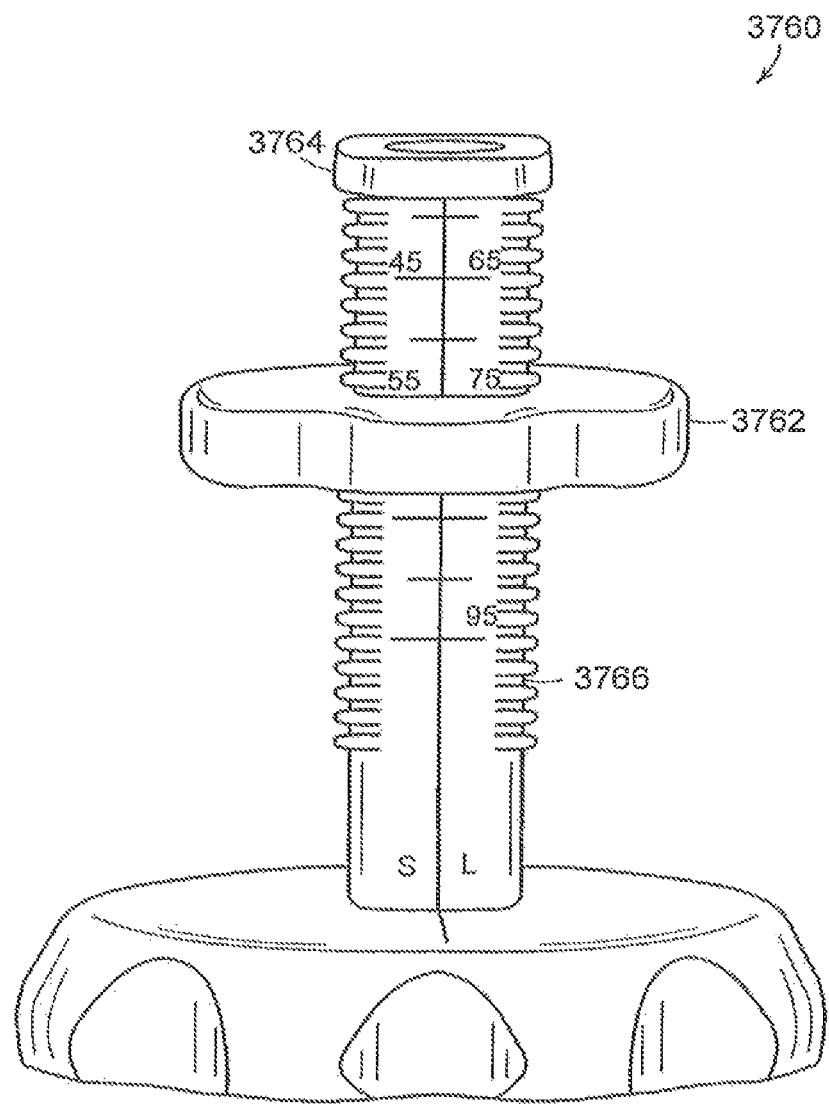

Once component 3740 is assembled to component 3734 and component 3438 is assembled to component 3736, release buttons 3754 and 3756 are depressed and arm 3748 is directed through component 3740 and arm 3744 is directed through component 3740, thereby assembling all four base components, as shown in FIG. 37F. Retractor blade extensions 3760, 3762, 3764, and 3766 are then slide into base components 3734, 3736, 3738, and 3740, respectively, as illustrated in FIG. 37G. In this manner, a practitioner of the invention assembles retractor 3730, as shown in FIG. 37D.

Optionally, the telescoping blade extensions of retractor 3730 are extended to a desired length before inserting the retractor into patient 3702. FIG. 37E illustrates blade depth tower 3760 can be used to assist a practitioner of the invention in extending the blade extensions. Tower 3760 includes ring 3762 which is assembled to shaft 3766. Shaft 3766 includes two series of markings (each corresponding to a different sized retractor) on shaft 3766. Ring 3762 is rotated, causing ring 3762 to translated up or down the length of shaft 3766.

Figure 37I:
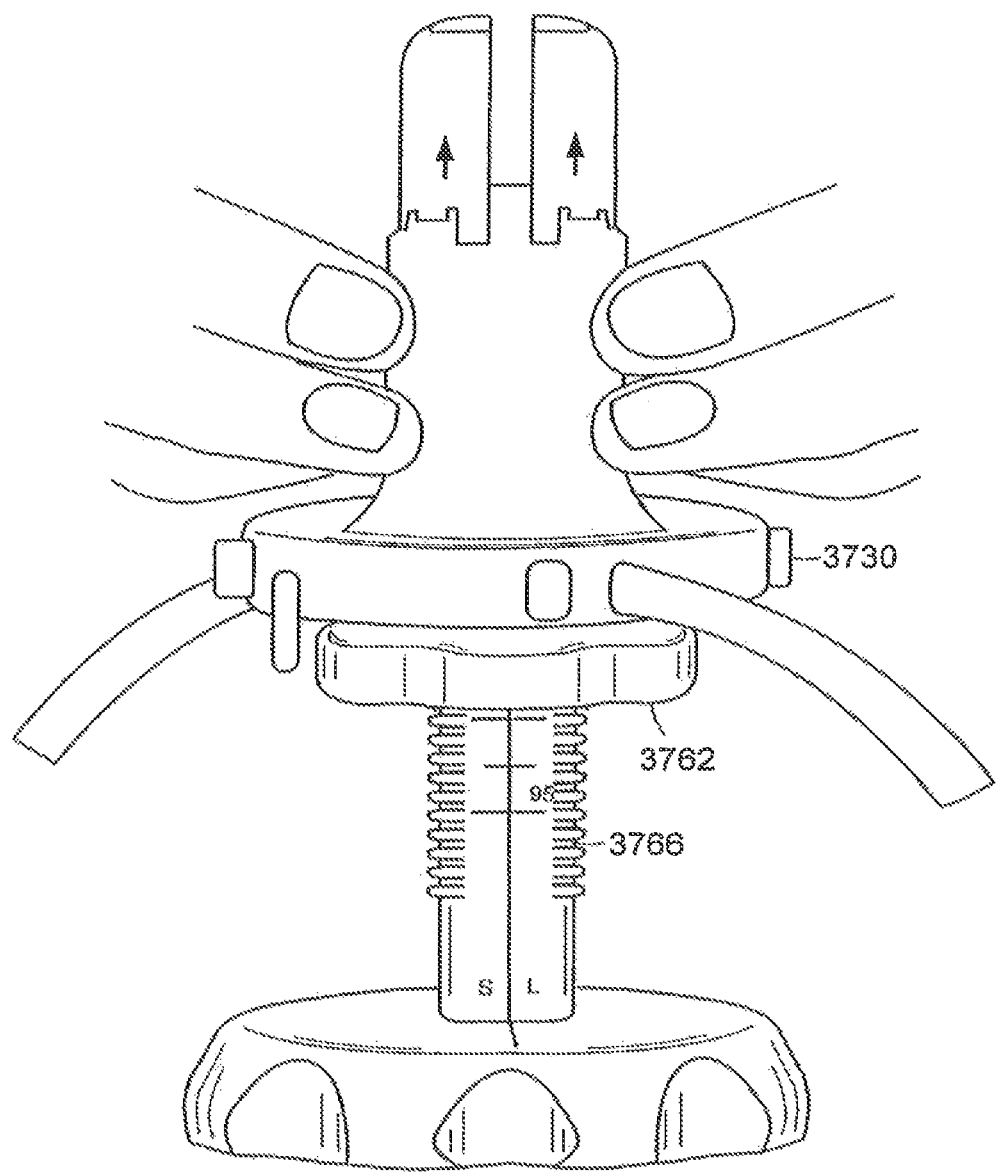

To use tower 3760 to extend the blades, a practitioner of the invention rotates ring 3762 to a position along shaft 3766. The markings on shaft 3766 are used to determine the desired position. As shown in FIG. 37I, retractor 3730 is directed over top end 3764 of shaft 3766 and down to ring 3730. Top end 3764 engages the blade extensions of retractor 3730 and extends them as retractor 3730 is directed down to ring 3762.

Figure 37J:
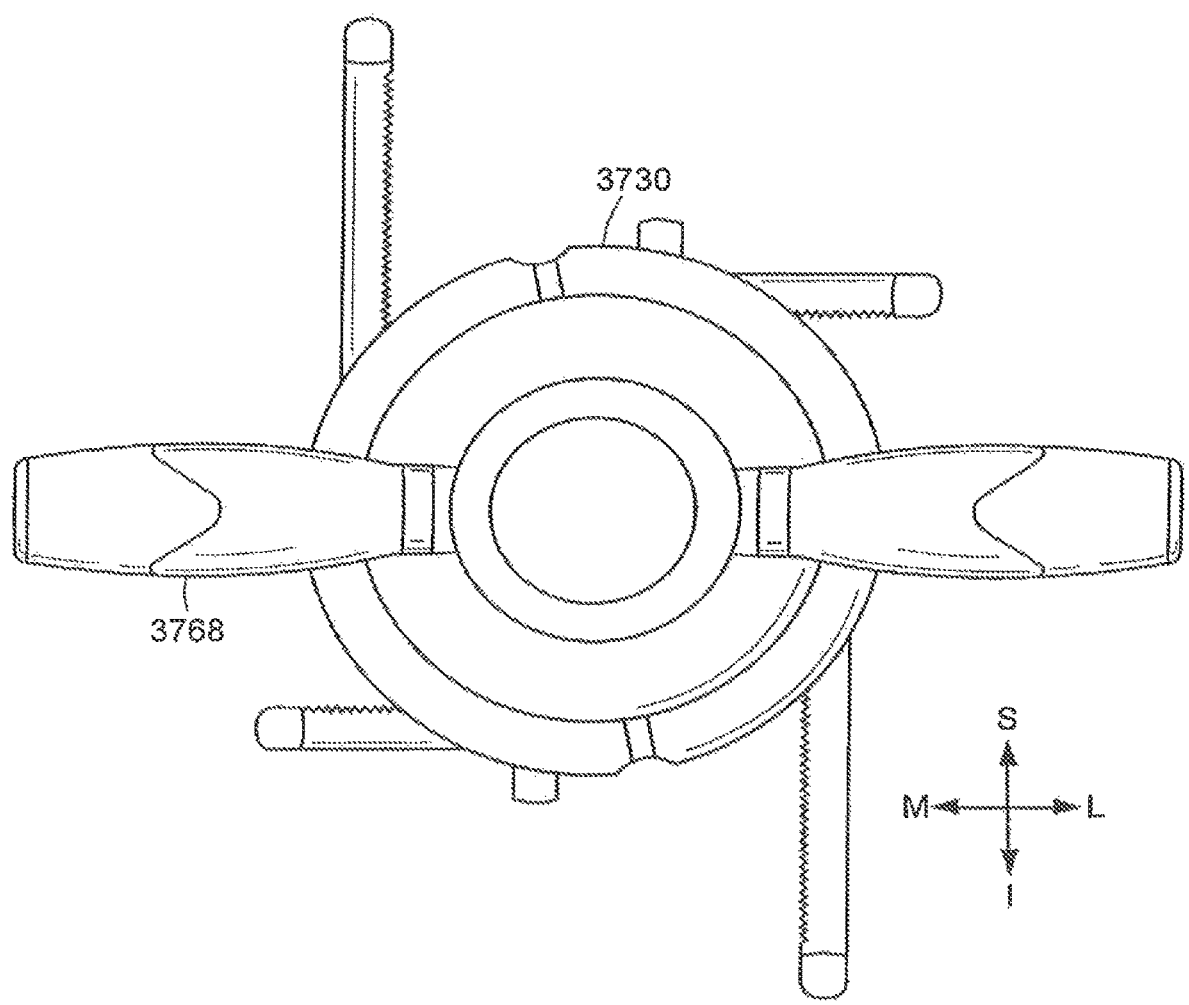
Figure 37K:
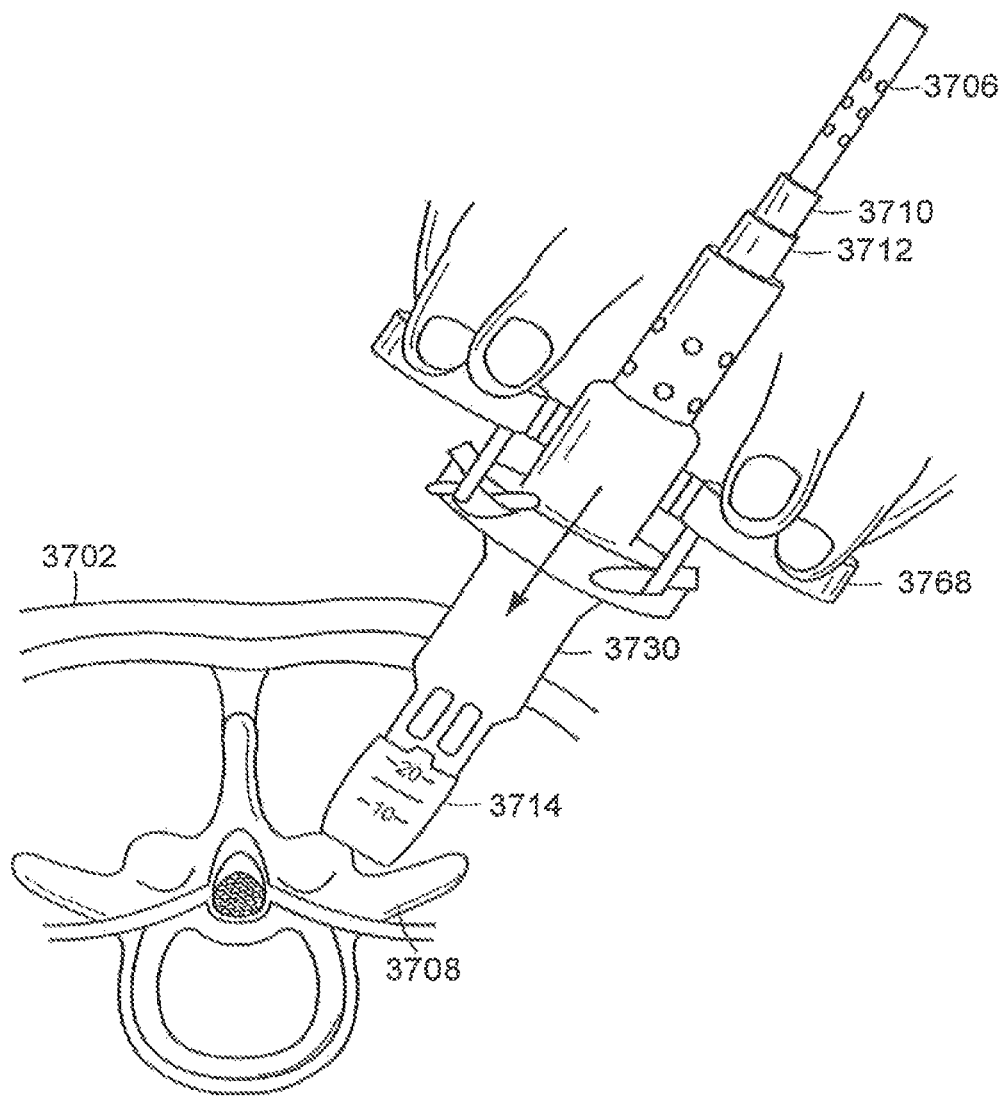

In some embodiments of the invention, the retractor is assembled to an inserter before insertion into a patient. FIG. 37J illustrates retractor 3730 assembled to handle inserter 3768. Handle inserter 3768 is assembled to retractor 3730 by directing the attachment pins of inserter 3768 into the attachment holes on the frame of retractor 3730. Once assembled to inserter 3768, a practitioner of the invention uses inserter 3768 to direct retractor 3730 over the dilators and down to surgical site 3708. During insertion, care should be taken to ensure the dilators remain fully seated on the facet so as to avoid creep of soft tissue underneath the dilators.

Figure 37L:
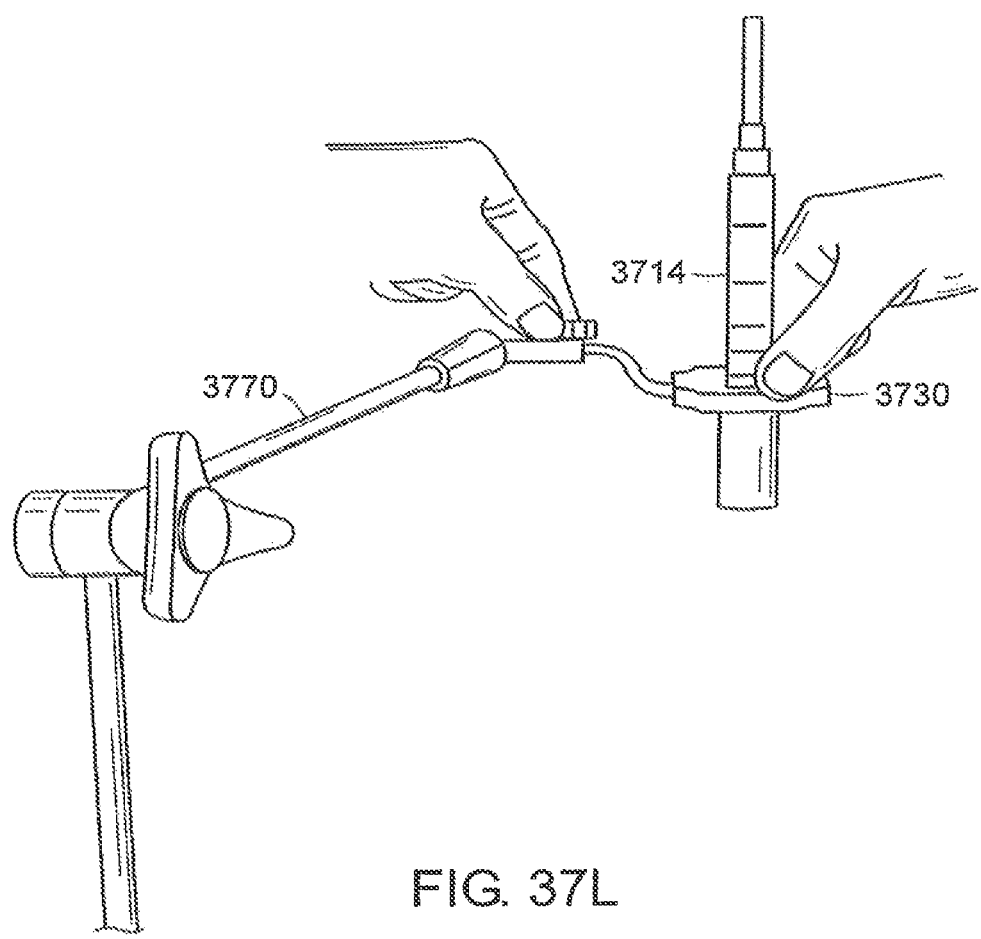

Once inserted into patient 3702, one or more rigid arms 3770 can be attached or scoured to retractor 3730, as illustrated in FIG. 37L. Rigid arm 3770 is secured to the surgical table and is attached to retractor 3730 at one of the attachment holes on the expandable frame. Rigid arm 3770 can be adjusted during the surgical procedure, thereby allowing a practitioner of the invention to direct retractor 3730 to a desired position.

Figure 37M:
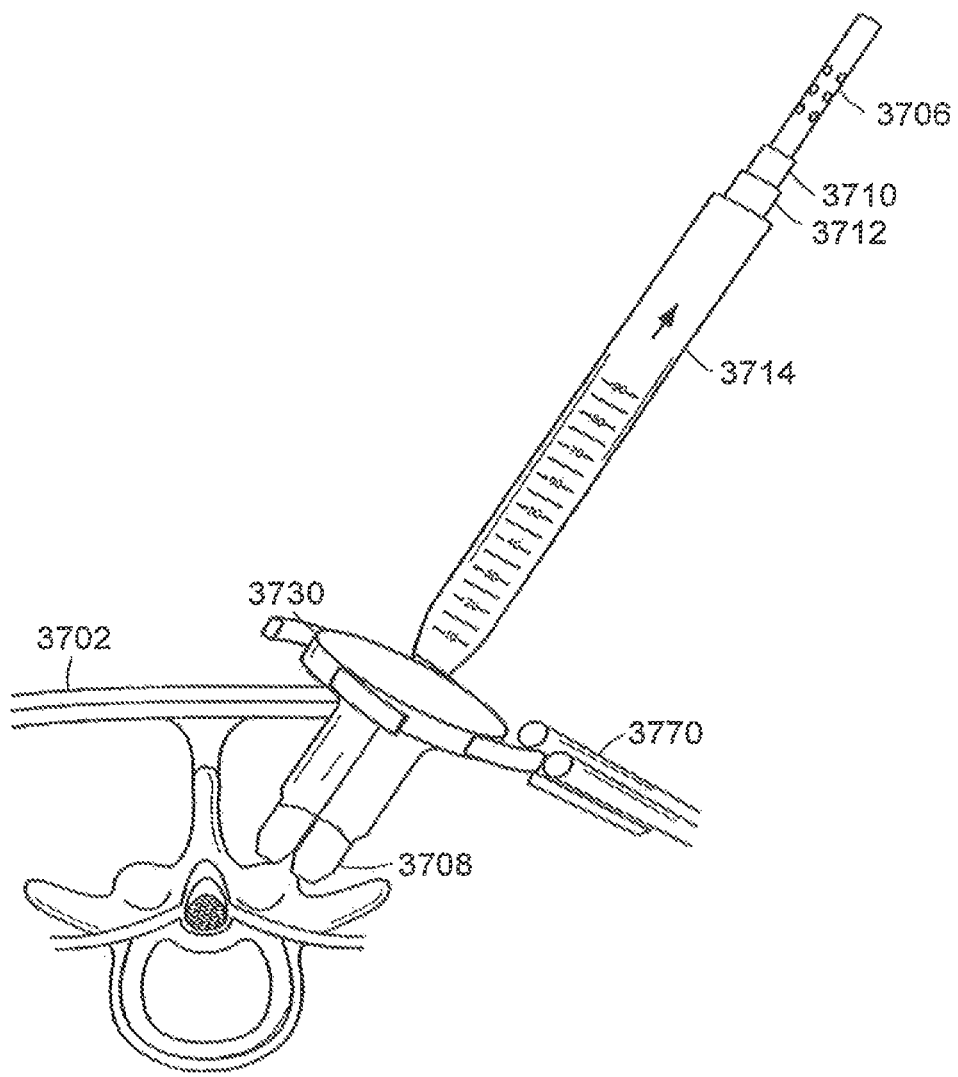

Dilators 3706, 3710, 3712, and 3714 are removed from patient 3702, as illustrated in FIG. 37M, During removal of the dilators, care should be taken to ensure retractor 3730 remains fully seated against the lamina and facet to prevent creep of soft tissue.

In some embodiments of the invention, electrocautery is used to remove any remaining muscle attached to the bone inside of the inserted retractor, thereby preventing or reducing bleeding from the tissue. The bone can be gently palpated with an inactive, extended length bowie tip to ensure that it is against bone. A pituitary rongeur can be used to pluck the fragments out of the exposure. Irrigation is optionally sued to ensure adequate visualization during these maneuvers.

Figure 37N:
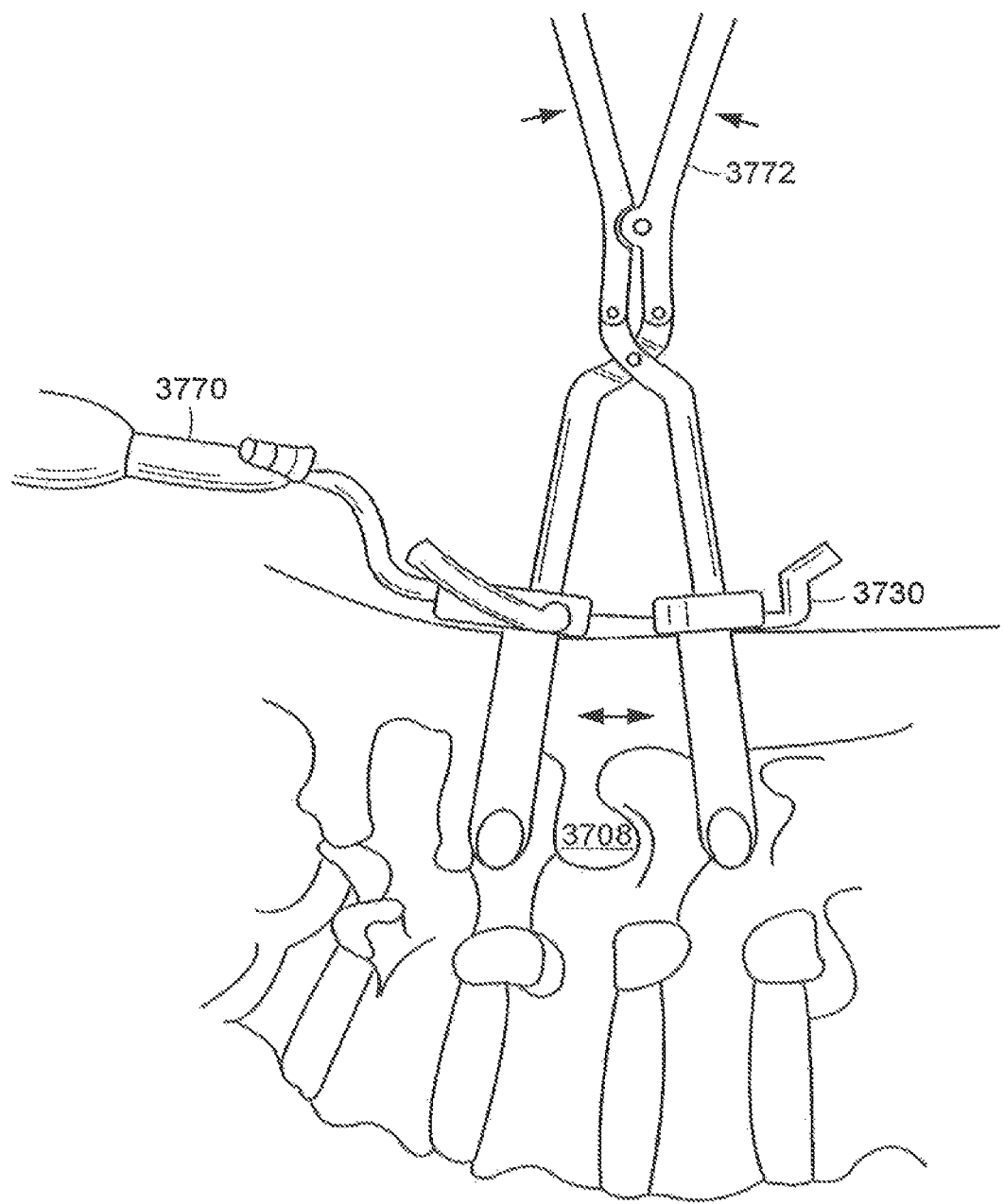
Figure 370:
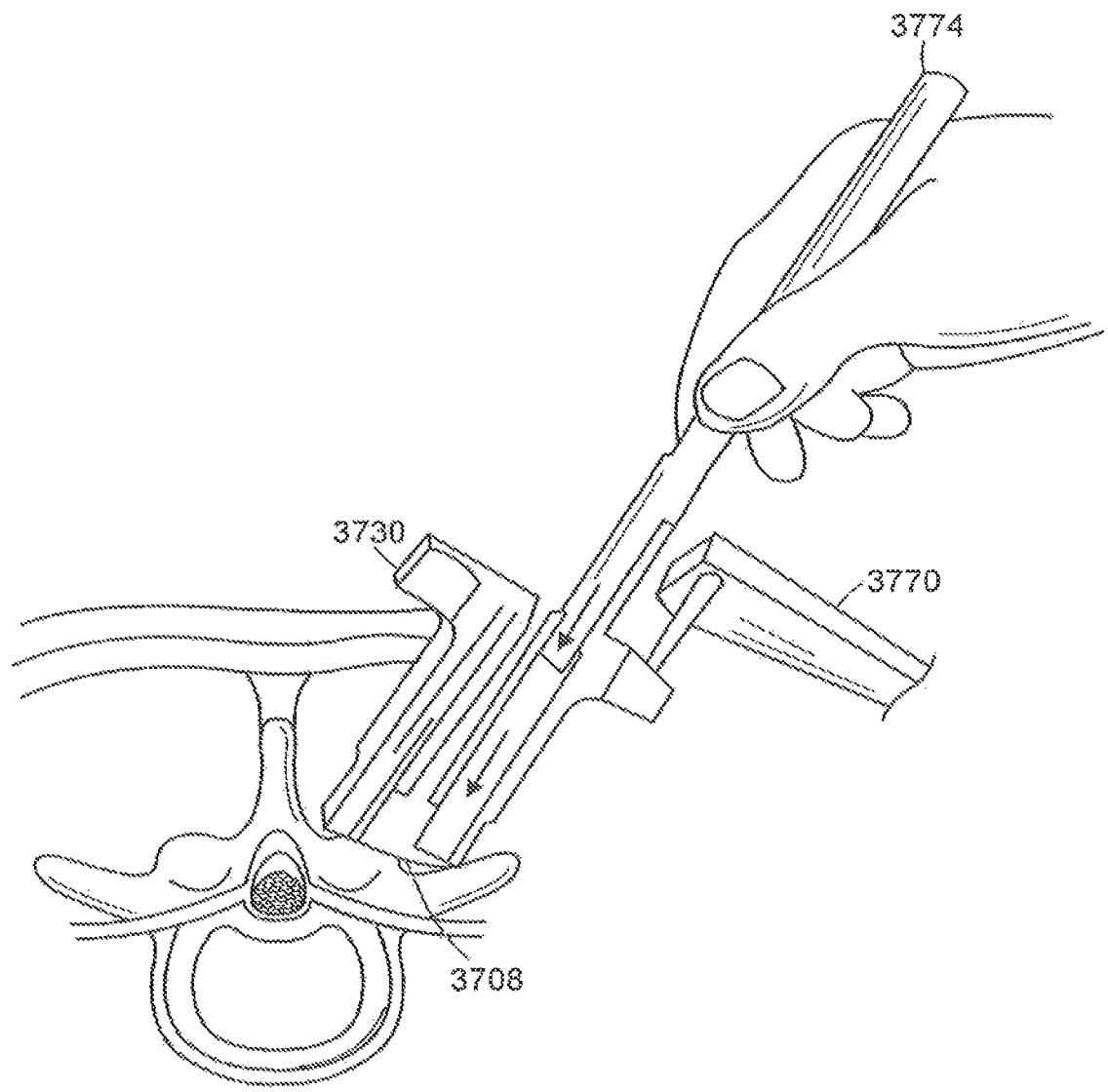

Once retractor 3732 has been inserted and the dilators removed, refractor 3732 can be expanded using distractor instrument 3772, as illustrated in FIG. 37N. Retractor 3732 can be expanded in the cephlad-caudal and/or the medial-lateral directions by inserting instrument 3772 into the top of retractor 3732 and squeezing the handle of instrument 3772 to the desired extent. The teeth of the locking mechanism of the expandable frame allow for micro adjustment and will hold retractor 3732 at the expanded position. In some embodiments of the invention, the distractor instrument is used parallel to the curved racks to avoid undue stress on the retractor.

After retractor 3730 is expanded and the facet joint is visible, blade pusher 3774 may be used to deploy the telescoping blade extensions thither to, for example, prevent soft tissue creep in the working space. FIG. 37O illustrates a practitioner of the invention deploying the extensions with pusher 3774.

Figure 37P:
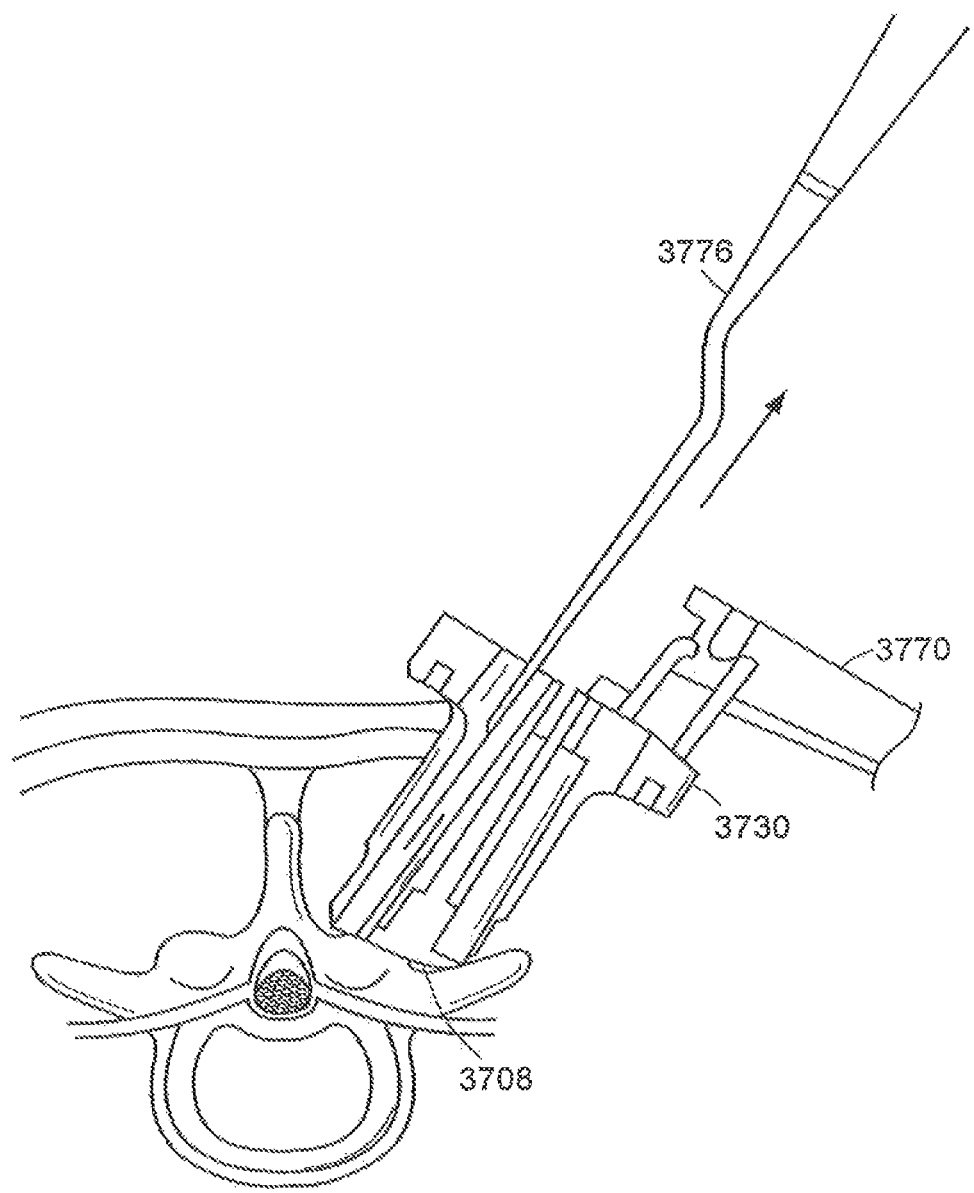
Figure 37Q:
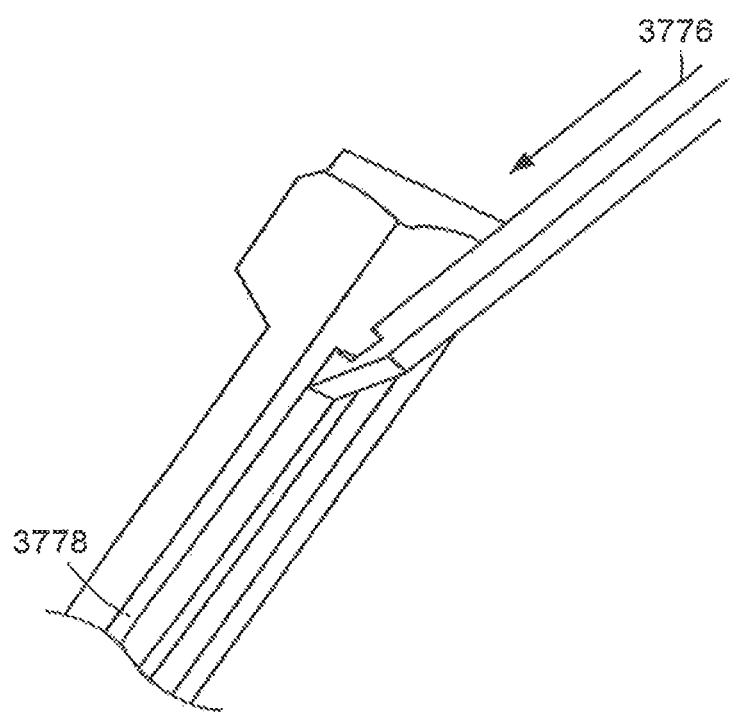
Figure 37R:
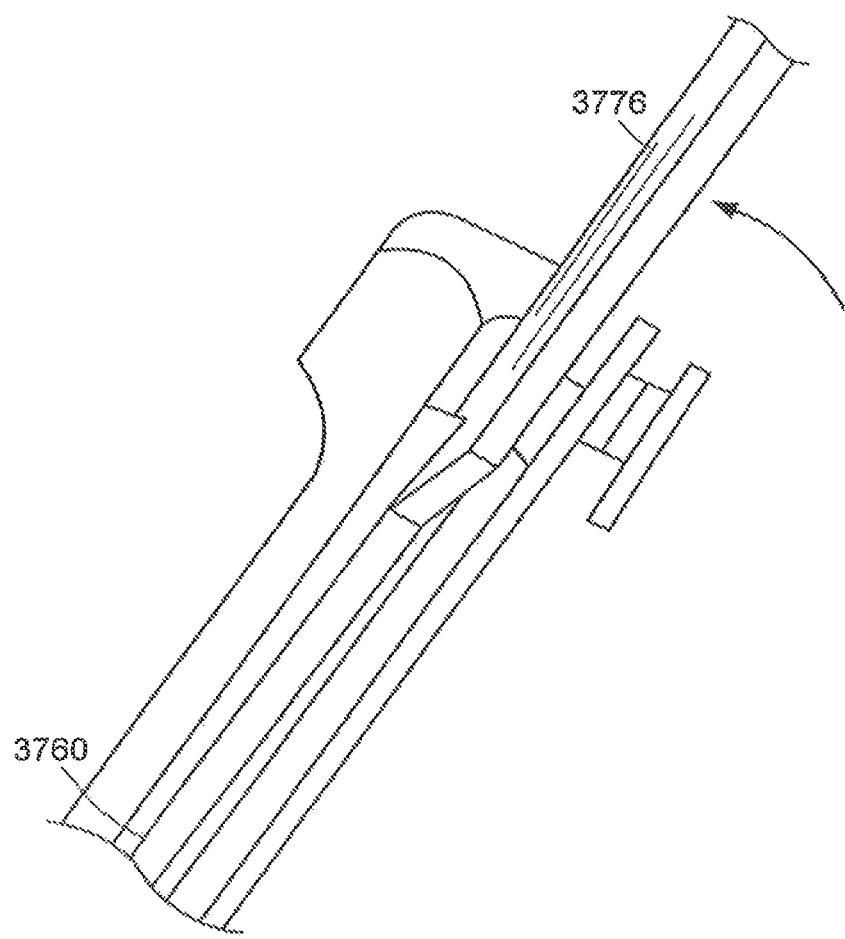

Optionally, the extensions can be removed and/or adjusted upward at any point of the surgical procedure. FIGS. 37P-37R illustrate a practitioner of the invention removing or adjusting a blade extension upward with blade remover 3776. FIGS. 37Q and 37R illustrate a close-up view of remover 3776 engaging blade extension 3778. Blade remover 3776 is inserted into the tooth of telescoping blade extension 3778 and the handle of remover 3776 is moved outward to relieve the locking mechanism of extension 3778, as illustrated in FIG. 37R. This allows extension 3778 to be removed and/or adjusted upward, as illustrated in FIG. 37P.

Figure 37S:
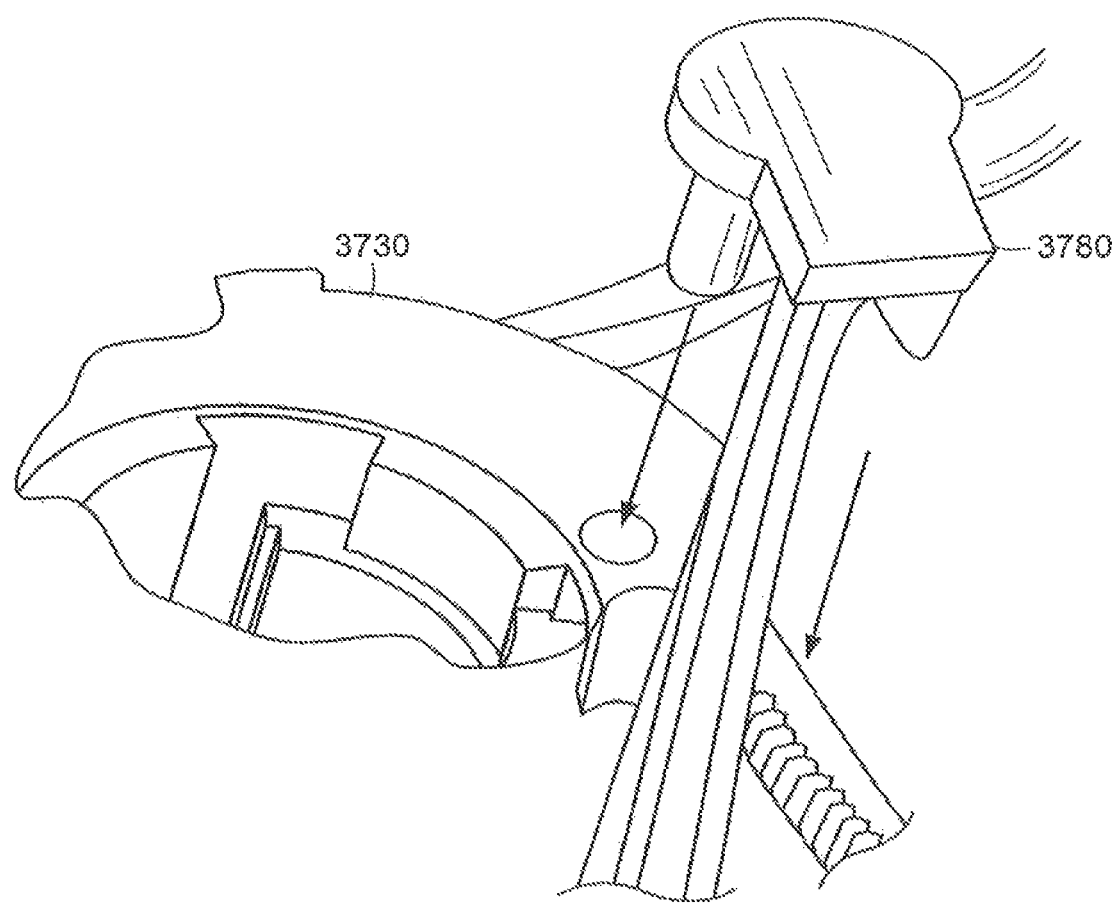
Figure 37T:
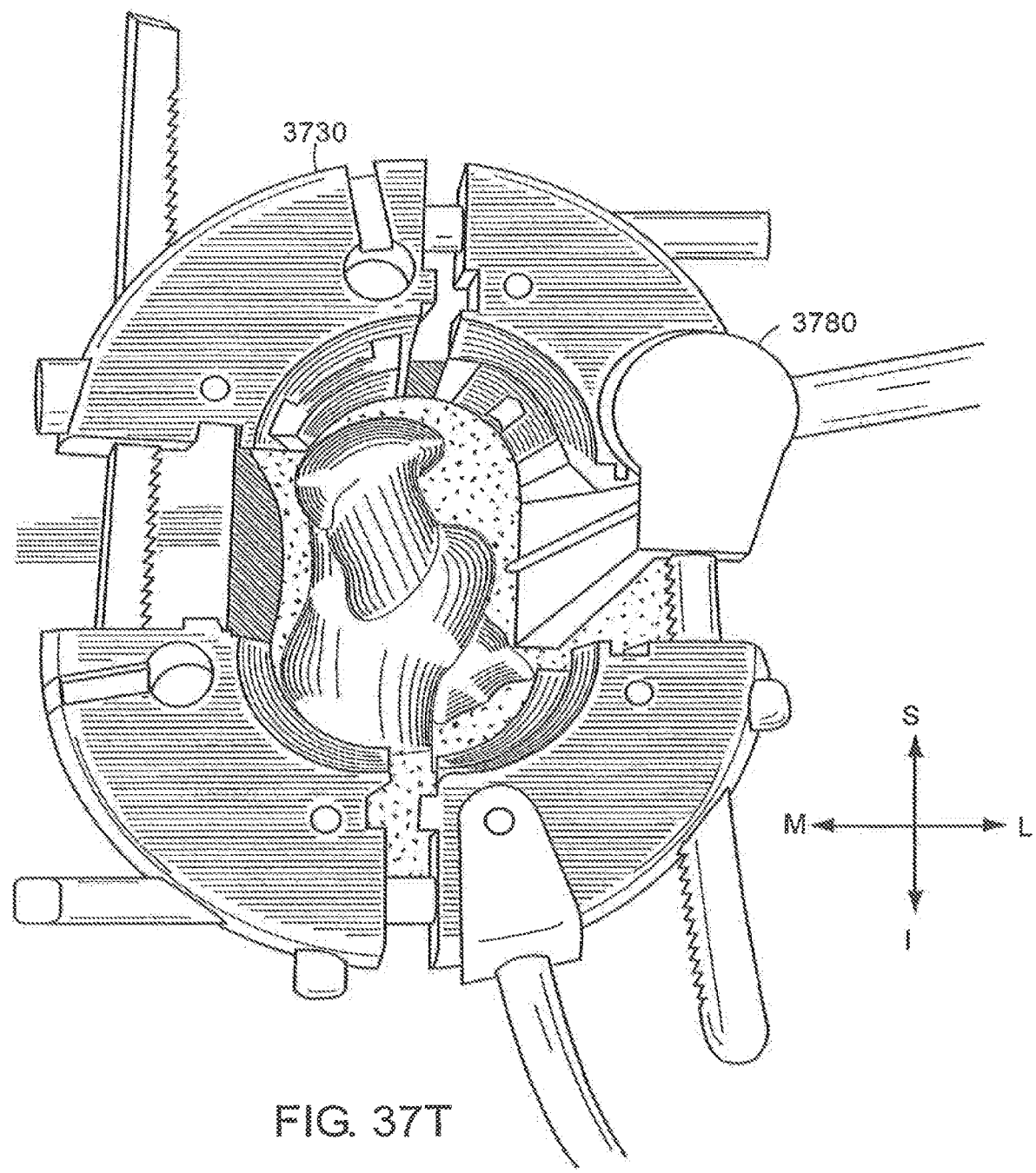
Figure 37U:
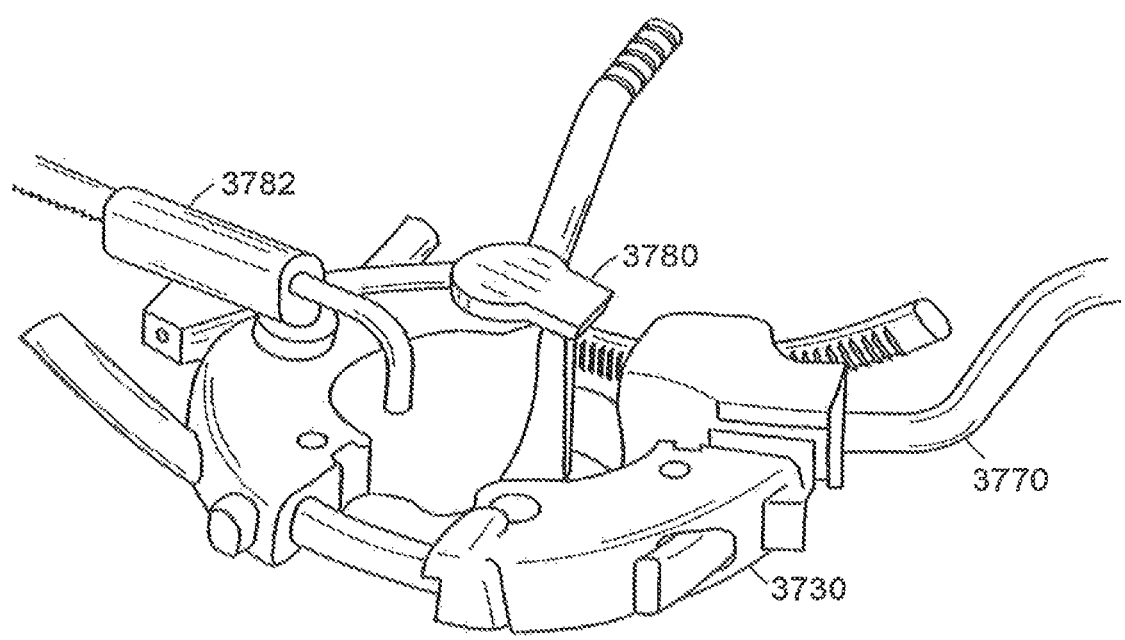

If desired, additional blades and/or surgical instruments can be attached to retractor 3730. FIGS. 37S-37U illustrate such attachments. FIG. 37S illustrates the attachment of medial-lateral blade 3780 to a portion of retractor 3730 that includes an attachment point of a base component of retractor 3730. FIG. 37T illustrates a top view of retractor 3730 after blade 3780 assembled to retractor 3730. Blade 3780 is secured to an attachment point and is supported by a portion of an arm. FIG. 37U illustrates light source 3782 attached to refractor 3730. If desired, light source 3782 is adjusted inward or outward, depending on the amount of expansion of retractor 3730.

In some embodiments, this invention includes a surgical method comprising incising tissue of a mammal to create an incision, expanding the incision to create a pathway from the incision to a surgical site, directing a refractor (e.g., a retractor of the invention) into the pathway, creating a working channel, and performing at least a portion of a surgical procedure through the working channel. The working channel can be created by, for example, expanding the retractor by separating a first retractor blade from a second retractor blade by moving at least one of the first retractor blade and the second retractor blade along a first connector of the refractor, and separating a third retractor blade from a fourth retractor blade by moving at least one of the third retractor blade and the fourth retractor blade along a second connector, wherein the second connector is oriented at an angle to the first connector.

In some embodiments, this invention provides methods of providing access to vertebrae. In one embodiment, the method comprises incising tissue of a mammal to create an incision, expanding the incision to create a pathway from the incision to a surgical site, directing a retractor (e.g., a retractor of the invention) into the pathway, creating a working channel through the retractor by separating at least two retractor blades, performing at least a portion of a surgical procedure through the working channel at a first vertebra, exposing a second vertebra that is adjacent to the first vertebra by directing an instrument or implant between two of the retractor blades to displace tissue adjacent to the second vertebra; and performing at least a portion of a surgical procedure through the working channel at the second vertebra. The tissue adjacent to the second vertebra can be displaced by directing an instrument or implant between two of the retractor blades and cutting or moving the tissue away from near the second vertebra, thus allowing a practitioner to access two vertebrae without the need to increase the incision in the skin of a mammal and/or create a second incision in the skin of a mammal.

In some embodiments, the first, second, third, and/or fourth retractor blades are moved along a nonlinear line (e.g., an acute line). In other embodiments, the blades are moved along a linear line (i.e., a straight line).

In some embodiments, this invention includes a kit comprising a surgical retractor, a retractor inserter that can be assembled to a frame of the refractor, a blade depth tower, a distractor, and at least one blade adjustment instrument (e.g., one of the instruments mentioned previously, such as, for example, a blade remover instrument, a blade pusher instrument). In further embodiments, the kit includes at least one obtruator and at least two dilators (e.g., two or more dilators of dissimilar diameter). In still more embodiments, the kit includes at least portions of an attachment device (e.g., portions of a rigid attachment arm).

What is claimed is:

1. A surgical retractor, comprising:
 a first retractor blade and a second retractor blade;
 a first connector assembled to a proximal end of the first retractor blade and a proximal end of the second retractor blade, wherein at least the first retractor blade or the second retractor blade is movable along a line that is parallel to a length of the first connector;
 a third retractor blade and a fourth retractor blade; and
 a second connector assembled to a proximal end of the third retractor blade and a proximal end of the fourth retractor blade, wherein at least the third retractor blade or the fourth retractor blade is movable along a line that is parallel to a length of the second connector, and wherein at least the first connector or the second connector is movable along a line that intersects the first connector and the second connector;
 wherein the second and fourth retractor blades move together with respect to the first and third retractor blades.

2. The retractor of claim 1, wherein the first connector or second connector is curved.

3. The retractor of claim 1, wherein the first retractor blade or second retractor blade is attached to a base component and the base component is attached to the first connector.

4. The retractor of claim 1, wherein the retractor blades are movable to a position in which the blades collectively define a conduit.

* * * * *